United States Patent
Ishida et al.

(10) Patent No.: US 8,632,792 B2
(45) Date of Patent: Jan. 21, 2014

(54) COOLING SENSATION AGENT COMPOSITION AND SENSORY STIMULATION AGENT COMPOSITION

(75) Inventors: Kenya Ishida, Kanagawa (JP); Takashi Aida, Kanagawa (JP); Tetsuya Yamamoto, Shizuoka (JP)

(73) Assignee: Takasago International Corporation, Tokyo (JP)

( * ) Notice: Subject to any disclaimer, the term of this patent is extended or adjusted under 35 U.S.C. 154(b) by 351 days.

(21) Appl. No.: 12/936,160

(22) PCT Filed: Apr. 1, 2009

(86) PCT No.: PCT/JP2009/057152
§ 371 (c)(1),
(2), (4) Date: Oct. 1, 2010

(87) PCT Pub. No.: WO2009/123355
PCT Pub. Date: Oct. 8, 2009

(65) Prior Publication Data
US 2011/0117147 A1    May 19, 2011

(30) Foreign Application Priority Data
Apr. 1, 2008    (JP) ................. 2008-095167

(51) Int. Cl.
| | |
|---|---|
| A61K 8/02 | (2006.01) |
| A61K 31/335 | (2006.01) |
| A61K 31/265 | (2006.01) |
| A61K 31/22 | (2006.01) |
| A61K 31/23 | (2006.01) |
| A01N 25/34 | (2006.01) |
| A23L 1/22 | (2006.01) |
| A23L 1/221 | (2006.01) |
| C07C 69/96 | (2006.01) |
| C07C 69/00 | (2006.01) |
| C07C 69/52 | (2006.01) |
| C07D 317/00 | (2006.01) |

(52) U.S. Cl.
USPC ........... 424/401; 424/402; 426/536; 426/650; 514/467; 514/512; 514/549; 514/552; 549/453; 558/260; 558/276; 558/277; 560/129; 560/220

(58) Field of Classification Search
USPC ........... 424/401, 402; 426/536, 650; 514/467, 514/512, 549, 552; 549/453; 558/260, 276, 558/277; 560/129, 220
See application file for complete search history.

(56) References Cited

U.S. PATENT DOCUMENTS

| | | | |
|---|---|---|---|
| 3,312,226 A | 4/1967 | Bayley et al. | |
| 3,332,428 A | 7/1967 | Mold et al. | |
| 4,119,106 A | 10/1978 | Grubbs et al. | |
| 4,459,425 A | 7/1984 | Amano et al. | |
| 5,545,424 A | 8/1996 | Nakatsu et al. | |
| 5,753,609 A | 5/1998 | Nakatsu et al. | |
| 6,365,215 B1 | 4/2002 | Grainger et al. | |
| 6,884,906 B2 | 4/2005 | Dewis et al. | |

FOREIGN PATENT DOCUMENTS

| | | |
|---|---|---|
| DE | 99057 C | 7/1898 |
| DE | 206055 C | 1/1909 |
| EP | 0 816 322 A1 | 1/1998 |
| EP | 1 077 251 A1 | 2/2001 |
| EP | 1 167 340 A2 | 1/2002 |
| GB | 1 353 381 | 5/1974 |
| JP | 8-225564 | 9/1996 |
| JP | 10-095752 | 4/1998 |
| JP | 2000-096443 | 4/2000 |
| JP | 2006-161226 | 6/2006 |
| WO | WO 94/06441 | 3/1994 |
| WO | WO 95/04809 | 2/1995 |
| WO | WO 97/16523 | 5/1997 |
| WO | WO 2005/023749 A2 | 3/2005 |
| WO | WO 2005/025313 A1 | 3/2005 |
| WO | WO 2007/126430 A1 | 11/2007 |

OTHER PUBLICATIONS

Beilstein Institute for Organic Chemistry, Frankfurt-Main, DE; BRN 3558360 1990, XP002549230.
Beilstein Institute for Organic Chemistry, Frankfurt-Main, DE; BRN 4910522 1992, XP002549231.
Beilstein Institute for Organic Chemistry, Frankfurt-Main, DE; BRN 6125701 1968, XP002549232.
Beilstein Institute for Organic Chemistry, Frankfurt-Main, DE; BRN 11337273 2007, XP002549233.
Beilstein Institute for Organic Chemistry, Frankfurt-Main, DE; BRN 9596387 2003, XP002549234.
Beilstein Institute for Organic Chemistry, Frankfurt-Main, DE; BRN 7218919 1995, XP002549235.
Beilstein Institute for OrganiC Chemistry, Frankfurt-Main, DE; BRN 6150984 1993, XP002549236.

(Continued)

*Primary Examiner* — Sue Liu
*Assistant Examiner* — Nathan W Schlientz
(74) *Attorney, Agent, or Firm* — McDermott Will & Emery LLP

(57) ABSTRACT

A cooling sensation agent composition with a prolonged cool sensation effect is provided comprising at least one compound selected from the group consisting of aceia or ketal derivatives of 3-(1-menthoxy)propan-1,2-diol represented by Formula (1), single or mixed carbonic esters ol one or two kinds ol alcohols represented by Formula (2), and carboxylic esters represented by Formula (4). A sensory stimulation agoni composition, a flavor or fragrance composition, a beverage or food product, a perfume or cosmetic product, a toiletry product, a daily utensil product or grocery, a fiber, a fiber product, a cloth or a medicine comprising the cooling sensation agent composition; a production method thereof; a cooling processing method of a fiber, fiber product or a cloth, comprising compounding the cooling sensation agent; and new compounds are also provided.

16 Claims, No Drawings

(56) References Cited

OTHER PUBLICATIONS

Beilstein Institute for Organic Chemistry, Frankfurt-Main, DE; BRN 7007279 1978, XP002549237.

Andreas Herrmann, "Controlled Release of Volatiles under Mild Reaction Conditions: From Nature to Everyday Products," Agnew. Chem. Int. Ed., 2007, 46, 5836-5863.

Ite et al., "Catalytic Asymmetric Epoxidation of Unfunctionalized Olefins," Tetrahedron Letters, vol. 31, No. 50, 1990, pp. 7345,7348.

Light et al., "Identification of Prostaglandins in the Gorgonian Plexaura Homomalla," European Journal of Biochemistry, vol. 28, 1972, p. 232-240.

S. Wilmouth et al., "Lactone Kinetic Resolution by Acylation," European Journal of Organic Chemistry, 2005, pp. 4806-4814.

US 8,632,792 B2

COOLING SENSATION AGENT COMPOSITION AND SENSORY STIMULATION AGENT COMPOSITION

RELATED APPLICATIONS

This application is the U.S. National Phase under 35 U.S.C. § 371 of International Application No. PCT/JP2009/057152, filed on Apr. 1, 2009, which in turn claims the benefit of Japanese Application No. 2008-095167, filed on Apr. 1, 2008, the disclosures of which Applications are incorporated by reference herein.

TECHNICAL FIELD

The present invention relates to a cooling sensation agent composition containing acetal or ketal derivatives of 3-(1-menthoxy)propan-1,2-diol, single or mixed carbonic esters or carboxylic esters; sensory stimulation agent compositions containing the cooling sensation agent composition; flavor or fragrance compositions, beverage or food products, perfume or cosmetic products, toiletry products, daily utensil products and groceries, fibers, fiber products, clothes and medicines containing the cooling sensation agent composition or the sensory stimulation agent composition; production methods thereof; a method of providing long-lasting cooling action by using the cooling sensation agent composition or the sensory stimulation agent composition; and a cool-processing method. The present invention also relates to new acetal or ketal derivatives of 3-(1-menthoxy)propan-1,2-diol, new single or mixed carbonic esters and new carboxylic esters.

BACKGROUND ART

A cooling sensation agent that endows the skin, oral cavity, nose and throat of a person with a refresh feeling (refresh sensation) and cool feeling (cooling sensation), that is cooling sensation effect, is used in various products such as toothpastes, confectioneries such as chewing gums and candies, tobacco, cataplasms, bath agents and cosmetics. 1-Menthol has been known as a representative cooling sensation agent, however the cooling sensation effect thereof does not last so long. Therefore, studies of prolonging cooling action thereof have been conducted. Examples of compounds with long-lasting cooling action over a prolonged period developed include menthoxypropanediol which is glycerol ether of menthol, lactic ester of menthol, and ethylene glycol ether of menthol.

However, under influence of recent global warming, there has been a demand for cool processing of clothes and the like to make people feel more comfortable even in hot summer. Most cooling sensation agents are highly volatile and also highly water-soluble, as described above, and thus, the cool processing of clothes often resulted in decline of the action in a short period of time. For example, even if a cooling sensation agent is compounded with a detergent or a softener for example, the cooling sensation agent hardly remains on the clothing fiber after washing because of its water solubility and further, no cooling sensation agent remains after drying because of its high volatility.

Sustained-release cooling sensation agents utilizing a chemical change were developed to solve the problems described above. Examples of such agents developed include a chlorocarbonic ester or carbonic ester thereof as cooling sensation agent that contained in tobacco and releases menthol by its thermal decomposition on combustion of tobacco and thus, providing tobacco with refreshment when inhaled (see Patent Document 1 below), a carbonic esters that releases a fragrance component by decomposition thereof on the skin, thus elongating the diffusion period of a fragrance (see Patent Document 2 below), and an ortho ester that releases a fragrance when decomposed by perspiration on the skin (see Patent Document 3 below), and the like. In addition, there are many patents that utilize release of a fragrance molecule by decomposition of a fragrance precursor based on a chemical change or an enzyme reaction (see Patent Documents 4 to 7, Non-patent Document 1 below and others). However, these compounds still had problems such as significantly longer period needed for release of a fragrance compound in decomposition reaction after adhesion to cloth or skin and its lower strength, and thus, there being still many problems to be overcome.

Other studies on the method of providing clothes with cooling action using microcapsules and the like have been conducted, and many patent applications has been filed. Examples thereof include a fiber processing method of using microcapsules containing mint oil or 1-menthol (see Patent Document 8) and a fiber processing method of using a microcapsulated substance melting at a temperature not higher than the body temperature, so that the substance gives persons a cooling action reversibly by latent heat when in contact with skin (see Patent Document 9). However, in the former method, of course, processed fibers loses its action after release of the cooling sensation agent by breakdown of the microcapsules, and it is actually impossible to process the clothes similarly at home. In addition, because the stage of releasing the cooling sensation agent by breakdown of the microcapsules is the rate-determining step in this method, as same as chemical reaction, it is not currently at the technological level providing persons the cooling action immediately after wearing of the cloth. In addition, the latter method, which relies on phase transition between solid and liquid, cannot provide persons the cooling action in areas where it is so hot that the microcapsulated substance does not return to the solid phase after melting.

Patent Document 1: U.S. Pat. No. 3,312,226
Patent Document 2: JP-A No. 10-95752
Patent Document 3: WO 94/06441A
Patent Document 4: EP Patent No. 1077251A
Patent Document 5: WO 95/04809A
Patent Document 6: WO 97/16523A
Patent Document 7: JP-A No. 8-225564
Patent Document 8: JP-A No. 2000-96443
Patent Document 9: JP-A No. 2006-161226
Nonpatent Document 1: Angew. Chem. Int. Ed, 2007, 46, 5836-5863

SUMMARY OF THE INVENTION

Problems to be Solved by the Invention

An object of the present invention is to provide a cooling sensation agent composition wherein the conventional problems were resolved, i.e., to provide a cooling sensation agent composition showing the long-lasting cooling action for an extended period of time.

Another object of the present invention is to provide a sensory stimulation agent composition containing the cooling sensation agent composition.

Yet another object of the present invention is to provide a flavor or fragrance composition, a beverage or food product, a perfume or cosmetic product, a toiletry product, daily utensil product and groceries, and a medicine, which contain the cooling sensation agent composition or sensory stimulant, and also a production method thereof.

Yet another object of the present invention is to provide a method of providing a prolonged cooling action by applying one of the aforementioned products containing the cooling sensation agent composition directly on skin or scalp, administering it into oral cavity, or applying it on fibers, clothes or fabric, or a cooling processing method of fibers, clothes or fabric by processing those with a cooling sensation agent composition or compounding a cooling sensation agent composition with the fiber.

Yet another object of the present invention is to provide new acetal and ketal derivatives of 3-(1-menthoxy)propan-1,2-diol, new single or mixed carbonic esters and new carboxylic esters.

Means for Solving the Problems

After intensive studies to solve the problems above, the inventors have found that: acetal or ketal derivatives of 3-(1-menthoxy)propan-1,2-diol, carbonic ester derivatives of menthol or the analogue thereof, and carboxylic esters of menthol or the analogue thereof have a prolonged cooling action; they remain after washing in clothes and others when compounded with a detergent or softener; the clothes washed by using such a composition have gentle and long-lasting cooling action during or after wearing; and they show a prolonged cooling action when contained for example in beverage or food products, perfume or cosmetic products, toiletry products, daily utensil products and groceries, or medicines, and the present invention being made based on these findings.

Accordingly, the present invention relates to the following cooling sensation agent composition; the following sensory stimulation agent composition; the following flavor or fragrance composition, beverage or food product, perfume or cosmetic product, toiletry product, daily utensil product and grocery, fiber, fiber product, clothes or medicine, which contains the cooling sensation agent composition or sensory stimulation agent composition and the production method thereof; the following method of providing a prolonged cooling action; and the following cool processing method of fibers, clothes and fabric. The present invention also relates to new acetals and ketals, new single or mixed carbonic esters, and new carboxylic esters of 3-(1-menthoxy)propan-1,2-diol.

[1] A cooling sensation agent composition, comprising at least one compound selected from acetals or ketals, single or mixed carbonic esters, mixed carbonic esters, and carboxylic esters consisting of the compounds represented by the following Formulae (1) to (4):

acetals or ketals represented by Formula (1):

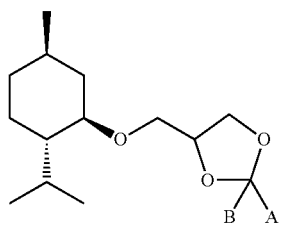

(1)

wherein, A and B each represent independently a hydrogen atom or a hydrocarbon group which may have one or more substituents, in which A and B are not hydrogen atoms simultaneously, and the total number of carbon atoms in A and B is in the range of 6 to 18;

single or mixed carbonic esters of one or two kinds of alcohols represented by Formula (2):

(2)

wherein, $R^1$ and $R^2$ each represent independently a residue of an alcohol selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol and para-menthan-3,8-diol;

mixed carbonic esters of two kinds of alcohols represented by Formula (3):

(3)

wherein, $R^3$ represents a residue of alcohol selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol, and para-menthan-3,8-diol; and $R^4$ represents a residue of a branched or straight-chain, cyclic or linear, or saturated or unsaturated alcohol having 6 to 18 carbon atoms that may have one or more aromatic rings that may have a condensed ring and substituent groups such as hydroxyl and ether groups and; and carboxylic esters represented by Formula (4):

(4)

wherein, $R^5$ represents a residue of an alcohol selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol and para-menthan-3,8-diol; and $R^6$ represents a hydrocarbon group having 11 to 19 carbon atoms that may be branched and contain one or more unsaturated bonds.

[2] The cooling sensation agent composition described in the item [1] above, wherein the compounds represented by Formulae (1) to (4) above have a ClogP of 3.0 or more and a molecular weight of 250 or more and 600 or less and provide a prolonged cooling action.

[3] The cooling sensation agent composition described in the item [1] above, further comprising at least one kind of cooling sensation substance other than the compounds represented by Formulae (1) to (4) above.

[4] The cooling sensation agent composition described in the item [3] above, wherein the cooling sensation substance other than the compounds of Formulae (1) to (4) above is menthol, menthone, camphor, pulegol, isopulegol, cineol, mint oil, peppermint oil, spearmint oil, eucalyptus oil, 3-(1-menthoxy)propan-1,2-diol, N-alkyl-p-menthane-3-carboxamide, 2-methyl-3-(1-menthoxy)propan-1,2-diol, p-menthan-3,8-diol, 2-(1-menthoxy)ethan-1-ol, 3-(1-menthoxy)propan-1-ol, 4-(1-menthoxy)butan-1-ol, menthyl 3-hydroxybutanoate, menthyl lactate, menthone glycerol ketal, N-methyl-2,2-isopropylmethyl-3-methylbutane amide or menthyl glyoxylate.

[5] A sensory stimulation agent composition, comprising the cooling sensation agent composition described in the item [1] above.

[6] The sensory stimulation agent composition described in the item [5] above, further comprising at least one warming and pungent substance.

[7] The sensory stimulation agent composition described in the item [6] above, wherein the warming and pungent substance is vanillyl ethyl ether, vanillyl propyl ether, vanillin propylene glycol acetal, ethylvanillin propylene glycol acetal, capsaicin, gingerol, vanillyl butyl ether, 4-(1-menthoxymethyl)-2-(3'-methoxy-4'-hydroxyphenyl)-1,3-dioxolane, pepper oil, pepper oleoresin, ginger oleoresin, nonylic acid vanillyl amide, jamboo oleoresin, *Zanthoxylum Piperitum* Peel Extract, sanshool-I, sanshool-II, sanshoamide, black pepper extract, chavicine, piperine or spilanthol.

[8] A flavor or fragrance composition, a beverage or food product, a perfume or cosmetic product, a toiletry product, a daily utensil product or grocery, a fiber, a fiber product, a cloth or a medicine, containing a cooling sensation agent composition or a sensory stimulation agent composition described in the item [1] or [7] above.

[9] A method of providing long-lasting cooling sensation effect, comprising applying any one of the products described in the item [8] above directly to skin or scalp, administering it into oral cavity, or applying it to a fiber, a fiber product or a cloth.

[10] A flavor or fragrance composition, comprising the cooling sensation agent composition or the sensory stimulation agent composition described in the item [1] or [7] above in an amount of 0.0001 to 90% by mass.

[11] A beverage or food product, a perfume or cosmetic product, a toiletry product, a daily utensil product or grocery, a fiber, a fiber product, a cloth or a medicine, comprising a cooling sensation agent composition or a sensory stimulation agent composition described in the item [1] or [7] above in an amount of $10^{-7}$ to 20% by mass.

[12] A cooling processing method of a fiber, a cloth or a cloth material, comprising compounding the cooling sensation agent composition or the sensory stimulation agent composition described in the item [1] or [7] above to a fiber, a cloth or a cloth material, or processing a fiber, a cloth or a cloth material with the cooling sensation agent composition or the sensory stimulation agent composition described in the item [1] or [7] above.

[13] A method of producing a flavor or fragrance composition, a beverage or food product, a perfume or cosmetic product, a toiletry product, a daily utensil product or grocery or a medicine, comprising compounding a cooling sensation agent composition or a sensory stimulation agent composition described in the item [1] or [7] above.

[14] An acetal or ketal represented by Formula (1'):

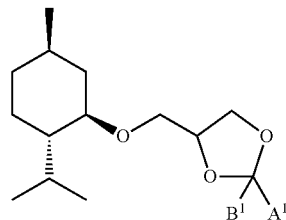

wherein, $A^1$ and $B^1$ each represent independently a hydrogen atom or a hydrocarbon group which may have one or more substituents, and the total number of carbon atoms in $A^1$ and $B^1$ is in the range of 6 to 18; however, $A^1$ and $B^1$ are not hydrogen atoms simultaneously; and, when either of $A^1$ and $B^1$ is a hydrogen atom, the other $A^1$ or $B^1$ is a saturated or unsaturated straight-chain, branched or alicyclic hydrocarbon group which may have one or more substituents.

[15] A single or mixed carbonic ester of one or two kinds of alcohols represented by Formula (2'):

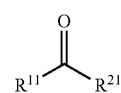

wherein, $R^{11}$ and $R^{21}$ each represent independently a residue of an alcohol selected from a group consisting of 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol, and para-menthan-3,8-diol; however, $R^{11}$ and $R^{21}$ are not 1-menthol residues at the same time.

[16] A mixed carbonic ester of two kinds of alcohols represented by Formula (3'):

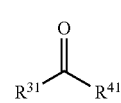

wherein, $R^{31}$ represents a residue of an alcohol selected from a group consisting of 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol, and para-menthan-3,8-diol; $R^{41}$ represents a residue of a branched or straight-chain, cyclic or linear, or saturated or unsaturated alcohol having 6 to 18 carbon atoms that may have one or more aromatic rings that may have a condensed ring and substituent groups such as hydroxyl and ether groups; however, $R^{41}$ is not an unsaturated branched alcohol residue).

[17] A carboxylic ester represented by Formula (4):

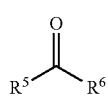

(4)

wherein, $R^5$ represents a residue of an alcohol selected from a group consisting of 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol and para-menthan-3,8-diol; and $R^6$ represents a hydrocarbon group having 11 to 19 carbon atoms that may be branched and contain one or more unsaturated bonds.

Advantageous Effects of the Invention

The present invention provides a cooling sensation agent composition providing a cooling sensation effect lasting for a long period of time. In addition, the sensory stimulation agent compositions obtained by using the cooling sensation agent composition providing a cooling sensation effect lasting for a long period of time provides a sense-stimulating action lasting for a long period of time. Further, by compounding the cooling sensation agent composition or the sensory stimulation agent composition with a flavor or fragrance composition, a beverage or food product, a perfume or cosmetic product, a toiletry product, a daily utensil products or grocery, a fiber, a fiber product, a cloth and a medicine, it is possible to prepare the product thereof providing the cooling sensation effect or the sensation stimulating effect lasting for a long period of time. These products may be applied directly on skin or scalp, administered into oral cavity or applied onto a fiber, a cloth or the like, for providing the skin, scalp, or oral cavity with a prolonged cool feeling or sensation stimulating feeling, and when applied to the fiber product or the cloth, providing a gentle and prolonged cooling sensation effect at and also after wearing. The present invention also provides a cooling sensation agent composition that gives, if compounded with a detergent, a softener or the like, a washed cloth providing prolonged gentle cool feeling at and/or after wearing. In addition, the present invention provides new compounds.

BEST MODE OF CARRYING OUT THE INVENTION

Hereinafter, the present invention will be described in more detail.

The present invention relates to a cooling sensation agent composition, comprising at least one compound selected from acetals or ketals, single or mixed carbonic esters, mixed carbonic esters, and carboxylic esters consisting of the compounds represented by the following Formulae (1) to (4).

Acetals or ketals represented by Formula (1):

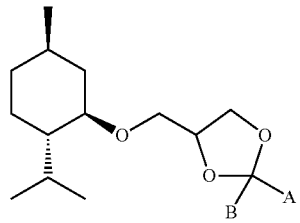

(1)

wherein, A and B each represent independently a hydrogen atom or a hydrocarbon group which may have one or more substituents, in which A and B are not hydrogen atoms simultaneously, and the total number of carbon atoms in A and B is in the range of 6 to 18;

single or mixed carbonic esters of one or two kinds of alcohols represented by Formula (2):

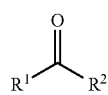

(2)

wherein, $R^1$ and $R^2$ each represent independently a residue of an alcohol selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol and para-menthan-3,8-diol);

mixed carbonic esters of two kinds of alcohols represented by Formula (3):

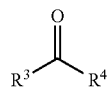

(3)

wherein, $R^3$ represents a residue of alcohol selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol, and para-menthan-3,8-diol; and $R^4$ represents a residue of a branched or straight-chain, cyclic or linear, or saturated or unsaturated alcohol having 6 to 18 carbon atoms that may have one or more aromatic rings that may have a condensed ring and substituent groups such as hydroxyl and ether groups; and carboxylic esters represented by Formula (4):

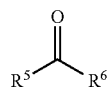

(4)

wherein, $R^5$ represents a residue of an alcohol selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol and para-menthan-3,8-diol; and $R^6$ represents a hydrocarbon group having 11 to 19 carbon atoms that may be branched and contain one or more unsaturated bonds.

In the formulae 3 and 4, the group R³ is preferably 1-menthol or 1-isopulegol, the group R⁴ is preferably a unsaturated, branched- or straight-chain alcohol with carbon atoms of 6 to 14, which contains an ether group, and the group R⁵ is preferably 1-menthol or 1-isopulegol.

Hereinafter, the volatility and the oleophilicity of the compounds represented by Formulae (1) to (4) used in the cooling sensation agent composition of the present invention will be described.

The volatility of a compound is influenced significantly by the functional group connected to a molecule of the compound. On the other hand, increases in molecular weight can lead to increase of its flashing or boiling point, and a compound having a molecular weight of approximately 250 to 600, preferably 300 to 500, is a less volatile compound. In addition, a compound having a molecular weight of more than 600 shows almost no cool feeling. For that reason, the compounds represented by Formulae (1) to (4) used in the cooling sensation agent composition of the present invention preferably have a molecular weight in the range of 300 to 600.

The oleophilicity of a compound is influenced significantly by the functional group connected to a molecule of the compound and the number of carbons thereof; and presence of a hydroxyl group leads to decrease of oleophilicity, while increase in the number of carbons leads to increase of oleophilicity. Water/octanol distribution coefficient (ClogP) is normally used as the indicator of oleophilicity. As a result, menthol for example has a ClogP of 2.5, while dimenthyl carbonate having not only the hydroxyl group blocked with carbonic esters but also an increased molecular weight has a ClogP of 4.5, and thus, it is more highly oleophilic and less soluble in water. The ClogP values of the compounds of Formulae (1) to (4) used in the cooling sensation agent composition of the present invention are in the range of 3.0 or more, more preferably 4.0 or more.

As described above, there exist many prior arts about carbonic esters of menthol and the like, but these are precursor compounds giving cool feeling by release of menthol and the like by decomposition reaction thereof by heat or acid. However in the present invention, it is found that the compound itself shows cooling sensation without decomposition of carbonic esters of menthol or the analogue thereof. There is no report that the compounds represented by Formula (2) have such properties till now.

Further in these prior arts, there is no report on the single or mixed carbonic ester compounds of one or two kinds of alcohols selected from a residue of the alcohol selected from 1-menthol, 1-isopulegol, 3-(1-menthoxy)propan-1,2-diol, 2-(1-menthoxy)ethan-1-ol, 3-(1-menthoxy) propan-1-ol, 2-methyl-3-(1-menthoxy) propan-1,2-diol, and para-menthan-3,8-diol, except dimenthyl carbonates in which two alcohol residues have menthol or 1-menthol at the same time. Therefore, these compounds are new substances. There are various possible combinations of alcohol residues, such as the single carbonic ester represented by the following Formula, di-1-isopulegol carbonate:

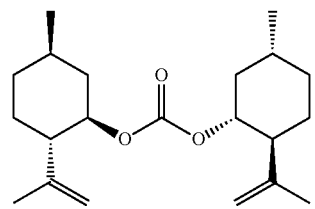 [SMILES: C=C(C)[C@@H]1CC[C@@H](C)C[C@H]1OC(=O)O[C@@H]1C[C@H](C)CC[C@H]1C(=C)C]

and the mixed carbonic ester represented by the following Formula, 1-menthoxy ethan-1-ol-1-isopulegol carbonate:

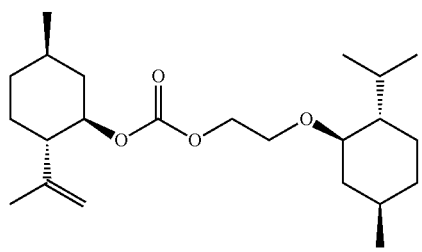 [SMILES: C=C(C)[C@@H]1CC[C@@H](C)C[C@H]1OC(=O)OCCO[C@@H]1C[C@H](C)CC[C@H]1C(C)C]

but these compounds are also new compounds that are not reported yet.

In addition, it is found that carbonic ester of which one alcohol residue is a residue of an alcohol selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol, and para-menthan-3,8-diol and the other alcohol residue is a residue of a branched or straight-chain, cyclic or linear, or saturated or unsaturated alcohol having 5 to 18 carbon atoms, that may have one or more substituent groups such as hydroxyl and ether groups and that may have an aromatic ring or an accompanying fused ring, shows cooling sensation without decomposition, and there is also no report on such actions of the carbonic esters. These carbonic esters are compounds represented by Formula (3). The compounds from which a compound in which one alcohol residue is a residue of 1-menthol is excluded, that is the compounds represented by Formula (3') are new compounds.

Similarly, there are many reports on acetal or ketal compounds as precursor compounds, from which 1-menthol, flavor or fragrance is released by decomposition reaction thereof to feel cool sensation or note. However, the acetals or ketals of the present invention represented by following Formula (1) do not decompose;

(1)

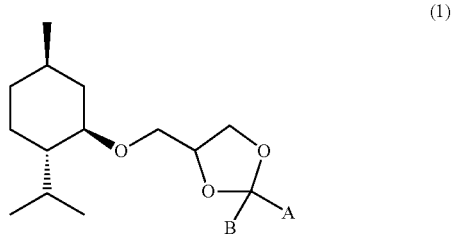

wherein, each of A and B is a hydrogen atom or a hydrocarbon group which may have one or more substituents, in which A and B are not hydrogen atoms simultaneously, and the total number of carbon atoms in A and B is in the range of 6 to 18.

In the present invention, it is found that the compounds represented by Formula (1) itself show cooling sensation action without decomposition. There is not report on this at all till now.

Further, in compounds represented by Formula (1), the compounds represented by Formula (1') below are new substances.

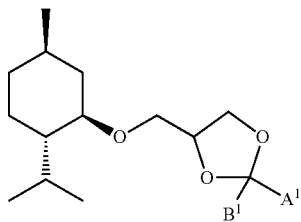

(1')

wherein, $A^1$ and $B^1$ each represent independently a hydrogen atom or a hydrocarbon group which may have one or more substituents, and the total number of carbon atoms in $A^1$ and $B^1$ is in the range of 6 to 18; however, $A^1$ and $B^1$ are not hydrogen atoms simultaneously; and, when either of $A^1$ and $B^1$ is a hydrogen atom, the other $A^1$ or $B^1$ is a saturated or unsaturated straight-chain, branched or alicyclic hydrocarbon group which may have one or more substituents.

For example, 3-(1-menthoxy) propan-1,2-diol-6-methyl-2-heptenone ketal represented by the following Formula is a new compound that is not reported yet.

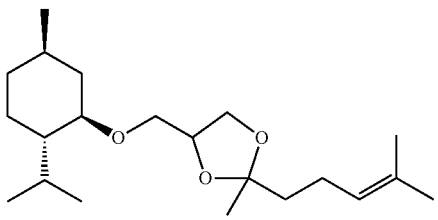 [SMILES: CC(C)=CCCC1(C)OCC(CO[C@@H]2C[C@H](C)CC[C@H]2C(C)C)O1]

Similarly, there are some reports on ester or enol ester compounds as precursor compounds of menthol, from which flavor or fragrance is released by decomposition reaction thereof to feel note. However there is completely no report indicating that the single or mixed carbonic or carboxylic esters of the present invention, formed by using an alcohol selected from 1-menthol, 1-isopulegol, 3-(1-menthoxy)propan-1,2-diol, 2-(1-menthoxy)ethan-1-ol, 3-(1-menthoxy) propan-1-ol, 2-methyl-3-(1-menthoxy)propan-1,2-diol and para-menthan-3,8-diol as at least one component do not decompose and have a prolonged cooling sensation action. In addition, these carboxylic esters are new compounds not reported till now.

The aldehyde and ketone which is a raw material for constituting the groups A and B defined in the formula (1) of the present invention, the group A and B each representing independently a hydrogen atom or a hydrocarbon group which may have a substituent, wherein A and B are not hydrogen atoms simultaneously and the sum of the carbon numbers of A and B is in the range of 6 to 18, includes particularly, for example, a branched or straight-chain, cyclic or linear, saturated or unsaturated aldehyde and ketone, which form groups A and B with 6 to 18 carbon atoms in all, may have one or more substituents such as hydroxyl and ether groups and may have an aromatic ring and an fused ring connected thereto.

Examples of the straight-chain or branched aldehydes among the aldehydes or ketones above include, but are not particularly limited to, heptanal, octanal, nonanal, decanal, undecanal, dodecanal, tridecanal, tetradecanal, pentadecanal, hexadecanal, heptadecanal, octadecanal, 2-methylhexanal, 3-methylhexanal, 4-methylhexanal, 5-methylhexanal, 2-methylheptanal, 3-methylheptanal, 4-methylheptanal, 5-methylheptanal, 6-methylheptanal, 2-methyloctanal, 3-methyloctanal, 4-methyloctanal, 5-methyloctanal, 6-methyloctanal, 7-methyloctanal, 2-methylnonanal, 3-methylnonanal, 4-methylnonanal, 5-methylnonanal, 6-methylnonanal, 7-methylnonanal, 8-methylnonanal, 2-methyldecanal, 3-methyldecanal, 4-methyldecanal, 5-methyldecanal, 6-methyldecanal, 7-methyldecanal, 8-methyldecanal, 9-methyldecanal, 2-methylundecanal, 2,3-dimethylpentanal, 2,4-dimethylpentanal, 2,2-dimethylpentanal, 3,3-dimethylpentanal, 3,4-dimethylpentanal, 4,4-dimethylpentanal, 2,2-dimethylhexanal, 2,3-dimethylhexanal, 2,4-dimethylhexanal, 2,5-dimethylhexanal, 3,3-dimethylhexanal, 3,4-dimethylhexanal, 3,5-dimethylhexanal, 4,4-dimethylhexanal, 4,5-dimethylhexanal, 5,5-dimethylhexanal, 2,2-dimethylheptanal, 2,3-dimethylheptanal, 2,4-dimethylheptanal, 2,5-dimethylheptanal, 2,6-dimethylheptanal, 3,3-dimethylheptanal, 3,4-dimethylheptanal, 3,5-dimethylheptanal, 3,6-dimethylheptanal, 4,4-dimethylheptanal, 4,5-dimethylheptanal, 4,6-dimethylheptanal, 5,5-dimethylheptanal, 5,6-dimethylheptanal, 6,6-dimethylheptanal, 3,5,5-trimethylhexanal, 2,2-dimethyloctanal, 2,3-dimethyloctanal, 2,4-dimethyloctanal, 2,5-dimethyloctanal, 2,6-dimethyloctanal, 2,7-dimethyloctanal, 3,3-dimethyloctanal, 3,4-dimethyloctanal, 3,5-dimethyloctanal, 3,6-dimethyloctanal, 3,7-dimethyloctanal, 4,4-dimethyloctanal, 4,5-dimethyloctanal, 4,6-dimethyloctanal, 4,7-dimethyloctanal, 5,5-dimethyloctanal, 5,6-dimethyloctanal, 5,7-dimethyloctanal, 6,6-dimethyloctanal, 6,7-dimethyloctanal, 7,7-dimethyloctanal, 2,2-dimethylnonanal, 2,3-dimethylnonanal, 2,4-dimethylnonanal, 2,5-dimethylnonanal, 2,6-dimethylnonanal, 2,7-dimethylnonanal, 2,8-dimethylnonanal, 3,3-dimethylnonanal, 3,4-dimethylnonanal, 3,5-dimethylnonanal, 3,6-dimethylnonanal, 3,7-dimethylnonanal, 3,8-dimethylnonanal, 4,4-dimethylnonanal, 4,5-dimethylnonanal, 4,6-dimethylnonanal, 4,7-dimethylnonanal, 4,8-dimethylnonanal, 5,5-dimethylnonanal, 5,6-dimethylnonanal, 5,7-dimethylnonanal, 5,8-dimethylnonanal, 6,6-dimethylnonanal, 6,7-dimethylnonanal, 6,8-dimethylnonanal, 7,7-dimethylnonanal, 7,8-dimethylnonanal, 8,8-dimethylnonanal, and the like. Even if optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the straight-chain or branched unsaturated aldehydes include, but are not particularly limited to, 2-heptenal, 2-octenal, 2-nonenal, 2-decenal, 4-decenal, 2-undecenal, 10-undecenal, 2,6,10-trimethyl-9-undecenal, 2,6,10-trimethyl-5,9-undecadienal, 2-dodecenal, 2-tridecenal, 2-tetradecenal, 2-pentadecenal, 2-hexadecenal, 2-heptadecenal, 2-octadecenal, 2,6-nonadienal, 2-methyl-2-hexenal, 3-methyl-2-hexenal, 4-methyl-2-hexenal, 5-methyl-2-hexenal, 2-methyl-2- heptenal, 3-methyl-2-heptenal, 4-methyl-2-heptenal, 5-methyl-2-heptenal, 6-methyl-2-heptenal, 2-methyl-2-octenal, 3-methyl-2-octenal, 4-methyl-2-octenal, 5-methyl-2-octenal, 6-methyl-2-octenal, 7-methyl-2-octenal, 2-methyl-2-nonenal, 3-methyl-2-nonenal, 4-methyl-2-nonenal, 5-methyl-2-nonenal, 6-methyl-2-nonenal, 7-methyl-2-nonenal, 8-methyl-2-nonenal, 2-methyl-2-decenal, 3-methyl-2-decenal, 4-methyl-2-decenal, 5-methyl-2-decenal, 6-methyl-2-decenal, 7-methyl-2-decenal, 8-methyl-2-decenal, 9-methyl-2-decenal, 2,3-dimethyl-2-pentenal, 2,4-dimethyl-2-pentenal, 3,4-dimethyl-2-pentenal, 4,4-dimethyl-2-pentenal, 2,3-dimethyl-2-hexenal, 2,4-dimethyl-2-hexenal, 2,5-dimethyl-2-hexenal, 3,4-dimethyl-2-hexenal, 3,5-dimethyl-2-hexenal, 4,4-dimethyl-2-hexenal, 4,5-dimethyl-2-hexenal, 5,5-dimethyl-2-hexenal, 2,3-dimethyl-2-heptenal, 2,4-dimethyl-2-heptenal, 2,5-dimethyl-2-heptenal, 2,6-dimethyl-2-heptenal, 3,4-dimethyl-2-heptenal, 3,5-dimethyl-2-heptenal, 3,6-dimethyl-2-heptenal, 4,4-dimethyl-2-heptenal, 4,5-dimethyl-2-heptenal, 4,6-dimethyl-2-heptenal, 5,5-dimethyl-2-heptenal, 5,6-dimethyl-2-heptenal, 6,6-dimethyl-2-heptenal, 2,3-dimethyl-2-octenal, 2,4-dimethyl-2-octenal, 2,5-dimethyl-2-octenal, 2,6-dimethyl-2-octenal, 2,7-dimethyl-2-octenal, 3,4-dimethyl-2-octenal, 3,5-dimethyl-2-octenal, 3,6-dimethyl-2-octenal, 3,7-dimethyl-2-octenal, 3,7-dimethyl-6-octenal, 3,7-dimethyl-2,6-octadienal, 4,4-dimethyl-2-octenal, 4,5-dimethyl-2-octenal, 4,6-dimethyl-2-octenal, 4,7-dimethyl-2-octenal, 5,5-dimethyl-2-octenal, 5,6-dimethyl-2-octenal, 5,7-dimethyl-2-octenal, 6,6-dimethyl-2-octenal, 6,7-dimethyl-2-octenal, 7,7-dimethyl-2-octenal, 2,3-dimethyl-2-nonenal, 2,4-dimethyl-2-nonenal, 2,5-dimethyl-2-nonenal, 2,6-dimethyl-2-nonenal, 2,7-dimethyl-2-nonenal, 2,8-dimethyl-2-nonenal, 3,4-dimethyl-2-nonenal, 3,5-dimethyl-2-nonenal, 3,6-dimethyl-2-nonenal, 3,7-dimethyl-2-nonenal, 3,8-dimethyl-2-nonenal, 4,4-dimethyl-2-nonenal, 4,5-dimethyl-2-nonenal, 4,6-dimethyl-2-nonenal, 4,7-dimethyl-2-nonenal, 4,8-dimethyl-2-nonenal, 5,5-dimethyl-2-nonenal, 5,6-dimethyl-2-nonenal, 5,7-dimethyl-2-nonenal, 5,8-dimethyl-2-nonenal, 6,6-dimethyl-2-nonenal, 6,7-dimethyl-2-nonenal, 6,8-dimethyl-2-nonenal, 7,7-dimethyl-2-nonenal, 7,8-dimethyl-2-nonenal, 8,8-dimethyl-2-nonenal, 3-heptenal, 3-octenal, 3-nonenal, 3-decenal, 3-undecenal, 2-methyl-3-hexenal, 3-methyl-3-hexenal, 4-methyl-3-hexenal, 5-methyl-3-hexenal, 2-methyl-3-heptenal, 3-methyl-3-heptenal, 4-methyl-3-heptenal, 5-methyl-3-heptenal, 6-methyl-3-heptenal, 2-methyl-3-octenal, 3-methyl-3-octenal, 4-methyl-3-octenal, 5-methyl-3-octenal, 6-methyl-3-octenal, 7-methyl-3-octenal, 2-methyl-3-nonenal, 3-methyl-3-nonenal, 4-methyl-3-nonenal, 5-methyl-3-nonenal, 6-methyl-3-nonenal, 7-methyl-3-nonenal, 8-methyl-3-nonenal, 2-methyl-3-decenal, 3-methyl-3-decenal, 4-methyl-3-decenal, 5-methyl-3-decenal, 6-methyl-3-decenal, 7-methyl-3-decenal, 8-methyl-3-decenal, 9-methyl-3-decenal, and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the straight-chain or branched ketones include, but are not particularly limited to, acetoin, diacetyl, 2-heptanone, 2-octanone, 3-octanone, 2-nonanone, 2-decanone, 2-undecanone, 2-dodecanone, 2-tridecanone, 2-tetradecanone, 2-pentadecanone, 2-hexadecanone, 2-heptadecanone, 2-octadecanone, 3-methyl-2-hexanone, 4-methyl-2-hexanone, 5-methyl-2-hexanone, 3-methyl-2-heptanone, 4-methyl-2-heptanone, 5-methyl-2-heptanone, 6-methyl-2-heptanone, 3-methyl-2-octanone, 4-methyl-2-octanone, 5-methyl-2-octanone, 6-methyl-2-octanone, 7-methyl-2-octanone, 3-methyl-2-nonanone, 4-methyl-2-nonanone, 5-methyl-2-nonanone, 6-methyl-2-nonanone, 7-methyl-2-nonanone, 8-methyl-2-nonanone, 3-methyl-2-decanone, 4-methyl-2-decanone, 5-methyl-2-decanone, 6-methyl-2-decanone, 7-methyl-2-decanone, 8-methyl-2-decanone, 9-methyl-2-decanone, 3,3-dimethyl-2-pentanone, 3,4-dimethyl-2-pentanone, 4,4-dimethyl-2-pentanone, 3,3-dimethyl-2-hexanone, 3,4-dimethyl-2-hexanone, 3,5-dimethyl-2-hexanone, 4,4-dimethyl-2-hexanone, 4,5-dimethyl-2-hexanone, 5,5-dimethyl-2-hexanone, 3,3-dimethyl-2-heptanone, 3,4-dimethyl-2-heptanone, 3,5-dimethyl-2-heptanone, 3,6-dimethyl-2-heptanone, 4,4-dimethyl-2-heptanone, 4,5-dimethyl-2-heptanone, 4,6-dimethyl-2-heptanone, 5,5-dimethyl-2-heptanone, 5,6-dimethyl-2-heptanone, 6,6-dimethyl-2-heptanone, 3,3-dimethyl-2-octanone, 3,4-dimethyl-2-octanone, 3,5-dimethyl-2-octanone, 3,6-dimethyl-2-octanone, 3,7-dimethyl-2-octanone, 4,4-dimethyl-2-octanone, 4,5-dimethyl-2-octanone, 4,6-dimethyl-2-octanone, 4,7-dimethyl-2-octanone, 5,5-dimethyl-2-octanone, 5,6-dimethyl-2-octanone, 5,7-dimethyl-2-octanone, 6,6-dimethyl-2-octanone, 6,7-dimethyl-2-octanone, 7,7-dimethyl-2-octanone, 3,3-dimethyl-2-nonanone, 3,4-dimethyl-2-nonanone, 3,5-dimethyl-2-nonanone, 3,6-dimethyl-2-nonanone, 3,7-dimethyl-2-nonanone, 3,8-dimethyl-2-nonanone, 4,4-dimethyl-2-nonanone, 4,5-dimethyl-2-nonanone, 4,6-dimethyl-2-nonanone, 4,7-dimethyl-2-nonanone, 4,8-dimethyl-2-nonanone, 5,5-dimethyl-2-nonanone, 5,6-dimethyl-2-nonanone, 5,7-dimethyl-2-nonanone, 5,8-dimethyl-2-nonanone, 6,6-dimethyl-2-nonanone, 6,7-dimethyl-2-nonanone, 6,8-dimethyl-2-nonanone, 7,7-dimethyl-2-nonanone, 7,8-dimethyl-2-nonanone, 8,8-dimethyl-2-nonanone and the like. Even if optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the straight-chain or branched unsaturated ketones include, but are not particularly limited to, 4-hepten-2-one, 3-octen-2-one, 5-nonen-2-one, 5-decen-2-one, 5-undecen-2-one, 5-dodecen-2-one, 5-tridecen-2-one, 5-tetradecen-2-one, 5-pentadecen-2-one, 5-hexadecen-2-one, 5-heptadecen-2-one, 5-octadecen-2-one, 3-methyl-4-hexen-2-one, 4-methyl-4-hexen-2-one, 5-methyl-4-hexen-2-one, 3-methyl-4-hepten-2-one, 4-methyl-4-hepten-2-one, 5-methyl-4-hepten-2-one, 6-methyl-4-hepten-2-one, 6-methyl-5-hepten-2-one, 3-methyl-3-octen-2-one, 4-methyl-3-octen-2-one, 5-methyl-3-octen-2-one, 6-methyl-3-octen-2-one, 7-methyl-3-octen-2-one, 3-methyl-5-nonen-2-one, 4-methyl-5-nonen-2-one, 5-methyl-5-nonen-2-one, 6-methyl-5-nonen-2-one, 7-methyl-5-nonen-2-one, 8-methyl-5-nonen-2-one, 3-methyl-5-decen-2-one, 3-methyl-5-decen-2-one, 4-methyl-5-decen-2-one, 5-methyl-5-decen-2-one, 6-methyl-5-decen-2-one, 7-methyl-5-decen-2-one, 8-methyl-5-decen-2-one, 9-methyl-5-decen-2-one, 3,4-dimethyl-3-penten-2-one, 3,3-dimethyl-4-hexen-2-one, 3,4-dimethyl-4-hexen-2-one, 3,5-dimethyl-4-hexen-2-one, 4,5-dimethyl-4-hexen-2-one, 3,3-dimethyl-4-hepten-2-one, 3,4-dimethyl-4-hepten-2-one, 3,5- dimethyl-4-hepten-2-one, 3,6-dimethyl-4-hepten-2-one, 4,5-dimethyl-4-hepten-2-one, 4,6-dimethyl-4-hepten-2-one, 5,6-dimethyl-4-hepten-2-one, 6,6-dimethyl-4-hepten-2-one, 3,4-dimethyl-3-octen-2-one, 3,5-dimethyl-3-octen-2-one, 3,6-dimethyl-3-octen-2-one, 3,7-dimethyl-3-octen-2-one, 4,5-dimethyl-3-octen-2-one, 4,6-dimethyl-3-octen-2-one, 4,7-dimethyl-3-octen-2-one, 5,5-dimethyl-3-octen-2-one, 5,6-dimethyl-3-octen-2-one, 5,7-dimethyl-3-octen-2-one, 6,6-dimethyl-3-octen-2-one, 6,7-dimethyl-3-octen-2-one, 7,7-dimethyl-3-octen-2-one, 3,3-dimethyl-5-nonen-2-one, 3,4-dimethyl-5-nonen-2-one, 3,5-dimethyl-5-nonen-2-one, 3,6-dimethyl-5-nonen-2-one, 3,7-dimethyl-5-nonen-2-one, 3,8-dimethyl-5-nonen-2-one, 4,4-dimethyl-5-nonen-2-one, 4,5-dimethyl-5-nonen-2-one, 4,6-dimethyl-5-nonen-2-one, 4,7-dimethyl-5-nonen-2-one, 4,8-dimethyl-5-nonen-2-one, 5,6-dimethyl-5-nonen-2-one, 5,7-dimethyl-5-nonen-2-one, 5,8-dimethyl-5-nonen-2-one, 6,7-dimethyl-5-nonen-2-one, 6,8-dimethyl-5-nonen-2-one, 7,7-dimethyl-5-nonen-2-one, 7,8-dimethyl-5-nonen-2-one, 8,8-dimethyl-5-nonen-2-one and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the hydroxyl group-containing straight-chain or branched aldehydes include, but are not particularly limited to, 3-hydroxyheptanal, 3-hydroxyoctanal, 3-hydroxynonanal, 3-hydroxydecanal, 3-hydroxyundecanal, 3-hydroxidodecanal, 3-hydroxytridecanal, 3-hydroxytetradecanal, 3-hydroxypentadecanal, 3-hydroxyhexadecanal, 3-hydroxyheptadecanal, 3-hydroxyoctadecanal, 2-methyl-3-hydroxyhexanal, 3-methyl-3-hydroxyhexanal, 4-methyl-3-hydroxyhexanal, 5-methyl-3-hydroxyhexanal, 2-methyl-3-hydroxyheptanal, 3-methyl-3-hydroxyheptanal, 4-methyl-3-hydroxyheptanal, 5-methyl-3-hydroxyheptanal, 6-methyl-3-hydroxyheptanal, 2-methyl-3-hydroxyoctanal, 3-methyl-3-hydroxyoctanal, 4-methyl-3-hydroxyoctanal, 5-methyl-3-hydroxyoctanal, 6-methyl-3-hydroxyoctanal, 7-methyl-3-hydroxyoctanal, 2-methyl-3-hydroxynonanal, 3-methyl-3-hydroxynonanal, 4-methyl-3-hydroxynonanal, 5-methyl-3-hydroxynonanal, 6-methyl-3-hydroxynonanal, 7-methyl-3-hydroxynonanal, 8-methyl-3-hydroxynonanal, 2-methyl-3-hydroxydecanal, 2-methyl-3-hydroxydecanal, 3-methyl-3-hydroxydecanal, 3-methyl-3-hydroxydecanal, 4-methyl-3-hydroxydecanal, 5-methyl-3-hydroxydecanal, 6-methyl-3-hydroxydecanal, 7-methyl-3-hydroxydecanal, 8-methyl-3-hydroxydecanal, 9-methyl-3-hydroxydecanal, 2,3-dimethyl-3-hydroxypentanal, 2,4-dimethyl-3-hydroxypentanal, 2,2-dimethyl-3-hydroxypentanal, 3,4-dimethyl-3-hydroxypentanal, 4,4-dimethyl-3-hydroxypentanal, 2,2-dimethyl-3-hydroxyhexanal, 2,3-dimethyl-3-hydroxyhexanal, 2,4-dimethyl-3-hydroxyhexanal, 2,5-dimethyl-3-hydroxyhexanal, 3,4-dimethyl-3-hydroxyhexanal, 3,5-dimethyl-3-hydroxyhexanal, 4,4-dimethyl-3-hydroxyhexanal, 4,5-dimethyl-3-hydroxyhexanal, 5,5-dimethyl-3-hydroxyhexanal, 2,2-dimethyl-3-hydroxyheptanal, 2,3-dimethyl-3-hydroxyheptanal, 2,4-dimethyl-3-hydroxyheptanal, 2,5-dimethyl-3-hydroxyheptanal, 2,6-dimethyl-3-hydroxyheptanal, 3,4-dimethyl-3-hydroxyheptanal, 3,5-dimethyl-3-hydroxyheptanal, 3,6-dimethyl-3-hydroxyheptanal, 4,4-dimethyl-3-hydroxyheptanal, 4,5-dimethyl-3-hydroxyheptanal, 4,6-dimethyl-3-hydroxyheptanal, 5,5-dimethyl-3-hydroxyheptanal, 5,6-dimethyl-3-hydroxyheptanal, 6,6-dimethyl-3-hydroxyheptanal, 2,2-dimethyl-3-hydroxyoctanal, 2,3-dimethyl-3-hydroxyoctanal, 2,4-dimethyl-3-hydroxyoctanal, 2,5-dimethyl-3-hydroxyoctanal, 2,6-dimethyl-3-hydroxyoctanal, 2,7-dimethyl-3-hydroxyoctanal, 3,4-dimethyl-3-hydroxyoctanal, 3,5-dimethyl-3-hydroxyoctanal, 3,6-dimethyl-3-hydroxyoctanal, 3,7-dimethyl-3-hydroxyoctanal, 3,7-dimethyl-7-hydroxyoctanal, 4,4-dimethyl-3-hydroxyoctanal, 4,5-dimethyl-3-hydroxyoctanal, 4,6-dimethyl-3-hydroxyoctanal, 4,7-dimethyl-3-hydroxyoctanal, 5,5-dimethyl-3-hydroxyoctanal, 5,6-dimethyl-3-hydroxyoctanal, 5,7-dimethyl-3-hydroxyoctanal, 6,6-dimethyl-3-hydroxyoctanal, 6,7-dimethyl-3-hydroxyoctanal, 7,7-dimethyl-3-hydroxyoctanal, 2,2-dimethyl-3-hydroxynonanal, 2,3-dimethyl-3-hydroxynonanal, 2,4-dimethyl-3-hydroxynonanal, 2,5-dimethyl-3-hydroxynonanal, 2,6-dimethyl-3-hydroxynonanal, 2,7-dimethyl-3-hydroxynonanal, 2,8-dimethyl-3-hydroxynonanal, 3,4-dimethyl-3-hydroxynonanal, 3,5-dimethyl-3-hydroxynonanal, 3,6-dimethyl-3-hydroxynonanal, 3,7-dimethyl-3-hydroxynonanal, 3,8-dimethyl-3-hydroxynonanal, 4,4-dimethyl-3-hydroxynonanal, 4,5-dimethyl-3-hydroxynonanal, 4,6-dimethyl-3-hydroxynonanal, 4,7-dimethyl-3-hydroxynonanal, 4,8-dimethyl-3-hydroxynonanal, 5,5-dimethyl-3-hydroxynonanal, 5,6-dimethyl-3-hydroxynonanal, 5,7-dimethyl-3-hydroxynonanal, 5,8-dimethyl-3-hydroxynonanal, 6,6-dimethyl-3-hydroxynonanal, 6,7-dimethyl-3-hydroxynonanal, 6,8-dimethyl-3-hydroxynonanal, 7,7-dimethyl-3-hydroxynonanal, 7,8-dimethyl-3-hydroxynonanal, 8,8-dimethyl-3-hydroxynonanal and the like. Even if optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the ether group-containing straight-chain or branched aldehydes include, but are not particularly limited to, 3-methoxyheptanal, 3-methoxyoctanal, 3-methoxynonanal, 3-methoxydecanal, 3-methoxyundecanal, 3-methoxydodecanal, 3-methoxytridecanal, 3-methoxytetradecanal, 3-methoxypentadecanal, 3-methoxyhexadecanal, 3-methoxyheptadecanal, 2-methyl-3-methoxyhexanal, 3-methyl-3-methoxyhexanal, 4-methyl-3-methoxyhexanal, 5-methyl-3-methoxyhexanal, 2-methyl-3-methoxyheptanal, 3-methyl-3-methoxyheptanal, 4-methyl-3-methoxyheptanal, 5-methyl-3-methoxyheptanal, 6-methyl-3-methoxyheptanal, 2-methyl-3-methoxyoctanal, 3-methyl-3-methoxyoctanal, 4-methyl-3-methoxyoctanal, 5-methyl-3-methoxyoctanal, 6-methyl-3-methoxyoctanal, 7-methyl-3-methoxyoctanal, 2-methyl-3-methoxynonanal, 3-methyl-3-methoxynonanal, 4-methyl-3-methoxynonanal, 5-methyl-3-methoxynonanal, 6-methyl-3-methoxynonanal, 7-methyl-3-methoxynonanal, 8-methyl-3-methoxynonanal, 2,3-dimethyl-3-methoxypentanal, 2,4-dimethyl-3-methoxypentanal, 2,2-dimethyl-3-methoxypentanal, 3,4-dimethyl-3-methoxypentanal, 4,4-dimethyl-3-methoxypentanal, 2,2-dimethyl-3-methoxyhexanal, 2,3-dimethyl-3-methoxyhexanal, 2,4-dimethyl-3-methoxyhexanal, 2,5-dimethyl-3-methoxyhexanal, 3,4-dimethyl-3-methoxyhexanal, 3,5-dimethyl-3-methoxyhexanal, 4,4-dimethyl-3-methoxyhexanal, 4,5-dimethyl-3-methoxyhexanal, 5,5-dimethyl-3-methoxyhexanal, 2,2-dimethyl-3- methoxyheptanal, 2,3-dimethyl-3-methoxyheptanal, 2,4-dimethyl-3-methoxyheptanal, 2,5-dimethyl-3-methoxyheptanal, 2,6-dimethyl-3-methoxyheptanal, 3,4-dimethyl-3-methoxyheptanal, 3,5-dimethyl-3-methoxyheptanal, 3,6-dimethyl-3-methoxyheptanal, 4,4-dimethyl-3-methoxyheptanal, 4,5-dimethyl-3-methoxyheptanal, 4,6-dimethyl-3-methoxyheptanal, 5,5-dimethyl-3-methoxyheptanal, 5,6-dimethyl-3-methoxyheptanal, 6,6-dimethyl-3-methoxyheptanal, 2,2-dimethyl-3-methoxyoctanal, 2,3-dimethyl-3-methoxyoctanal, 2,4-dimethyl-3-methoxyoctanal, 2,5-dimethyl-3-methoxyoctanal, 2,6-dimethyl-3-methoxyoctanal, 2,7-dimethyl-3-methoxyoctanal, 3,4-dimethyl-3-methoxyoctanal, 3,5-dimethyl-3-methoxyoctanal, 3,6-dimethyl-3-methoxyoctanal, 3,7-dimethyl-3-methoxyoctanal, 3,7-dimethyl-7-methoxyoctanal, 4,4-dimethyl-3-methoxyoctanal, 4,5-dimethyl-3-methoxyoctanal, 4,6-dimethyl-3-methoxyoctanal, 4,7-dimethyl-3-methoxyoctanal, 5,5-dimethyl-3-methoxyoctanal, 5,6-dimethyl-3-methoxyoctanal, 5,7-dimethyl-3-methoxyoctanal, 6,6-dimethyl-3-methoxyoctanal, 6,7-dimethyl-3-methoxyoctanal, 7,7-dimethyl-3-methoxyoctanal, and the like. Even if optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the hydroxyl group-containing straight-chain or branched ketones include, but are not particularly limited to, 3-hydroxy-2-heptanone, 3-hydroxy-2-octanone, 3-hydroxy-2-nonanone, 3-hydroxy-2-decanone, 3-hydroxy-2-undecanone, 3-hydroxy-2-dodecanone, 3-hydroxy-2-tridecanone, 3-hydroxy-2-tetradecanone, 3-hydroxy-2-pentadecanone, 3-hydroxy-2-hexadecanone, 3-hydroxy-2-heptadecanone, 3-hydroxy-2-octadecanone, 3-methyl-3-hydroxy-2-hexanone, 4-methyl-3-hydroxy-2-hexanone, 5-methyl-3-hydroxy-2-hexanone, 3-methyl-3-hydroxy-2-heptanone, 4-methyl-3-hydroxy-2-heptanone, 5-methyl-3-hydroxy-2-heptanone, 6-methyl-3-hydroxy-2-heptanone, 3-methyl-3-hydroxy-2-octanone, 4-methyl-3-hydroxy-2-octanone, 5-methyl-3-hydroxy-2-octanone, 6-methyl-3-hydroxy-2-octanone, 7-methyl-3-hydroxy-2-octanone, 3-methyl-3-hydroxy-2-nonanone, 4-methyl-3-hydroxy-2-nonanone, 5-methyl-3-hydroxy-2-nonanone, 6-methyl-3-hydroxy-2-nonanone, 7-methyl-3-hydroxy-2-nonanone, 8-methyl-3-hydroxy-2-nonanone, 3-methyl-3-hydroxy-2-decanone, 4-methyl-3-hydroxy-2-decanone, 5-methyl-3-hydroxy-2-decanone, 6-methyl-3-hydroxy-2-decanone, 7-methyl-3-hydroxy-2-decanone, 8-methyl-3-hydroxy-2-decanone, 9-methyl-3-hydroxy-2-decanone, 3,4-dimethyl-3-hydroxy-2-pentanone, 4,4-dimethyl-3-hydroxy-2-pentanone, 3,4-dimethyl-3-hydroxy-2-hexanone, 3,5-dimethyl-3-hydroxy-2-hexanone, 4,4-dimethyl-3-hydroxy-2-hexanone, 4,5-dimethyl-3-hydroxy-2-hexanone, 5,5-dimethyl-3-hydroxy-2-hexanone, 3,4-dimethyl-3-hydroxy-2-heptanone, 3,5-dimethyl-3-hydroxy-2-heptanone, 3,6-dimethyl-3-hydroxy-2-heptanone, 4,4-dimethyl-3-hydroxy-2-heptanone, 4,5-dimethyl-3-hydroxy-2-heptanone, 4,6-dimethyl-3-hydroxy-2-heptanone, 5,5-dimethyl-3-hydroxy-2-heptanone, 5,6-dimethyl-3-hydroxy-2-heptanone, 6,6-dimethyl-3-hydroxy-2-heptanone, 3,4-dimethyl-3-hydroxy-2-octanone, 3,5-dimethyl-3-hydroxy-2-octanone, 3,6-dimethyl-3-hydroxy-2-octanone, 3,7-dimethyl-3-hydroxy-2-octanone, 4,4-dimethyl-3-hydroxy-2-octanone, 4,5-dimethyl-3-hydroxy-2-octanone, 4,6-dimethyl-3-hydroxy-2-octanone, 4,7-dimethyl-3-hydroxy-2-octanone, 5,5-dimethyl-3-hydroxy-2-octanone, 5,6-dimethyl-3-hydroxy-2-octanone, 5,7-dimethyl-3-hydroxy-2-octanone, 6,6-dimethyl-3-hydroxy-2-octanone, 6,7-dimethyl-3-hydroxy-2-octanone, 7,7-dimethyl-3-hydroxy-2-octanone, 3,4-dimethyl-3-hydroxy-2-nonanone, 3,5-dimethyl-3-hydroxy-2-nonanone, 3,6-dimethyl-3-hydroxy-2-nonanone, 3,7-dimethyl-3-hydroxy-2-nonanone, 3,8-dimethyl-3-hydroxy-2-nonanone, 4,4-dimethyl-3-hydroxy-2-nonanone, 4,5-dimethyl-3-hydroxy-2-nonanone, 4,6-dimethyl-3-hydroxy-2-nonanone, 4,7-dimethyl-3-hydroxy-2-nonanone, 4,8-dimethyl-3-hydroxy-2-nonanone, 5,5-dimethyl-3-hydroxy-2-nonanone, 5,6-dimethyl-3-hydroxy-2-nonanone, 5,7-dimethyl-3-hydroxy-2-nonanone, 5,8-dimethyl-3-hydroxy-2-nonanone, 6,6-dimethyl-3-hydroxy-2-nonanone, 6,7-dimethyl-3-hydroxy-2-nonanone, 6,8-dimethyl-3-hydroxy-2-nonanone, 7,7-dimethyl-3-hydroxy-2-nonanone, 7,8-dimethyl-3-hydroxy-2-nonanone, 8,8-dimethyl-3-hydroxy-2-nonanone and the like. Even if optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the ether group-containing straight-chain or branched ketones include, but are not particularly limited to, 3-methoxy-2-heptanone, 3-methoxy-2-octanone, 3-methoxy-2-nonanone, 3-methoxy-2-decanone, 3-methoxy-2-undecanone, 3-methoxy-2-dodecanone, 3-methoxy-2-tridecanone, 3-methoxy-2-tetradecanone, 3-methoxy-2-pentadecanone, 3-methoxy-2-hexadecanone, 3-methoxy-2-heptadecanone, 3-methyl-3-methoxy-2-hexanone, 4-methyl-3-methoxy-2-hexanone, 5-methyl-3-methoxy-2-hexanone, 3-methyl-3-methoxy-2-heptanone, 4-methyl-3-methoxy-2-heptanone, 5-methyl-3-methoxy-2-heptanone, 6-methyl-3-methoxy-2-heptanone, 3-methyl-3-methoxy-2-octanone, 4-methyl-3-methoxy-2-octanone, 5-methyl-3-methoxy-2-octanone, 6-methyl-3-methoxy-2-octanone, 7-methyl-3-methoxy-2-octanone, 3-methyl-3-methoxy-2-nonanone, 4-methyl-3-methoxy-2-nonanone, 5-methyl-3-methoxy-2-nonanone, 6-methyl-3-methoxy-2-nonanone, 7-methyl-3-methoxy-2-nonanone, 8-methyl-3-methoxy-2-nonanone, 3,4-dimethyl-3-methoxy-2-pentanone, 4,4-dimethyl-3-methoxy-2-pentanone, 3,4-dimethyl-3-methoxy-2-hexanone, 3,5-dimethyl-3-methoxy-2-hexanone, 4,4-dimethyl-3-methoxy-2-hexanone, 4,5-dimethyl-3-methoxy-2-hexanone, 5,5-dimethyl-3-methoxy-2-hexanone, 3,4-dimethyl-3-methoxy-2-heptanone, 3,5-dimethyl-3-methoxy-2-heptanone, 3,6-dimethyl-3-methoxy-2-heptanone, 4,4-dimethyl-3-methoxy-2-heptanone, 4,5-dimethyl-3-methoxy-2-heptanone, 4,6-dimethyl-3-methoxy-2-heptanone, 5,5-dimethyl-3-methoxy-2-heptanone, 5,6-dimethyl-3-methoxy-2-heptanone, 6,6-dimethyl-3-methoxy-2-heptanone, 3,4-dimethyl-3-methoxy-2-octanone, 3,5-dimethyl-3-methoxy-2-octanone, 3,6-dimethyl-3-methoxy-2-octanone, 3,7-dimethyl-3-methoxy-2-octanone, 4,4-dimethyl-3-methoxy-2-octanone, 4,5-dimethyl-3-methoxy-2-octanone, 4,6-dimethyl-3-methoxy-2-octanone, 4,7-dimethyl-3-methoxy-2-octanone, 5,5-dimethyl-3-methoxy-2-octanone, 5,6-dimethyl-3-methoxy-2-octanone, 5,7-dimethyl-3-methoxy-2-octanone, 6,6- dimethyl-3-methoxy-2-octanone, 6,7-dimethyl-3-methoxy-2-octanone, 7,7-dimethyl-3-methoxy-2-octanone, and the like. Even if optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of hydroxyl group-containing straight-chain or branched unsaturated aldehydes include, but are not particularly limited to, 5-hydroxy-2-heptenal, 5-hydroxy-2-octenal, 5-hydroxy-2-nonenal, 5-hydroxy-2-decenal, 5-hydroxy-2-undecenal, 5-hydroxy-2-dodecenal, 5-hydroxy-2-tridecenal, 5-hydroxy-2-tetradecenal, 5-hydroxy-2-pentadecenal, 5-hydroxy-2-hexadecenal, 5-hydroxy-2-heptadecenal, 5-hydroxy-2-octadecenal, 2-methyl-5-hydroxy-2-hexenal, 3-methyl-5-hydroxy-2-hexenal, 4-methyl-5-hydroxy-2-hexenal, 5-methyl-5-hydroxy-2-hexenal, 2-methyl-5-hydroxy-2-heptenal, 3-methyl-5-hydroxy-2-heptenal, 4-methyl-5-hydroxy-2-heptenal, 5-methyl-5-hydroxy-2-heptenal, 6-methyl-5-hydroxy-2-heptenal, 2-methyl-5-hydroxy-2-octenal, 3-methyl-5-hydroxy-2-octenal, 4-methyl-5-hydroxy-2-octenal, 5-methyl-5-hydroxy-2-octenal, 6-methyl-5-hydroxy-2-octenal, 7-methyl-5-hydroxy-2-octenal, 2-methyl-5-hydroxy-2-nonenal, 3-methyl-5-hydroxy-2-nonenal, 4-methyl-5-hydroxy-2-nonenal, 5-methyl-5-hydroxy-2-nonenal, 6-methyl-5-hydroxy-2-nonenal, 7-methyl-5-hydroxy-2-nonenal, 8-methyl-5-hydroxy-2-nonenal, 2-methyl-5-hydroxy-2-decenal, 2-methyl-5-hydroxy-2-decenal, 3-methyl-5-hydroxy-2-decenal, 3-methyl-5-hydroxy-2-decenal, 4-methyl-5-hydroxy-2-decenal, 5-methyl-5-hydroxy-2-decenal, 6-methyl-5-hydroxy-2-decenal, 7-methyl-5-hydroxy-2-decenal, 8-methyl-5-hydroxy-2-decenal, 9-methyl-5-hydroxy-2-decenal, 2,3-dimethyl-4-hydroxy-2-pentenal, 2,4-dimethyl-4-hydroxy-2-pentenal, 3,4-dimethyl-4-hydroxy-2-pentenal, 2,3-dimethyl-5-hydroxy-2-hexenal, 2,4-dimethyl-5-hydroxy-2-hexenal, 2,5-dimethyl-5-hydroxy-2-hexenal, 3,4-dimethyl-5-hydroxy-2-hexenal, 3,5-dimethyl-5-hydroxy-2-hexenal, 4,4-dimethyl-5-hydroxy-2-hexenal, 4,5-dimethyl-5-hydroxy-2-hexenal, 2,3-dimethyl-5-hydroxy-2-heptenal, 2,4-dimethyl-5-hydroxy-2-heptenal, 2,5-dimethyl-5-hydroxy-2-heptenal, 2,6-dimethyl-5-hydroxy-2-heptenal, 3,4-dimethyl-5-hydroxy-2-heptenal, 3,5-dimethyl-5-hydroxy-2-heptenal, 3,6-dimethyl-5-hydroxy-2-heptenal, 4,4-dimethyl-5-hydroxy-2-heptenal, 4,5-dimethyl-5-hydroxy-2-heptenal, 4,6-dimethyl-5-hydroxy-2-heptenal, 5,6-dimethyl-5-hydroxy-2-heptenal, 6,6-dimethyl-5-hydroxy-2-heptenal, 2,3-dimethyl-5-hydroxy-2-octenal, 2,4-dimethyl-5-hydroxy-2-octenal, 2,5-dimethyl-5-hydroxy-2-octenal, 2,6-dimethyl-5-hydroxy-2-octenal, 2,7-dimethyl-5-hydroxy-2-octenal, 3,4-dimethyl-5-hydroxy-2-octenal, 3,5-dimethyl-5-hydroxy-2-octenal, 3,6-dimethyl-5-hydroxy-2-octenal, 3,7-dimethyl-5-hydroxy-2-octenal, 4,4-dimethyl-5-hydroxy-2-octenal, 4,5-dimethyl-5-hydroxy-2-octenal, 4,6-dimethyl-5-hydroxy-2-octenal, 4,7-dimethyl-5-hydroxy-2-octenal, 5,6-dimethyl-5-hydroxy-2-octenal, 5,7-dimethyl-5-hydroxy-2-octenal, 6,6-dimethyl-5-hydroxy-2-octenal, 6,7-dimethyl-5-hydroxy-2-octenal, 7,7-dimethyl-5-hydroxy-2-octenal, 2,3-dimethyl-5-hydroxy-2-nonenal, 2,4-dimethyl-5-hydroxy-2-nonenal, 2,5-dimethyl-5-hydroxy-2-nonenal, 2,6-dimethyl-5-hydroxy-2-nonenal, 2,7-dimethyl-5-hydroxy-2-nonenal, 2,8-dimethyl-5-hydroxy-2-nonenal, 3,4-dimethyl-5-hydroxy-2-nonenal, 3,5-dimethyl-5-hydroxy-2-nonenal, 3,6-dimethyl-5-hydroxy-2-nonenal, 3,7-dimethyl-5-hydroxy-2-nonenal, 3,8-dimethyl-5-hydroxy-2-nonenal, 4,4-dimethyl-5-hydroxy-2-nonenal, 4,5-dimethyl-5-hydroxy-2-nonenal, 4,6-dimethyl-5-hydroxy-2-nonenal, 4,7-dimethyl-5-hydroxy-2-nonenal, 4,8-dimethyl-5-hydroxy-2-nonenal, 5,6-dimethyl-5-hydroxy-2-nonenal, 5,7-dimethyl-5-hydroxy-2-nonenal, 5,8-dimethyl-5-hydroxy-2-nonenal, 6,6-dimethyl-5-hydroxy-2-nonenal, 6,7-dimethyl-5-hydroxy-2-nonenal, 6,8-dimethyl-5-hydroxy-2-nonenal, 7,7-dimethyl-5-hydroxy-2-nonenal, 7,8-dimethyl-5-hydroxy-2-nonenal, 8,8-dimethyl-5-hydroxy-2-nonenal, (unconjugated) 5-hydroxy-3-heptenal, 5-hydroxy-3-octenal, 5-hydroxy-3-nonenal, 5-hydroxy-3-decenal, 5-hydroxy-3-undecenal, 2-methyl-5-hydroxy-3-hexenal, 3-methyl-5-hydroxy-3-hexenal, 4-methyl-5-hydroxy-3-hexenal, 5-methyl-5-hydroxy-3-hexenal, 2-methyl-5-hydroxy-3-heptenal, 3-methyl-5-hydroxy-3-heptenal, 4-methyl-5-hydroxy-3-heptenal, 5-methyl-5-hydroxy-3-heptenal, 6-methyl-5-hydroxy-3-heptenal, 2-methyl-5-hydroxy-3-octenal, 3-methyl-5-hydroxy-3-octenal, 4-methyl-5-hydroxy-3-octenal, 5-methyl-5-hydroxy-3-octenal, 6-methyl-5-hydroxy-3-octenal, 7-methyl-5-hydroxy-3-octenal, 2-methyl-5-hydroxy-3-nonenal, 3-methyl-5-hydroxy-3-nonenal, 4-methyl-5-hydroxy-3-nonenal, 5-methyl-5-hydroxy-3-nonenal, 6-methyl-5-hydroxy-3-nonenal, 7-methyl-5-hydroxy-3-nonenal, 8-methyl-5-hydroxy-3-nonenal, 2-methyl-5-hydroxy-3-decenal, 2-methyl-5-hydroxy-3-decenal, 3-methyl-5-hydroxy-3-decenal, 3-methyl-5-hydroxy-3-decenal, 4-methyl-5-hydroxy-3-decenal, 5-methyl-5-hydroxy-3-decenal, 6-methyl-5-hydroxy-3-decenal, 7-methyl-5-hydroxy-3-decenal, 8-methyl-5-hydroxy-3-decenal, 9-methyl-5-hydroxy-3-decenal and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the ether group-containing straight-chain or branched unsaturated aldehyde include, but are not particularly limited to, 5-methoxy-2-heptenal, 5-methoxy-2-octenal, 5-methoxy-2-nonenal, 5-methoxy-2-decenal, 5-methoxy-2-undecenal, 5-methoxy-2-dodecenal, 5-methoxy-2-tridecenal, 5-methoxy-2-tetradecenal, 5-methoxy-2-pentadecenal, 5-methoxy-2-hexadecenal, 5-methoxy-2-heptadecenal, 5-methoxy-2-octadecenal, 2-methyl-5-methoxy-2-hexenal, 3-methyl-5-methoxy-2-hexenal, 4-methyl-5-methoxy-2-hexenal, 5-methyl-5-methoxy-2-hexenal, 2-methyl-5-methoxy-2-heptenal, 3-methyl-5-methoxy-2-heptenal, 4-methyl-5-methoxy-2-heptenal, 5-methyl-5-methoxy-2-heptenal, 6-methyl-5-methoxy-2-heptenal, 2-methyl-5-methoxy-2-octenal, 3-methyl-5-methoxy-2-octenal, 4-methyl-5-methoxy-2-octenal, 5-methyl-5-methoxy-2-octenal, 6-methyl-5-methoxy-2-octenal, 7-methyl-5-methoxy-2-octenal, 2-methyl-5-methoxy-2-nonenal, 3-methyl-5-methoxy-2-nonenal, 4-methyl-5-methoxy-2-nonenal, 5-methyl-5-methoxy-2-nonenal, 6-methyl-5-methoxy-2-nonenal, 7-methyl-5-methoxy-2-nonenal, 8-methyl-5-methoxy-2-nonenal, 2-methyl-5-methoxy-2-decenal, 2-methyl-5-methoxy-2-decenal, 3-methyl-5-methoxy-2-decenal, 3-methyl-5-methoxy-2-decenal, 4-methyl-5-methoxy-2-decenal, 5-methyl-5-methoxy-2-decenal, 6-methyl-5-methoxy-2-decenal, 7-methyl-5-methoxy-2-decenal, 8-methyl-5-methoxy-2-decenal, 9-methyl-5-methoxy-2-decenal, 2,3-dimethyl-4-methoxy-2-pentenal, 2,4-dimethyl-4-methoxy-2-pentenal, 3,4-dimethyl-4-methoxy-2-pentenal, 2,3-dimethyl-5-methoxy-2-hexenal, 2,4-dimethyl-5-methoxy-2-hexenal, 2,5-dimethyl-5-methoxy-2-hexenal, 3,4-dimethyl-5-methoxy-2-hexenal, 3,5-dimethyl-5-methoxy-2-hexenal, 4,4-dimethyl-5-methoxy-2-hexenal, 4,5-dimethyl-5-methoxy-2-hexenal, 2,3-dimethyl-5-methoxy-2-heptenal, 2,4-dimethyl-5-methoxy-2-heptenal, 2,5-dimethyl-5-methoxy-2-heptenal, 2,6-dimethyl-5-methoxy-2-heptenal, 3,4-dimethyl-5-methoxy-2-heptenal, 3,5-dimethyl-5-methoxy-2-heptenal, 3,6-dimethyl-5-methoxy-2-heptenal, 4,4-dimethyl-5-methoxy-2-heptenal, 4,5-dimethyl-5-methoxy-2-heptenal, 4,6-dimethyl-5-methoxy-2-heptenal, 5,6-dimethyl-5-methoxy-2-heptenal, 6,6-dimethyl-5-methoxy-2-heptenal, 2,3-dimethyl-5-methoxy-2-octenal, 2,4-dimethyl-5-methoxy-2-octenal, 2,5-dimethyl-5-methoxy-2-octenal, 2,6-dimethyl-5-methoxy-2-octenal, 2,7-dimethyl-5-methoxy-2-octenal, 3,4-dimethyl-5-methoxy-2-octenal, 3,5-dimethyl-5-methoxy-2-octenal, 3,6-dimethyl-5-methoxy-2-octenal, 3,7-dimethyl-5-methoxy-2-octenal, 4,4-dimethyl-5-methoxy-2-octenal, 4,5-dimethyl-5-methoxy-2-octenal, 4,6-dimethyl-5-methoxy-2-octenal, 4,7-dimethyl-5-methoxy-2-octenal, 5,6-dimethyl-5-methoxy-2-octenal, 5,7-dimethyl-5-methoxy-2-octenal, 6,6-dimethyl-5-methoxy-2-octenal, 6,7-dimethyl-5-methoxy-2-octenal, 7,7-dimethyl-5-methoxy-2-octenal, 2,3-dimethyl-5-methoxy-2-nonenal, 2,4-dimethyl-5-methoxy-2-nonenal, 2,5-dimethyl-5-methoxy-2-nonenal, 2,6-dimethyl-5-methoxy-2-nonenal, 2,7-dimethyl-5-methoxy-2-nonenal, 2,8-dimethyl-5-methoxy-2-nonenal, 3,4-dimethyl-5-methoxy-2-nonenal, 3,5-dimethyl-5-methoxy-2-nonenal, 3,6-dimethyl-5-methoxy-2-nonenal, 3,7-dimethyl-5-methoxy-2-nonenal, 3,8-dimethyl-5-methoxy-2-nonenal, 4,4-dimethyl-5-methoxy-2-nonenal, 4,5-dimethyl-5-methoxy-2-nonenal, 4,6-dimethyl-5-methoxy-2-nonenal, 4,7-dimethyl-5-methoxy-2-nonenal, 4,8-dimethyl-5-methoxy-2-nonenal, 5,6-dimethyl-5-methoxy-2-nonenal, 5,7-dimethyl-5-methoxy-2-nonenal, 5,8-dimethyl-5-methoxy-2-nonenal, 6,6-dimethyl-5-methoxy-2-nonenal, 6,7-dimethyl-5-methoxy-2-nonenal, 6,8-dimethyl-5-methoxy-2-nonenal, 7,7-dimethyl-5-methoxy-2-nonenal, 7,8-dimethyl-5-methoxy-2-nonenal, 8,8-dimethyl-5-methoxy-2-nonenal, 5-methoxy-3-heptenal, 5-methoxy-3-octenal, 5-methoxy-3-nonenal, 5-methoxy-3-decenal, 5-methoxy-3-undecenal, 2-methyl-5-methoxy-3-hexenal, 3-methyl-5-methoxy-3-hexenal, 4-methyl-5-methoxy-3-hexenal, 5-methyl-5-methoxy-3-hexenal, 2-methyl-5-methoxy-3-heptenal, 3-methyl-5-methoxy-3-heptenal, 4-methyl-5-methoxy-3-heptenal, 5-methyl-5-methoxy-3-heptenal, 6-methyl-5-methoxy-3-heptenal, 2-methyl-5-methoxy-3-octenal, 3-methyl-5-methoxy-3-octenal, 4-methyl-5-methoxy-3-octenal, 5-methyl-5-methoxy-3-octenal, 6-methyl-5-methoxy-3-octenal, 7-methyl-5-methoxy-3-octenal, 2-methyl-5-methoxy-3-nonenal, 3-methyl-5-methoxy-3-nonenal, 4-methyl-5-methoxy-3-nonenal, 5-methyl-5-methoxy-3-nonenal, 6-methyl-5-methoxy-3-nonenal, 7-methyl-5-methoxy-3-nonenal, 8-methyl-5-methoxy-3-nonenal, 2-methyl-5-methoxy-3-decenal, 3-methyl-5-methoxy-3-decenal, 4-methyl-5-methoxy-3-decenal, 5-methyl-5-methoxy-3-decenal, 6-methyl-5-methoxy-3-decenal, 7-methyl-5-methoxy-3-decenal, 8-methyl-5-methoxy-3-decenal, 9-methyl-5-methoxy-3-decenal, and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the hydroxyl group-containing straight-chain or branched unsaturated ketones include, but are not particularly limited to, 5-hydroxy-3-hexen-2-one, 5-hydroxy-3-hepten-2-one, 5-hydroxy-3-octen-2-one, 5-hydroxy-3-nonen-2-one, 5-hydroxy-3-decen-2-one, 5-hydroxy-3-undecen-2-one, 5-hydroxy-2-dodecen-2-one, 5-hydroxy-2-tridecen-2-one, 5-hydroxy-2-tetradecen-2-one, 5-hydroxy-2-pentadecen-2-one, 5-hydroxy-2-hexadecen-2-one, 5-hydroxy-2-heptadecen-2-one, 5-hydroxy-2-octadecen-2-one, 3-methyl-5-hydroxy-3-hexen-2-one, 4-methyl-5-hydroxy-3-hexen-2-one, 5-methyl-5-hydroxy-3-hexen-2-one, 3-methyl-5-hydroxy-3-hepten-2-one, 4-methyl-5-hydroxy-3-hepten-2-one, 5-methyl-5-hydroxy-3-hepten-2-one, 6-methyl-5-hydroxy-3-hepten-2-one, 3-methyl-5-hydroxy-3-octen-2-one, 4-methyl-5-hydroxy-3-octen-2-one, 5-methyl-5-hydroxy-3-octen-2-one, 6-methyl-5-hydroxy-3-octen-2-one, 7-methyl-5-hydroxy-3-octen-2-one, 3-methyl-5-hydroxy-3-nonen-2-one, 4-methyl-5-hydroxy-3-nonen-2-one, 5-methyl-5-hydroxy-3-nonen-2-one, 6-methyl-5-hydroxy-3-nonen-2-one, 7-methyl-5-hydroxy-3-nonen-2-one, 8-methyl-5-hydroxy-3-nonen-2-one, 3-methyl-5-hydroxy-3-decen-2-one, 4-methyl-5-hydroxy-3-decen-2-one, 5-methyl-5-hydroxy-3-decen-2-one, 6-methyl-5-hydroxy-3-decen-2-one, 7-methyl-5-hydroxy-3-decen-2-one, 8-methyl-5-hydroxy-3-decen-2-one, 9-methyl-5-hydroxy-3-decen-2-one, 3,4-dimethyl-4-hydroxy-3-penten-2-one, 3,4-dimethyl-5-hydroxy-3-hexen-2-one, 3,5-dimethyl-5-hydroxy-3-hexen-2-one, 4,5-dimethyl-5-hydroxy-3-hexen-2-one, 3,4-dimethyl-5-hydroxy-3-hepten-2-one, 3,5-dimethyl-5-hydroxy-3-hepten-2-one, 3,6-dimethyl-5-hydroxy-3-hepten-2-one, 4,5-dimethyl-5-hydroxy-3-heptene-2-one, 4,6-dimethyl-5-hydroxy-3-hepten-2-one, 5,6-dimethyl-5-hydroxy-3-hepten-2-one, 6,6-dimethyl-5-hydroxy-3-hepten-2-one, 3,4-dimethyl-5-hydroxy-3-octen-2-one, 3,5-dimethyl-5-hydroxy-3-octen-2-one, 3,6-dimethyl-5-hydroxy-3-octen-2-one, 3,7-dimethyl-5-hydroxy-3-octen-2-one, 4,5-dimethyl-5-hydroxy-3-octen-2-one, 4,6-dimethyl-5-hydroxy-3-octen-2-one, 4,7-dimethyl-5-hydroxy-3-octen-2-one, 5,6-dimethyl-5-hydroxy-3-octen-2-one, 5,7-dimethyl-5-hydroxy-3-octen-2-one, 6,6-dimethyl-5-hydroxy-3-octen-2-one, 6,7-dimethyl-5-hydroxy-3-octen-2-one, 7,7-dimethyl-5-hydroxy-3-octen-2-one, 3,4-dimethyl-5-hydroxy-3-nonen-2-one, 3,5-dimethyl-5-hydroxy-3-nonen-2-one, 3,6-dimethyl-5-hydroxy-3-nonen-2-one, 3,7-dimethyl-5-hydroxy-3-nonen-2-one, 3,8-dimethyl-5-hydroxy-3-nonene-2-one, 4,5-dimethyl-5-hydroxy-3-nonen-2-one, 4,6-dimethyl-5-hydroxy-3-nonen-2-one, 4,7-dimethyl-5-hydroxy-3-nonen-2-one, 4,8-dimethyl-5-hydroxy-3-nonen-2-one, 5,6-dimethyl-5-hydroxy-3-nonen-2-one, 5,7-dimethyl-5-hydroxy-3-nonen-2-one, 5,8-dimethyl-5-hydroxy-3-nonen-2-one, 6,6-dimethyl-5-hydroxy-3-nonen-2-one, 6,7-dimethyl-5-hydroxy-3-nonen-2-one, 6,8-dimethyl-5-hydroxy-3-nonen-2-one, 7,7-dimethyl-5-hydroxy-3-nonen-2-one, 7,8-dimethyl-5-hydroxy-3-nonen-2-one, 8,8-dimethyl-5-hydroxy-3-nonen-2-one and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the ether group-containing straight-chain or branched unsaturated ketones include, but are not particularly limited to, 5-methoxy-3-hepten-2-one, 5-methoxy-3-octen-2-one, 5-methoxy-3-nonen-2-one, 5-methoxy-3-decen-2-one, 5-methoxy-2-undecenone, 5-methoxy-2-dodecenone, 5-methoxy-2-tridecenone, 5-methoxy-2-tetradecenone, 5-methoxy-2-pentadecenone, 5-methoxy-2-hexadecenone, 5-methoxy-2-heptadecenone, 3-methyl-5-methoxy-3-hexen-2-one, 4-methyl-5-methoxy-3-hexen-2-one, 5-methyl-5-methoxy-3-hexen-2-one, 3-methyl-5-methoxy-3-hepten-2-one, 4-methyl-5-methoxy-3-hepten-2-one, 5-methyl-5-methoxy-3-hepten-2-one, 6-methyl-5-methoxy-3-hepten-2-one, 3-methyl-5-methoxy-3-octen-2-one, 4-methyl-5-methoxy-3-octen-2-one, 5-methyl-5-methoxy-3-octen-2-one, 6-methyl-5-methoxy-3-octen-2-one, 7-methyl-5-methoxy-3-octen-2-one, 3-methyl-5-methoxy-3-nonen-2-one, 4-methyl-5-methoxy-3-nonen-2-one, 5-methyl-5-methoxy-3-nonen-2-one, 6-methyl-5-methoxy-3-nonen-2-one, 7-methyl-5-methoxy-3-nonen-2-one, 8-methyl-5-methoxy-3-nonen-2-one, 3-methyl-5-methoxy-3-decen-2-one, 3-methyl-5-methoxy-3-decen-2-one, 4-methyl-5-methoxy-3-decen-2-one, 5-methyl-5-methoxy-3-decen-2-one, 6-methyl-5-methoxy-3-decen-2-one, 7-methyl-5-methoxy-3-decen-2-one, 8-methyl-5-methoxy-3-decen-2-one, 9-methyl-5-methoxy-3-decen-2-one, 3,4-dimethyl-4-methoxy-3-penten-2-one, 3,4-dimethyl-5-methoxy-3-hexen-2-one, 3,5-dimethyl-5-methoxy-3-hexen-2-one, 4,5-dimethyl-5-methoxy-3-hexen-2-one, 3,4-dimethyl-5-methoxy-3-hepten-2-one, 3,5-dimethyl-5-methoxy-3-hepten-2-one, 3,6-dimethyl-5-methoxy-3-hepten-2-one, 4,5-dimethyl-5-methoxy-3-hepten-2-one, 4,6-dimethyl-5-methoxy-3-hepten-2-one, 5,6-dimethyl-5-methoxy-3-hepten-2-one, 6,6-dimethyl-5-methoxy-3-hepten-2-one, 3,4-dimethyl-5-methoxy-3-octen-2-one, 3,5-dimethyl-5-methoxy-3-octen-2-one, 3,6-dimethyl-5-methoxy-3-octen-2-one, 3,7-dimethyl-5-methoxy-3-octen-2-one, 4,5-dimethyl-5-methoxy-3-octen-2-one, 4,6-dimethyl-5-methoxy-3-octen-2-one, 4,7-dimethyl-5-methoxy-3-octen-2-one, 5,6-dimethyl-5-methoxy-3-octen-2-one, 5,7-dimethyl-5-methoxy-3-octen-2-one, 6,6-dimethyl-5-methoxy-3-octen-2-one, 6,7-dimethyl-5-methoxy-3-octen-2-one, 7,7-dimethyl-5-methoxy-3-octen-2-one, 3,4-dimethyl-5-methoxy-3-nonen-2-one, 3,5-dimethyl-5-methoxy-3-nonen-2-one, 3,6-dimethyl-5-methoxy-3-nonen-2-one, 3,7-dimethyl-5-methoxy-3-nonen-2-one, 3,8-dimethyl-5-methoxy-3-nonen-2-one, 4,5-dimethyl-5-methoxy-3-nonen-2-one, 4,6-dimethyl-5-methoxy-3-nonen-2-one, 4,7-dimethyl-5-methoxy-3-nonen-2-one, 4,8-dimethyl-5-methoxy-3-nonene-2-one, 5,6-dimethyl-5-methoxy-3-nonen-2-one, 5,7-dimethyl-5-methoxy-3-nonen-2-one, 5,8-dimethyl-5-methoxy-3-nonen-2-one, 6,6-dimethyl-5-methoxy-3-nonen-2-one, 6,7-dimethyl-5-methoxy-3-nonen-2-one, 6,8-dimethyl-5-methoxy-3-nonen-2-one, 7,7-dimethyl-5-methoxy-3-nonen-2-one, 7,8-dimethyl-5-methoxy-3-nonen-2-one, 8,8-dimethyl-5-methoxy-3-nonen-2-one, 3-methoxy-4-hexen-2-one, 3-methoxy-4-hexen-2-one, 5-methoxy-4-hexen-2-one, 6-methoxy-4-hexen-2-one, 3-methoxy-4-heptan-2-one, 4-methoxy-4-heptan-2-one, 5-methoxy-4-heptan-2-one, 6-methoxy-4-heptan-2-one, 7-methoxy-4-heptan-2-one, farnesylacetone and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the aldehyde that may contain an alicyclic structure include, but are not particularly limited to, 2-methylcyclopentyl aldehyde, 3-methylcyclopentyl aldehyde, 2-methyl-1-cyclopentenyl aldehyde, 3-methyl-1-cyclopentenyl aldehyde, 4-methyl-1-cyclopentenyl aldehyde, 5-methyl-1-cyclopentenyl aldehyde, 2-methyl-2-cyclopentenyl aldehyde, 3-methyl-2-cyclopentenyl aldehyde, 4-methyl-2-cyclopentenyl aldehyde, 5-methyl-2-cyclopentenyl aldehyde, 2-methyl-3-cyclopentenyl aldehyde, 3-methyl-3-cyclopentenyl aldehyde, 4-methyl-3-cyclopentenyl aldehyde, 5-methyl-3-cyclopentenyl aldehyde, 2,2-dimethylcyclopentyl aldehyde, 2,3-dimethylcyclopentyl aldehyde, 2,4-dimethylcyclopentyl aldehyde, 2,5-dimethylcyclopentyl aldehyde, 3,3-dimethylcyclopentyl aldehyde, 3,4-dimethylcyclopentyl aldehyde, 2-cyclopentylethane-1-al, 2-(2,2,3-trimethyl-3-cyclopentenyl)-ethane-1-al, cyclohexyl aldehyde, 1-cyclohexenyl aldehyde, 2-cyclohexenyl aldehyde, 3-cyclohexenyl aldehyde, 2-methyl-1-cyclohexenyl aldehyde, 3-methyl-1-cyclohexenyl aldehyde, 4-methyl-1-cyclohexenyl aldehyde, 5-methyl-1-cyclohexenyl aldehyde, 6-methyl-1-cyclohexenyl aldehyde, 2-methyl-2-cyclohexenyl aldehyde, 3-methyl-2-cyclohexenyl aldehyde, 4-methyl-2-cyclohexenyl aldehyde, 5-methyl-2-cyclohexenyl aldehyde, 6-methyl-2-cyclohexenyl aldehyde, 2-methyl-3-cyclohexenyl aldehyde, 3-methyl-3-cyclohexenyl aldehyde, 2,4-dimethyl-3-cyclohexenyl aldehyde, 3,5-dimethyl-3-cyclohexenyl aldehyde, 4-methyl-3-cyclohexenyl aldehyde, 5-methyl-3-cyclohexenyl aldehyde, 6-methyl-3-cyclohexenyl aldehyde, 4-isopropenyl-1-cyclohexenyl aldehyde, 2,4,6-trimethyl-3-cyclohexenyl aldehyde, 2,2,6-trimethylcyclohexyl aldehyde, 2,2,6-trimethyl-6-cyclohexenyl aldehyde, 2,2,6-trimethyl-5-cyclohexenyl aldehyde, 2,2,6-trimethyl-4-cyclohexenyl aldehyde, 2,2-dimethyl-6-exomethyl-6-cyclohexenyl aldehyde, 4-(4-methyl-3-pentenyl)-3-cyclohexenyl aldehyde, 3-(4-methyl-3-pentenyl)-3-cyclohexenyl aldehyde, 4-(4-hydroxy-4-methylpentyl)-3-cyclohexenyl aldehyde, 3-(4-hydroxy-4-methylpentyl)-3-cyclohexenyl aldehyde, 1-methyl-4-(4-methylpentyl)-3-cyclohexenyl aldehyde, 4-(tricyclo[5.2.1.0]-decyliden-8)-butenal, 7-formyl-5-isopropyl-2-methyl-bicyclo[2.2.2]-2-octene, 2-methyl-4-(2,6,6-trimethyl-1-cylcohexen-1-yl)-2-butenal, 2-methyl-4-(2,6,6-trimethyl-2-cylcohexen-1-yl)-2-butanal and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the ketones that may have an aliphatic cyclic structure include, but are not particularly limited to, 2-methylcyclopentyl methyl ketone, 3-methylcyclopentyl methyl ketone, 2-methyl-1-cyclopentenyl methyl ketone, 3-methyl-1-cyclopentenyl methyl ketone, 4-methyl-1-cyclopentenyl methyl ketone, 5-methyl-1-cyclopentenyl methyl ketone, 2-methyl-2-cyclopentenyl methyl ketone, 3-methyl-2-cyclopentenyl methyl ketone, 4-methyl-2-cyclopentenyl methyl ketone, 5-methyl-2-cyclopentenyl methyl ketone, 2-methyl-3-cyclopentenyl methyl ketone, 3-methyl-3-cyclopentenyl methyl ketone, 4-methyl-3-cyclopentenyl methyl ketone, 5-methyl-3-cyclopentenyl methyl ketone, 2,2-dimethylcyclopentyl methyl ketone, 2,3-dimethylcyclopentyl methyl ketone, 2,4-dimethylcyclopentyl methyl ketone, 2,5-dimethylcyclopentyl methyl ketone, 3,3-dimethylcyclopentyl methyl ketone, 3,4-dimethylcyclopentyl methyl ketone, 2-cyclopentyl ethane-1- radius, 2-(2,2,3-trimethyl-3-cyclopentenyl)-ethane-1-radius, cyclohexyl methyl ketone, 1-cyclohexenyl methyl ketone, 2-cyclohexenyl methyl ketone, 3-cyclohexenyl methyl ketone, 2-methyl-1-cyclohexenyl methyl ketone, 3-methyl-1-cyclohexenyl methyl ketone, 4-methyl-1-cyclohexenyl methyl ketone, 5-methyl-1-cyclohexenyl methyl ketone, 6-methyl-1-cyclohexenyl methyl ketone, 2-methyl-2-cyclohexenyl methyl ketone, 3-methyl-2-cyclohexenyl methyl ketone, 4-methyl-2-cyclohexenyl methyl ketone, 5-methyl-2-cyclohexenyl methyl ketone, 6-methyl-2-cyclohexenyl methyl ketone, 2-methyl-3-cyclohexenyl methyl ketone, 3-methyl-3-cyclohexenyl methyl ketone, 4-methyl-3-cyclohexenyl methyl ketone, 5-methyl-3-cyclohexenyl methyl ketone, 6-methyl-3-cyclohexenyl methyl ketone, α-damascone, β-damascone, δ-damascone, α-ionone, β-ionone, δ-ionone, methylionone, damascenone, dinascone, ilone, nootkatone, cedryl methylketone, fenchone, piperitone, pulegone, menthone, carvone, camphor, 2,2,6-trimethylcyclohexyl methyl ketone, 2,2,6-trimethyl-6-cyclohexenyl methyl ketone, 2,2,6-trimethyl-5-cyclohexenyl methyl ketone, 2,2,6-trimethyl-4-cyclohexenyl methyl ketone, 2,5,5-trimethyl-5-pentylcyclopentanone, p-menthen-6-yl propanone, 7-methyloctahydro-1,4-methanonaphthalen-6(2H)-one, cis-jasmone, dihydrojasmone, heptylcyclopentanone, amylcyclopentanone, p-tert-butylcyclohexanone, sugar lactone, 2,5-dimethyl-4-hydroxy-2H-furan-3-one, ethylmaltol, maltol, 2,2-dimethyl-6-exomethyl-6-cyclohexenyl methyl ketone, methyl-2,6,10-trimethyl-2,5,9-cyclododecatrien-1-yl ketone, 7-acetyl-1,2,3,4,5,6,7,8-octahydro-1,1,6,7-tetramethylnaphthalene, 6,7-dihydro-1,1,2,3,3-pentamethyl 4(5H)-indanone, 4-(1-ethoxyvinyl)-3,5,5-tetramethylcyclohexanone and the like. Even if geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of aldehydes and ketones that may contain aromatic rings include, but are not particularly limited to, benzaldehyde, phenyl acetaldehyde, 4-methylphenyl acetaldehyde, phenylpropyl aldehyde, acetophenone, 4-methylacetophenone, benzyl acetone, calone, raspberry ketone, anisyl acetone, 4-hydroxybenzaldehyde, 4-hydroxyacetophenone, zingerone, methyl naphthyl ketone, benzophenone, 4-phenyl-4-methyl-2-pentanone, 2-methylbenzaldehyde, 3-methylbenzaldehyde, 4-methylbenzaldehyde, cinnamic aldehyde, α-amylcinnamic aldehyde, α-hexylcinnamic aldehyde, 2-phenylpropanal, 4-hydroxy-3-methoxy acetophenone, anisaldehyde, cuminaldehyde, cyclamenaldehyde, 2-methyl-3-p-methoxyphenyl-propanal, 3-(p-ethylphenyl)-2,2-dimethylpropanal, 3-(p-ethylphenyl)-2,2-dimethylpropanal, 2-methyl-3-(p-tert-butylphenyl)propanal, salicylaldehyde, 2-pyridinecarboxyaldehyde, 6-methyl-2-pyridinecarboxyaldehyde, 2-acetylpyridine and the like. Even if arene substitutional, geometrical or optical isomers are present, the individual isomer or the mixture thereof may be used.

Among the branched or straight-chain, cyclic or linear, saturated or unsaturated aldehydes and ketones, that is the raw materials for the acetal or ketal derivative of the present invention, in which a total carbon atom of the groups A and B is 6 to 18, which may have one or more substituent groups such as hydroxyl and ether groups and which may have an aromatic ring and an fused ring connected thereto, examples of the aldehyde and ketone that may have a fused ring connected to an aromatic ring include, but are not particularly limited to, 6-methyl-1-indanon, alpha-tetorarone, 1-naphthalenealdehyde, 2-naphthalenealdehyde, 3,4-methylenedioxy acetophenone, piperonal, 2-methyl-3-(3,4-methylenedioxyphenyl)propanal, indole-5-aldehyde, indole-5-aldehyde, 4-quinolinealdehyde, 7-quinolinealdehyde, 3-chromonealdehyde, 2-benzofuranaldehyde, 2-acethylbenzofran and the like. Even if arene substitutional, geometrical or optical isomers are present, the individual isomer or the mixture thereof may be used.

Similarly, among the cyclic or linear alcohol having 6 to 14 carbon atoms, that may be branched, may have one or more unsaturated bonds, and may have an ether groups, an aromatic ring and an fused ring connected thereto in Formula (3), examples of the linear-chain or branched saturated alcohol include, but are not particularly limited to, hexanol, heptanol, octanol, nonanol, decanol, undecanol, dodecanol, tridecanol, tetradecanol, 2-methylhexanol, 3-methylhexanol, 4-methylhexanol, 5-methylhexanol, 2-methylheptanol, 3-methylheptanol, 4-methylheptanol, 5-methylheptanol, 6-methylheptanol, 2-methyloctanol, 3-methyloctanol, 4-methyloctanol, 5-methyloctanol, 6-methyloctanol, 7-methyloctanol, 2-methylnonanol, 3-methylnonanol, 4-methylnonanol, 5-methylnonanol, 6-methylnonanol, 7-methylnonanol, 8-methylnonanol, 2-methyldecanol, 3-methyldecanol, 4-methyldecanol, 5-methyldecanol, 6-methyldecanol, 7-methyldecanol, 8-methyldecanol, 9-methyldecanol, 2,3-dimethylpentanol, 2,4-dimethylpentanol, 2,2-dimethylpentanol, 3,3-dimethylpentanol, 3,4-dimethylpentanol, 4,4-dimethylpentanol, 2,2-dimethylhexanol, 2,3-dimethylhexanol, 2,4-dimethylhexanol, 2,5-dimethylhexanol, 3,3-dimethylhexanol, 3,4-dimethylhexanol, 3,5-dimethylhexanol, 4,4-dimethylhexanol, 4,5-dimethylhexanol, 5,5-dimethylhexanol, 2,2-dimethylheptanol, 2,3-dimethylheptanol, 2,4-dimethylheptanol, 2,5-dimethylheptanol, 2,6-dimethylheptanol, 3,3-dimethylheptanol, 3,4-dimethylheptanol, 3,5-dimethylheptanol, 3,6-dimethylheptanol, 4,4-dimethylheptanol, 4,5-dimethylheptanol, 4,6-dimethylheptanol, 5,5-dimethylheptanol, 5,6-dimethylheptanol, 6,6-dimethylheptanol, 2,2-dimethyloctanol, 2,3-dimethyloctanol, 2,4-dimethyloctanol, 2,5-dimethyloctanol, 2,6-dimethyloctanol, 2,7-dimethyloctanol, 3,3-dimethyloctanol, 3,4-dimethyloctanol, 3,5-dimethyloctanol, 3,6-dimethyloctanol, 3,7-dimethyloctanol, 4,4-dimethyloctanol, 4,5-dimethyloctanol, 4,6-dimethyloctanol, 4,7-dimethyloctanol, 5,5-dimethyloctanol, 5,6-dimethyloctanol, 5,7-dimethyloctanol, 6,6-dimethyloctanol, 6,7-dimethyloctanol, 7,7-dimethyloctanol, 2,2-dimethylnonanol, 2,3-dimethylnonanol, 2,4-dimethylnonanol, 2,5-dimethylnonanol, 2,6-dimethylnonanol, 2,7-dimethylnonanol, 2,8-dimethylnonanol, 3,3-dimethylnonanol, 3,4-dimethylnonanol, 3,5-dimethylnonanol, 3,6-dimethylnonanol, 3,7-dimethylnonanol, 3,8-dimethylnonanol, 4,4-dimethylnonanol, 4,5-dimethylnonanol, 4,6-dimethylnonanol, 4,7-dimethylnonanol, 4,8-dimethylnonanol, 5,5-dimethylnonanol, 5,6-dimethylnonanol, 5,7-dimethylnonanol, 5,8-dimethylnonanol, 6,6-dimethylnonanol, 6,7-dimethylnonanol, 6,8-dimethylnonanol, 7,7-dimethylnonanol, 7,8-dimethylnonanol, 8,8-dimethylnonanol, 3-methyl-2-hexanol, 4-methyl-2-hexanol, 5-methyl-2-hexanol, 3-methyl-2-heptanol, 4-methyl-2-heptanol, 5-methyl-2-heptanol, 6-methyl-2-heptanol, 3-methyl-2-octanol, 4-methyl-2-octanol, 5-methyl-2-octanol, 6-methyl-2-octanol, 7-methyl-2-octanol, 3-methyl-2-nonanol, 4-methyl-2-nonanol, 5-methyl-2-nonanol, 6-methyl-2-nonanol, 7-methyl-2-nonanol, 8-methyl-2-nonanol, 3-methyl-2-decanol, 4-methyl-2-decanol, 5-methyl-2-decanol, 6-methyl-2-decanol, 7-methyl-2-decanol, 8-methyl-2-decanol, 9-methyl-2-decanol, 3,3-dimethyl-2-pentanol, 3,4-dimethyl-2-pentanol, 4,4-dimethyl-2-pentanol, 3,3-dimethyl-2-hexanol, 3,4-dimethyl-2-hexanol, 3,5-dimethyl-2-hexanol, 4,4-dimethyl-2-hexanol, 4,5-dimethyl-2-hexanol, 5,5-dimethyl-2-hexanol, 3,3-dimethyl-2-heptanol, 3,4-dimethyl-2-heptanol, 3,5-dimethyl-2-heptanol, 3,6-dimethyl-2-heptanol, 4,4-dimethyl-2-heptanol, 4,5-dimethyl-2-heptanol, 4,6-dimethyl-2-heptanol, 5,5-dimethyl-2-heptanol, 5,6-dimethyl-2-heptanol, 6,6-dimethyl-2-heptanol, 3,3-dimethyl-2-octanol, 3,4-dimethyl-2-octanol, 3,5-dimethyl-2-octanol, 3,6-dimethyl-2-octanol, 3,7-dimethyl-2-octanol, 4,4-dimethyl-2-octanol, 4,5-dimethyl-2-octanol, 4,6-dimethyl-2-octanol, 4,7-dimethyl-2-octanol, 5,5-dimethyl-2-octanol, 5,6-dimethyl-2-octanol, 5,7-dimethyl-2-octanol, 6,6-dimethyl-2-octanol, 6,7-dimethyl-2-octanol, 7,7-dimethyl-2-octanol, 3,3-dimethyl-2-nonanol, 3,4-dimethyl-2-nonanol, 3,5-dimethyl-2-nonanol, 3,6-dimethyl-2-nonanol, 3,7-dimethyl-2-nonanol, 3,8-dimethyl-2-nonanol, 4,4-dimethyl-2-nonanol, 4,5-dimethyl-2-nonanol, 4,6-dimethyl-2-nonanol, 4,7-dimethyl-2-nonanol, 4,8-dimethyl-2-nonanol, 5,5-dimethyl-2-nonanol, 5,6-dimethyl-2-nonanol, 5,7-dimethyl-2-nonanol, 5,8-dimethyl-2-nonanol, 6,6-dimethyl-2-nonanol, 6,7-dimethyl-2-nonanol, 6,8-dimethyl-2-nonanol, 7,7-dimethyl-2-nonanol, 7,8-dimethyl-2-nonanol, 8,8-dimethyl-2-nonanol and the like. Even if optical isomers are present, the individual isomer or the mixture thereof may be used.

Similarly, among the cyclic or linear alcohol having 6 to 14 carbon atoms, that may be branched, may have one or more unsaturated bonds, and may have an ether groups, an aromatic ring and an fused ring connected thereto in Formula (3), examples of the straight-chain or branched unsaturated alcohols include, but are not particularly limited to, 2-hexen-1-ol, 3-hexen-1-ol, 4-hepten-2-ol, 3-octen-2-ol, 1-octen-3-ol, 5-nonen-2-ol, 5-decen-2-ol, 9-decen-1-ol, 5-undecen-2-ol, 10-undecen-1-ol, 5-tetradecen-2-ol, 3-methyl-4-hexen-2-ol, 4-methyl-4-hexen-2-ol, 5-methyl-4-hexen-2-ol, 3-methyl-4-hepten-2-ol, 4-methyl-4-hepten-2-ol, 5-methyl-4-hepten-2-ol, 6-methyl-4-hepten-2-ol, 3-methyl-3-octen-2-ol, 4-methyl-3-octen-2-ol, 5-methyl-3-octen-2-ol, 6-methyl-3-octen-2-ol, 7-methyl-3-octen-2-ol, 3-methyl-5-nonen-2-ol, 4-methyl-5-nonen-2-ol, 5-methyl-5-nonen-2-ol, 6-methyl-5-nonen-2-ol, 7-methyl-5-nonen-2-ol, 8-methyl-5-nonen-2-ol, 3-methyl-5-decen-2-ol, 3-methyl-5-decen-2-ol, 4-methyl-5-decen-2-ol, 4-methyl-3-decen-5-ol, 5-methyl-5-decen-2-ol, 6-methyl-5-decen-2-ol, 7-methyl-5-decen-2-ol, 8-methyl-5-decen-2-ol, 9-methyl-5-decen-2-ol, 3,4-dimethyl-3-penten-2-ol, 3,3-dimethyl-4-hexen-2-ol, 3,4-dimethyl-4-hexen-2-ol, 3,5-dimethyl-4-hexen-2-ol, 4,5-dimethyl-4-hexen-2-ol, 3,3-dimethyl-4-hepten-2-ol, 3,4-dimethyl-4-hepten-2-ol, 3,5-dimethyl-4-hepten-2-ol, 3,6-dimethyl-4-hepten-2-ol, 4,5-dimethyl-4-hepten-2-ol, 4,6-dimethyl-4-hepten-2-ol, 5,6-dimethyl-4-hepten-2-ol, 6,6-dimethyl-4-hepten-2-ol, 3,4-dimethyl-3-octen-2-ol, 3,5-dimethyl-3-octen-2-ol, 3,6-dimethyl-3-octen-2-ol, 3,7-dimethyl-3-octen-2-ol, 4,5-dimethyl-3-octen-2-ol, 4,6-dimethyl-3-octen-2-ol, 4,7-dimethyl-3-octen-2-ol, 5,5-dimethyl-3-octen-2-ol, 5,6-dimethyl-3-octen-2-ol, 5,7-dimethyl-3-octen-2-ol, 6,6-dimethyl-3-octen-2-ol, 6,7-dimethyl-3-octen-2-ol, 7,7-dimethyl-3-octen-2-ol, 3,3-dimethyl-5-nonen-2-ol, 3,4-dimethyl-5-nonen-2-ol, 3,5-dimethyl-5-nonen-2-ol, 3,6-dimethyl-5-nonen-2-ol, 3,7-dimethyl-5-nonen-2-ol, 3,8-dimethyl-5-nonen-2-ol, 4,4-dimethyl-5-nonen-2-ol, 4,5-dimethyl-5-nonen-2-ol, 4,6-dimethyl-5-nonen-2-ol, 4,7-dimethyl-5-nonen-2-ol, 4,8-dimethyl-5-nonen-2-ol, 5,6-dimethyl-5-nonen-2-ol, 5,7-dimethyl-5-nonen-2-ol, 5,8-dimethyl-5-nonen-2-ol, 6,7-dimethyl-5-nonen-2-ol, 6,8-dimethyl-5-nonen-2-ol, 7,7-dimethyl-5-nonen-2-ol, 7,8-dimethyl-5-nonen-2-ol, 8,8-dimethyl-5-nonen-2-ol, 2,6-nonadien-1-ol, linalool, geraniol, nerol, citronellol, myrcenol, lavandulol, dihydromyrcenol, allocimenol and the like. Even if geometrical or optical isomers are present, the individual isomer or the mixture thereof may be used.

Similarly, among the cyclic or linear alcohol having 6 to 14 carbon atoms, that may be branched, may have one or more unsaturated bonds, and may have an ether groups, an aromatic ring and an fused ring connected thereto in Formula (3), examples of ether group-containing straight-chain or branched saturated alcohol include, but are not particularly limited to, 3-methoxy-3-methyl-butanol, 3-methoxyhexanol, 3-methoxyheptanol, 3-methoxyoctanol, 3-methoxynonanol, 3-methoxydecanol, 3-methoxytridecanol, 2-methyl-3-methoxyhexanol, 3-methyl-3-methoxyhexanol, 4-methyl-3-methoxyhexanol, 5-methyl-3-methoxyhexanol, 2-methyl-3-methoxyheptanol, 3-methyl-3-methoxyheptanol, 4-methyl-3-methoxyheptanol, 5-methyl-3-methoxyheptanol, 6-methyl-3-methoxyheptanol, 2-methyl-3-methoxyoctanol, 3-methyl-3-methoxyoctanol, 4-methyl-3-methoxyoctanol, 5-methyl-3-methoxyoctanol, 6-methyl-3-methoxyoctanol, 7-methyl-3-methoxyoctanol, 2-methyl-3-methoxynonanol, 3-methyl-3-methoxynonanol, 4-methyl-3-methoxynonanol, 5-methyl-3-methoxynonanol, 6-methyl-3-methoxynonanol, 7-methyl-3-methoxynonanol, 8-methyl-3-methoxynonanol, 2,3-dimethyl-3-methoxypentanol, 2,4-dimethyl-3-methoxypentanol, 2,2-dimethyl-3-methoxypentanol, 3,4-dimethyl-3-methoxypentanol, 4,4-dimethyl-3-methoxypentanol, 2,2-dimethyl-3-methoxyhexanol, 2,3-dimethyl-3-methoxyhexanol, 2,4-dimethyl-3-methoxyhexanol, 2,5-dimethyl-3-methoxyhexanol, 3,4-dimethyl-3-methoxyhexanol, 3,5-dimethyl-3-methoxyhexanol, 4,4-dimethyl-3-methoxyhexanol, 4,5-dimethyl-3-methoxyhexanol, 5,5-dimethyl-3-methoxyhexanol, 2,2-dimethyl-3-methoxyheptanol, 2,3-dimethyl-3-methoxyheptanol, 2,4-dimethyl-3-methoxyheptanol, 2,5-dimethyl-3-methoxyheptanol, 2,6-dimethyl-3-methoxyheptanol, 3,4-dimethyl-3-methoxyheptanol, 3,5-dimethyl-3-methoxyheptanol, 3,6-dimethyl-3-methoxyheptanol, 4,4-dimethyl-3-methoxyheptanol, 4,5-dimethyl-3-methoxyheptanol, 4,6-dimethyl-3-methoxyheptanol, 5,5-dimethyl-3-methoxyheptanol, 5,6-dimethyl-3-methoxyheptanol, 6,6-dimethyl-3-methoxyheptanol, 2,2-dimethyl-3-methoxyoctanol, 2,3-dimethyl-3-methoxyoctanol, 2,4-dimethyl-3-methoxyoctanol, 2,5-dimethyl-3-methoxyoctanol, 2,6-dimethyl-3-methoxyoctanol, 2,7-dimethyl-3-methoxyoctanol, 3,4-dimethyl-3-methoxyoctanol, 3,5-dimethyl-3-methoxyoctanol, 3,6-dimethyl-3-methoxyoctanol, 3,7-dimethyl-3-methoxyoctanol, 4,4-dimethyl-3-methoxyoctanol, 4,5-dimethyl-3-methoxyoctanol, 4,6-dimethyl-3-methoxyoctanol, 4,7-dimethyl-3-methoxyoctanol, 5,5-dimethyl-3-methoxyoctanol, 5,6-dimethyl-3-methoxyoctanol, 5,7-dimethyl-3-methoxyoctanol, 6,6-dimethyl-3-methoxyoctanol, 6,7-dimethyl-3-methoxyoctanol, 7,7-dimethyl-3-methoxyoctanol, and the like. Even if optical isomers are present, the individual isomer or the mixture thereof may be used.

Similarly, among the cyclic or linear alcohol having 6 to 14 carbon atoms, that may be branched, may have one or more unsaturated bonds, and may have an ether groups, an aromatic ring and an fused ring connected thereto in Formula (3), examples of the ether group-containing linear or branched unsaturated alcohols include, but are not particularly limited to, 5-methoxy-2-hexenol, 5-methoxy-2-heptenol, 5-methoxy-2-octenol, 5-methoxy-2-nonenol, 5-methoxy-2-decenol, 5-methoxy-2-tridecenol, 5-methoxy-2-undecenol, 2-methyl-5-methoxy-2-hexenol, 3-methyl-5-methoxy-2-hexenol, 4-methyl-5-methoxy-2-hexenol, 5-methyl-5-methoxy-2-hexenol, 2-methyl-5-methoxy-2-heptenol, 3-methyl-5-methoxy-2-heptenol, 4-methyl-5-methoxy-2-heptenol, 5-methyl-5-methoxy-2-heptenol, 6-methyl-5-methoxy-2-heptenol, 2-methyl-5-methoxy-2-octenol, 3-methyl-5-methoxy-2-octenol, 4-methyl-5-methoxy-2-octenol, 5-methyl-5-methoxy-2-octenol, 6-methyl-5-methoxy-2-octenol, 7-methyl-5-methoxy-2-octenol, 2-methyl-5-methoxy-2-nonenol, 3-methyl-5-methoxy-2-nonenol, 4-methyl-5-methoxy-2-nonenol, 5-methyl-5-methoxy-2-nonenol, 6-methyl-5-methoxy-2-nonenol, 7-methyl-5-methoxy-2-nonenol, 8-methyl-5-methoxy-2-nonenol, 2-methyl-5-methoxy-2-decenol, 2-methyl-5-methoxy-2-decenol, 3-methyl-5-methoxy-2-decenol, 3-methyl-5-methoxy-2-decenol, 4-methyl-5-methoxy-2-decenol, 5-methyl-5-methoxy-2-decenol, 6-methyl-5-methoxy-2-decenol, 7-methyl-5-methoxy-2-decenol, 8-methyl-5-methoxy-2-decenol, 9-methyl-5-methoxy-2-decenol, 2,3-dimethyl-4-methoxy-2-pentenol, 2,4-dimethyl-4-methoxy-2-pentenol, 3,4-dimethyl-4-methoxy-2-pentenol, 2,3-dimethyl-5-methoxy-2-hexenol, 2,4-dimethyl-5-methoxy-2-hexenol, 2,5-dimethyl-5-methoxy-2-hexenol, 3,4-dimethyl-5-methoxy-2-hexenol, 3,5-dimethyl-5-methoxy-2-hexenol, 4,4-dimethyl-5-methoxy-2-hexenol, 4,5-dimethyl-5-methoxy-2-hexenol, 2,3-dimethyl-5-methoxy-2-heptenol, 2,4-dimethyl-5-methoxy-2-heptenol, 2,5-dimethyl-5-methoxy-2-heptenol, 2,6-dimethyl-5-methoxy-2-heptenol, 3,4-dimethyl-5-methoxy-2-heptenol, 3,5-dimethyl-5-methoxy-2-heptenol, 3,6-dimethyl-5-methoxy-2-heptenol, 4,4-dimethyl-5-methoxy-2-heptenol, 4,5-dimethyl-5-methoxy-2-heptenol, 4,6-dimethyl-5-methoxy-2-heptenol, 5,6-dimethyl-5-methoxy-2-heptenol, 6,6-dimethyl-5-methoxy-2-heptenol, 2,3-dimethyl-5-methoxy-2-octenol, 2,4-dimethyl-5-methoxy-2-octenol, 2,5-dimethyl-5-methoxy-2-octenol, 2,6-dimethyl-5-methoxy-2-octenol, 2,7-dimethyl-5-methoxy-2-octenol, 3,4-dimethyl-5-methoxy-2-octenol, 3,5-dimethyl-5-methoxy-2-octenol, 3,6-dimethyl-5-methoxy-2-octenol, 3,7-dimethyl-5-methoxy-2-octenol, 4,4-dimethyl-5-methoxy-2-octenol, 4,5-dimethyl-5-methoxy-2-octenol, 4,6-dimethyl-5-methoxy-2-octenol, 4,7-dimethyl-5-methoxy-2-octenol, 5,6-dimethyl-5-methoxy-2-octenol, 5,7-dimethyl-5-methoxy-2-octenol, 6,6-dimethyl-5-methoxy-2-octenol, 6,7-dimethyl-5-methoxy-2-octenol, 7,7-dimethyl-5-methoxy-2-octenol, 2,3-dimethyl-5-methoxy-2-nonenol, 2,4-dimethyl-5-methoxy-2-nonenol, 2,5-dimethyl-5-methoxy-2-nonenol, 2,6-dimethyl-5-methoxy-2-nonenol, 2,7-dimethyl-5-methoxy-2-nonenol, 2,8-dimethyl-5-methoxy-2-nonenol, 3,4-dimethyl-5-methoxy-2-nonenol, 3,5-dimethyl-5-methoxy-2-nonenol, 3,6-dimethyl-5-methoxy-2-nonenol, 3,7-dimethyl-5-methoxy-2-nonenol, 3,8-dimethyl-5-methoxy-2-nonenol, 4,4-dimethyl-5-methoxy-2-nonenol, 4,5-dimethyl-5-methoxy-2-nonenol, 4,6-dimethyl-5-methoxy-2-nonenol, 4,7-dimethyl-5-methoxy-2-nonenol, 4,8-dimethyl-5-methoxy-2-nonenol, 5,6-dimethyl-5-methoxy-2-nonenol, 5,7-dimethyl-5-methoxy-2-nonenol, 5,8-dimethyl-5-methoxy-2-nonenol, 6,6-dimethyl-5-methoxy-2-nonenol, 6,7-dimethyl-5-methoxy-2-nonenol, 6,8-dimethyl-5-methoxy-2-nonenol, 7,7-dimethyl-5-methoxy-2-nonenol, 7,8-dimethyl-5-methoxy-2-nonenol, 8,8-dimethyl-5-methoxy-2-nonenol, 5-methoxy-3-heptenol, 5-methoxy-3-octenol, 5-methoxy-3-nonenol, 5-methoxy-3-decenol, 5-methoxy-3-undecenol, 2-methyl-5-methoxy-3-hexenol, 3-methyl-5-methoxy-3-hexenol, 4-methyl-5-methoxy-3-hexenol, 5-methyl-5-methoxy-3-hexenol, 2-methyl-5-methoxy-3-heptenol, 3-methyl-5-methoxy-3-heptenol, 4-methyl-5-methoxy-3-heptenol, 5-methyl-5-methoxy-3-heptenol, 6-methyl-5-methoxy-3-heptenol, 2-methyl-5-methoxy-3-octenol, 3-methyl-5-methoxy-3-octenol, 4-methyl-5-methoxy-3-octenol, 5-methyl-5-methoxy-3-octenol, 6-methyl-5-methoxy-3-octenol, 7-methyl-5-methoxy-3-octenol, 2-methyl-5-methoxy-3-nonenol, 3-methyl-5-methoxy-3-nonenol, 4-methyl-5-methoxy-3-nonenol, 5-methyl-5-methoxy-3-nonenol, 6-methyl-5-methoxy-3-nonenol, 7-methyl-5-methoxy-3-nonenol, 8-methyl-5-methoxy-3-nonenol, 2-methyl-5-methoxy-3-decenol, 3-methyl-5-methoxy-3-decenol, 4-methyl-5-methoxy-3-decenol, 5-methyl-5-methoxy-3-decenol, 6-methyl-5-methoxy-3-decenol, 7-methyl-5-methoxy-3-decenol, 8-methyl-5-methoxy-3-decenol, 9-methyl-5-methoxy-3-decenol and the like. Even if geometrical or optical isomers are present, the individual isomer or the mixture thereof may be used.

Similarly, among the cyclic or linear alcohol having 6 to 14 carbon atoms, that may be branched, may have one or more unsaturated bonds, and may have an ether groups, an aromatic ring and an fused ring connected thereto in Formula (3), examples of the alcohol that may have an alicyclic structure include, but are not particularly limited to, cyclohexanol, 2-methylcyclopentanol, 3-methylcyclopentanol, 2-methyl-1-cyclopentenol, 3-methyl-1-cyclopentenol, 4-methyl-1-cyclopentenol, 5-methyl-1-cyclopentenol, 2-methyl-2-cyclopentenol, 3-methyl-2-cyclopentenol, 4-methyl-2-cyclopentenol, 5-methyl-2-cyclopentenol, 2-methyl-3-cyclopentenol, 3-methyl-3-cyclopentenol, 4-methyl-3-cyclopentenol, 5-methyl-3-cyclopentenol, 2,2-dimethylcyclopentanol, 2,3-dimethylcyclopentanol, 2,4-dimethylcyclopentanol, 2,5-dimethylcyclopentanol, 3,3-dimethylcyclopentanol, 3,4-dimethylcyclopentanol, 2,4-dimethyl-3-cyclohexenylmethanol, 2-cyclopentylethan-1-ol, 2-(2,2,3-trimethyl-3-cyclopentenyl)-ethan-1-ol, cyclohexanol, 1-cyclohexenol, 2-cyclohexenol, 3-cyclohexenol, 2-methyl-1-cyclohexenol, 3-methyl-1-cyclohexenol, 4-methyl-1-cyclohexenol, 4-isopropyl-1-cyclohexanol, 4-isopropyl-1-cyclohexylmethanol, 1-(4-isopropyl-1-cyclohexyl)ethanol, 5-methyl-1-cyclohexenol, 6-methyl-1-cyclohexenol, 2-methyl-2-cyclohexenol, 3-methyl-2-cyclohexenol, 4-methyl-2-cyclohexenol, 5-methyl-2-cyclohexenol, 6-methyl-2-cyclohexenol, 2-methyl-3-cyclohexenol, 3-methyl-3-cyclohexenol, 4-methyl-3-cyclohexenol, 5-methyl-3-cyclohexenol, 6-methyl-3-cyclohexenol, 2,2,6-trimethylcyclohexyl alcohol, 2,2,6-trimethyl-6-cyclohexenol, 2,2,6-trimethyl-5-cyclohexenol, 2,2,6-trimethyl-4-cyclohexenol, 2,2-dimethyl-6-exomethyl-6-cyclohexenol, 4-tert-butylcyclohexanol, 2-tert-butylcyclohexanol, terpineol, borneol, nopol, ambrinol and the like. Even if geometrical or optical isomers are present, the individual isomer or the mixture thereof may be used.

Similarly, among the cyclic or linear alcohol having 6 to 14 carbon atoms, that may be branched, may have one or more unsaturated bonds, and may have an ether groups, an aromatic ring and an fused ring connected thereto in Formula (3), examples of the alcohols that may have an aromatic ring include, but are not particularly limited to, benzyl alcohol, styrallyl alcohol, hydroquinone, 4-hydroxystyrallyl alcohol, vanillyl alcohol, 2-methylbenzyl alcohol, 3-methylbenzyl alcohol, 4-methylbenzyl alcohol, cinnamic alcohol, 4-hydroxy-3-methoxystyrallyl alcohol, anisyl alcohol, catechol, 5-methylfurfuryl alcohol, 2-pyridinylethanol and the like. Even if arene substitutional, geometrical or optical isomers are present, the individual isomer or the mixture thereof may be used.

Similarly, among the cyclic or linear alcohol having 6 to 14 carbon atoms, that may be branched, may have one or more unsaturated bonds, and may have an ether groups, an aromatic ring and an fused ring connected thereto in Formula (3), examples of the alcohols that may have a fused ring connected to an aromatic ring include, but are not particularly limited to, 6-methyl-1-indanol, α-tetrarol, 1-naphthyl methanol, 2-naphthyl methanol, pyperonyl alcohol, 3-chromonol, 2-benzofurfuryl alcohol and the like. Even if arene substitutional, geometrical or optical isomers are present, the individual isomer or the mixture thereof may be used.

Examples of the long-chain saturated carboxylic acids having 12 to 20 carbon atoms (carbon atom number including $R^6$ and carbonyl in Formula) that may be branched and may have an unsaturated bond, for use as the raw material for the carboxylic ester represented by Formula (4) of the present invention, include, but are not particularly limited to, saturated carboxylic acids such as lauric acid, myristic acid, pentadecanoic acid, palmitic acid, margaric acid, stearic acid, isostearic acid, tuberculostearic acid and arachidic acid; unsaturated carboxylic acids such as myristoleic acid, palmitoleic acid, oleic acid, elaidic acid, vaccenic acid, gadoleic acid, linolic acid, α-linoleic acid, γ-linoleic acid, eleostearic acid, stearidonic acid, arachidonic acid, 8,11-eicosadienoic acid, 5,8,11-eicosatrienoic acid and eicosapentaenoic acid; and the like.

As described above, the compounds represented by Formulae (1') (2'), (3'), and (4) are new substances among the compounds represented by Formulae (1) to (4).

Hereinafter, preparation methods for the compounds represented by Formulae (1) to (4) will be exemplified, but the preparation methods thereof, of course, not limited thereto.

A following compound represented by Formula (1) of the present invention (hereinafter, referred to as "acetal and ketal derivative") is prepared by heating a mixture of 3-(1-menthoxy)propan-1,2-diol and the corresponding aldehyde or ketone to react those in a suitable solvent in the presence of an acid catalyst:

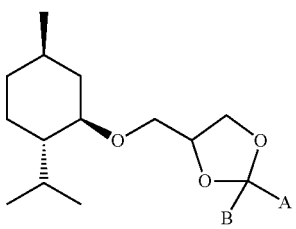

(1)

wherein, each of A and B is a hydrogen atom or a hydrocarbon group which may have one or more substituents, in which A and B are not hydrogen atoms simultaneously, and the total number of carbon atoms in A and B is in the range of 6 to 18.

Examples of the acid catalysts used in the reaction include, but are not particularly limited to, sulfuric acid, trifluoromethanesulfonic acid, methanesulfonic acid, benzenesulfonic acid, p-toluenesulfonic acid, camphorsulfonic acid, naphthalenesulfonic acid and the like. Lewis acids that do not lose its activity by reaction with water can also be used, and examples thereof include zinc chloride, zinc bromide, iron chloride (III) and the like, but are not particularly limited thereto.

The amount of the acid catalyst used is preferably 0.01 to 3.0 moles, more preferably, 0.1 to 1.0 moles, with respect to 1 mole of 3-(1-menthoxy)propan-1,2-diol. As for the ratio of 3-(1-menthoxy)propan-1,2-diol to the corresponding aldehyde or ketone used, the amount of the corresponding aldehyde or ketone is preferably 0.1 to 5.0 moles, more preferably 0.5 to 2.5 moles, with respect to 1 mole of menthol.

The solvent used in the reaction is preferably a solvent that can dissolve 3-(1-menthoxy)propan-1,2-diol and the corresponding aldehyde or ketone, is a non-alcoholic or non-carbonyl solvent, has a suitable boiling point allowing removal of water generated in reaction out of the system, and can remove water azeotropically. Examples of the solvents include methylene chloride, chloroform, hexane, heptane, benzene, cyclohexane, methylcyclohexane, chlorobenzene, xylene, cumene and the like, but are not particularly limited thereto.

The amount of the solvent used is preferably 0.1 to 100 parts by weight, more preferably 0.4 to 10 parts by weight, with respect to 1 part of 3-(1-menthoxy)propan-1,2-diol. The reaction time and the reaction temperature vary significantly according to the boiling point of the solvent used, because the system is dehydrated azeotropically, as it is refluxed under heat, but normally, the reaction is carried out at 35° C. to 180° C., preferably at 70° C. to 130° C., for example for 10 minutes to 8 hours.

Single or mixed carbonic esters of one or two kinds of alcohols represented by Formula (2) of the present invention:

(2)

wherein, $R^1$ and $R^2$ each represent an alcohol residue selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol and para-menthan-3,8-diol); and mixed carbonic esters of two kinds of alcohols represented by Formula (3):

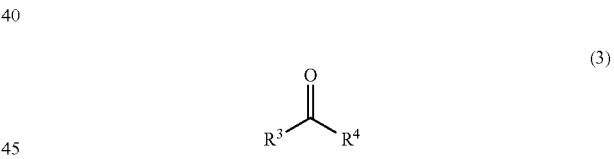

(3)

wherein, $R^3$ represents an alcohol residue selected from 1-menthol, 1-isopulegol, 3-(1-menthoxy)propan-1,2-diol, 2-(1-menthoxy)ethan-1-ol, 3-(1-menthoxy)propan-1-ol, 2-methyl-3-(1-menthoxy)propan-1,2-diol and para-menthan-3,8-diol; and $R^4$ represents a branched or straight-chain, cyclic or linear, or saturated or unsaturated alcohol having 6 to 18 carbon atoms that may have one or more aromatic rings that may have a condensed ring and substituent groups such as hydroxyl and ether groups (hereinafter, these compounds (2) and (3) will be referred to collectively as "carbonic ester derivatives") are produced, for example, in the following manner:

In the case of a single carbonic ester, a desirable single carbonic ester can be prepared by reacting phosgene with a corresponding one kind of alcohol in addition reaction in a suitable solvent in the presence of a base. Examples of the bases include picoline, pyridine, piperidine, pyrrole, imidazole, triethylamine, pyrrolidine, dimethylaminopyridine, potassium carbonate, sodium carbonate, lithium carbonate and the like, but are not particularly limited thereto. The bases may be used alone or as a mixture of two or more.

The solvent is preferably a non-alcoholic solvent that dissolves the corresponding alcohol but is not reactive with phosgene. Examples of the solvents include methylene chloride, chloroform, hexane, heptane, benzene, cyclohexane, diethyl ether, dimethoxyethane, diisopropyl ether, tetrahydrofuran, methylcyclohexane, chlorobenzene, xylene, cumene and the like, but are not particularly limited thereto. Triphosgene, which generates phosgene in the system, may be used as the alternative of phosgene.

The amount of the solvent used is preferably 0.1 to 100 parts by weight, more preferably 0.4 to 10 parts by weight with respect to 1 part of the corresponding alcohol, and the amount of the base is preferably 0.5 to 10 moles, more preferably 0.8 to 3 moles, with respect to 1 mole of the corresponding alcohol. As for the reaction time and the reaction temperature, the reaction is carried out normally at −30° C. to 120° C., preferably-20° C. to 80° C., for example, for 30 minutes to 8 hours.

In the case of a single carbonic ester, it may be prepared in ester-exchange reaction of a suitable carbonic ester with the corresponding one kind of alcohol in a suitable solvent in the presence of an acid catalyst. Examples of the acid catalysts include sulfuric acid, trifluoromethanesulfonic acid, methanesulfonic acid, benzenesulfonic acid, p-toluenesulfonic acid, camphorsulfonic acid, naphthalenesulfonic acid and the like, but are not particularly limited thereto. Lewis acids that do not lose its activity by reaction with water can also be used, and examples thereof include zinc chloride, zinc bromide, iron chloride (III) and the like, but are not particularly limited thereto.

The solvent is preferably a non-alcoholic solvent that can dissolve the corresponding alcohol and the carbonic ester and has a suitable boiling point for removal of the alcohol derived from the raw carbonic ester out of the system, more preferably a solvent allowing azeotropic separation of the alcohol generated. Examples of the solvents include hexane, heptane, octane, isooctane and the like, but are not particularly limited thereto. The raw carbonic ester is preferably dimethyl carbonate or diethyl carbonate, because they are cheaper, but the examples thereof are not particularly limited thereto.

The amount of the solvent used is preferably 0.1 to 100 parts by weight, more preferably 0.4 to 10 parts by weight with respect to 1 part of the corresponding alcohol. The amount of the raw carbonic ester used is preferably 0.1 to 1.0 moles, more preferably 0.3 to 0.8 moles, with respect to 1 mole of the corresponding alcohol. The reaction time and the reaction temperature vary significantly according to the boiling point of the solvent used, because the alcohol is removed azeotropically as the system is refluxed under heat, but the reaction is carried out normally at 50° C. to 180° C., preferably at 70° C. to 130° C., for example, for 1 hour to 8 hours.

In the case of a mixed carbonic ester, one of the corresponding two kinds of alcohols is first added to phosgene in a suitable solvent to give a chlorocarbonic ester, and the other kind of alcohol is then added and allowed to react in the presence of a base, to give a desirable mixed carbonic ester. Examples of the bases include picoline, pyridine, piperidine, pyrrole, imidazole, triethylamine, pyrrolidine, dimethylaminopyridine, potassium carbonate, sodium carbonate, lithium carbonate and the like, but are not particularly limited thereto. The bases may be used alone or as a mixture of two or more.

The solvent is desirably a non-alcoholic solvent that dissolves the corresponding alcohol but is not reactive with phosgene. Examples of the solvents include methylene chloride, chloroform, hexane, heptane, benzene, cyclohexane, diethyl ether, dimethoxyethane, diisopropyl ether, tetrahydrofuran, methylcyclohexane, chlorobenzene, xylene, cumene and the like, but are not particularly limited thereto. Triphosgene, which generates phosgene in the system, may be used as the alternative of phosgene.

The amount of the solvent used is preferably 0.1 to 100 parts by weight, more preferably 0.4 to 10 parts by weight with respect to 1 part of the corresponding alcohol. The amount of the base used is preferably 0.5 to 10 moles, more preferably 0.8 to 3 moles, with respect to 1 mole of the corresponding alcohol. As for the reaction time and the reaction temperature, the reaction is carried out normally at −30° C. to 120° C., preferably at −20° C. to 80° C. both in the first and second stages, respectively for example for 30 minutes to 8 hours.

In the case of a mixed carbonic ester, one of the corresponding two kinds of alcohol may be first allowed to react with methyl chlorocarbonate in the presence of a base, in a suitable solvent, and the other alcohol is then added thereto for ester-exchange reaction in the presence of a suitable acid catalyst. Examples of the bases include picoline, pyridine, piperidine, pyrrole, imidazole, triethylamine, pyrrolidine, dimethylaminopyridine, potassium carbonate, sodium carbonate, lithium carbonate and the like, but are not particularly limited thereto. The bases may be used alone or as a mixture of two or more. Examples of the second-stage acid catalysts include sulfuric acid, trifluoromethanesulfonic acid, methanesulfonic acid, benzenesulfonic acid, p-toluenesulfonic acid, camphorsulfonic acid, naphthalenesulfonic acid and the like, but are not particularly limited thereto. Lewis acids that do not loose its activity in reaction with water can also be used, and examples thereof include zinc chloride, zinc bromide, iron chloride (III) and the like, but are not particularly limited thereto.

The amount of the solvent used in the first stage is preferably 0.1 to 100 parts by weight, more preferably, 0.4 to 10 parts by weight, with respect to 1 part of the corresponding first kind of alcohol. The amount of the raw chloromethyl carbonate is preferably 0.1 to 3.0 moles, more preferably 0.8 to 1.1 moles, with respect to 1 mole of the corresponding alcohol. As for the reaction time and the reaction temperature, the reaction is carried out normally at −30° C. to 120° C., preferably at −20° C. to 80° C., for example, for 1 hour to 8 hours.

The amount of the solvent used in the second stage is preferably 0.1 to 100 parts by weight, more preferably 0.4 to 10 parts by weight, with respect to 1 part of the corresponding second kind of alcohol. The amount of the second kind of alcohol used is preferably 0.5 to 3.0 moles, more preferably 0.7 to 1.3 moles with respect to 1 mole of the first kind of alcohol, and, although the reaction time and the reaction temperature vary significantly according to the boiling point of the solvent used, because the reaction is carried out while the system is refluxed under heating and the alcohol is removed azeotropically, the reaction is carried out normally at 50° C. to 180° C., preferably at 70° C. to 130° C., for example, for 1 hour to 8 hours.

The carboxylic ester represented by Formula (4) of the present invention (hereinafter, referred to as long-chain carboxylic ester derivative):

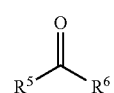

(4)

wherein, R⁵ represents an alcohol residue selected from 1-menthol, 1-isopulegol, 3-(1-menthoxy)propan-1,2-diol, 2-(1-menthoxy)ethane-1-ol, 3-(1-menthoxy)propan-1-ol, 2-methyl-3-(1-menthoxy)propan-1,2-diol, and para-menthan-3,8-diol, and $R^6$ represents a hydrocarbon group having 11 to 19 carbon atoms that may be branched and contain one or more unsaturated bonds,
can be prepared in the following manner:

First, the corresponding long-chain carboxylic acid is allowed to react with a suitable chlorinating agent such as thionyl chloride in a suitable solvent, to give a long-chain carboxylic chloride, and then react it with the corresponding alcohol in the presence of a base, to give a desirable long-chain carboxylic ester. Examples of the bases include picoline, pyridine, piperidine, pyrrole, imidazole, triethylamine, pyrrolidine, dimethylaminopyridine, potassium carbonate, sodium carbonate, lithium carbonate and the like, but are not particularly limited thereto. The bases may be used alone or as a mixture of two or more.

The solvent is preferably a non-alcoholic solvent that dissolves the corresponding long chain carboxylic acid and the alcohol and is not reactive with the chlorinating agent such as thionyl chloride. Examples of the solvents include methylene chloride, chloroform, hexane, heptane, benzene, cyclohexane, diethyl ether, dimethoxyethane, diisopropyl ether, tetrahydrofuran, methylcyclohexane, chlorobenzene, xylene, cumene and the like, but are not particularly limited thereto.

The amount of the solvent used in chlorination of the long-chain carboxylic acid in the first stage is preferably 0 to 100 parts by weight, more preferably 0 to 10 parts by weight, with respect to 1 part of the corresponding long-chain carboxylic acid. As for the reaction time and the reaction temperature, the reaction is carried out normally at −30° C. to 120° C., preferably at 10° C. to 80° C., for example, for 30 minutes to 8 hours.

The amount of the solvent used during esterification of the long-chain carboxylic acid with a corresponding alcohol in the second stage is preferably 0.3 to 100 parts by weight, more preferably 0.5 to 10 parts by weight, with respect to 1 part of the corresponding long-chain carboxylic acid. The amount of the corresponding alcohol used is preferably 0.5 to 10 moles, more preferably 0.8 to 3 moles, with respect to 1 mole of the corresponding long-chain carboxylic acid. The amount of the base used is preferably 0.5 to 10 moles, more preferably 0.8 to 3 moles, with respect to 1 mole of the corresponding long-chain carboxylic acid. As for the reaction time and the reaction temperature, the reaction is carried out normally at −30° C. to 120° C., preferably at 10° C. to 80° C., for example, for 30 minutes to 8 hours.

The acetal and ketal derivatives, carbonic ester derivatives, and long-chain carboxylic ester derivatives of the present invention thus obtained have strong and long-lasting cooling action when used individually or as a mixture of two or more and can be used individually as a cooling sensation agent or a sensory stimulation agent.

The application field and the application method of the acetal and ketal derivatives, the carbonic ester derivatives, and the long-chain carboxylic ester derivative obtained by the present invention should be altered according to the kind and application of the product, but normally, they are used in products such as flavor or fragrance compositions, beverage or food products, perfume or cosmetic products, toiletry products, daily utensil products and groceries, fibers, fiber products, clothes, and medicines, at a concentration of $1 \times 10^{-7}$ to 20% by mass, more preferably 0.0001 to 20% by mass, particularly 0.001 to 5% by mass, in the entire composition.

The cooling sensation agent composition of the present invention contains at least one of the acetal and ketal derivatives, the carbonic ester derivatives, and the long-chain carboxylic ester derivative. Accordingly, the cooling sensation agent composition of the present invention may contain only one of the acetal and ketal derivatives, the carbonic ester derivatives, and long-chain carboxylic ester derivatives, or may contain two or more of them in combination. Alternatively, the acetal and ketal derivative, the carbonic ester derivative, or the long-chain carboxylic ester derivative of the present invention may be used, as it is, as a cooling sensation agent composition, or may be used as a form of solution dissolved in a solvent such as alcohol, propylene glycol or benzyl benzoate, or as a form of emulsion mixed with an emulsifier.

In addition, combination use of at least one of the acetal and ketal derivative, a carbonic ester derivative, and the long-chain carboxylic ester derivative of the present invention with at least one of other cooling sensation substances not included in the compound of the invention as a cooling sensation agent component is effective in producing a cooling sensation agent composition higher in cooling efficiency.

Examples of the cooling sensation substances other than the acetal and ketal derivatives, the carbonic ester derivatives, and the long-chain carboxylic ester derivatives of the present invention include menthol, menthone, camphor, pulegol, isopulegol, cineol, mint oil, peppermint oil, spearmint oil, eucalyptus oil, 3-(1-menthoxy)propan-1,2-diol, N-alkyl-p-menthane-3-carboxamides, 2-methyl-3-(1-menthoxy)propan-1,2-diol, p-menthan-3,8-diol, 2-(1-menthoxy)ethan-1-ol, 3-(1-menthoxy)propan-1-ol, 4-(1-menthoxy)butan-1-ol, menthyl 3-hydroxybutanoate, menthyl lactate, menthol glycerol ketal, N-methyl-2,2-isopropylmethyl-3-methylbutaneamide, menthyl glyoxylate, and the like. These substances may be used alone or as a mixture of two or more, as needed.

The acetal and ketal derivative, the carbonic ester derivative, or the long-chain carboxylic ester derivative of the present invention and the cooling sensation substance other than above that can be used at any rate, as long as the advantageous effects of the present invention are obtained. The ratio of these derivatives, i.e., the ratio of (the acetal and ketal derivative, the carbonic ester derivative, or the long-chain carboxylic ester derivative of the present invention):(the cooling sensation substance other than that above) is preferably in the range of 1:99 to 70:30 by mass.

The cooling sensation agent composition of the invention described above has strong, long-lasting cooling action. Therefore, a sensory stimulation agent composition having cooling action is produced by addition of a cooling sensation agent composition of the invention. The sensory stimulation agent composition of the invention is a composition having an action to stimulate senses. The sense-stimulating actions include both cooling action and warming action, and thus in the present invention, the sensory stimulation agent composition used here is a concept including both the cooling sensation agent composition and warming and pungent agent composition.

In preparing a sensory stimulation agent composition, the field and the method of application of the cooling sensation agent composition should be altered properly according to the kind and application of the product, but the cooling sensation agent composition is normally used in a compounding amount at a concentration of 0.0001 to 20% by mass, particularly preferably of 0.001 to 5% by mass, in the entire sensory stimulation agent composition.

The sensory stimulation agent composition can be prepared by using a warming and pungent agent substance in combination with the cooling sensation agent composition of the invention. Examples of the warming substances include vanillyl ethyl ether, vanillyl propyl ether, vanillin propylene glycol acetal, ethylvanillin propylene glycol acetal, capsaicin, gingerol, vanillyl butyl ether, 4-(1-menthoxymethyl)-2-(3'-methoxy-4'-hydroxyphenyl)-1,3-dioxolane, pepper oil, pepper oleoresin, ginger oleoresin, nonylic acid vanillyl amide, jamboo oleoresin, *Zanthoxylum Piperitum* Peel Extract, sanshool-I, sanshool-II, sanshoamide, black pepper extract, chavicine, piperine, spilanthol, and the like. These substances may be used alone or as a mixture in combination of two or more.

If the cooling action is desirable, the compounding ratio of the warming and pungent agent substance to the cooling sensation substance is in the range that the warming action by the warming substance is not distinctively observed by compounding of the warming substance, and thus, the compounding amount thereof is normally 0.001 to 0.95 part, preferably 0.01 to 0.5 part, with respect to the total amount of the cooling sensation agent composition. In this case, the cooling action is further improved and strengthened by addition of the warming and pungent agent substance to the cooling sensation agent composition in the amount described above in the sensory stimulation agent composition of the present invention. Alternatively if the warming action is desirable, the cooling sensation agent composition is added to a warming composition in an amount not distinctively showing the cooling action by the cooling sensation agent composition compounded, and the compounding amount is normally 0.001 to 0.95 part, preferably 0.01 to 0.5 part by mass, with respect to the total amount of the warming and pungent agent.

The cooling sensation agent composition and the sensory stimulation agent composition of the invention can be compounded with a flavor or fragrance composition. When the cooling sensation agent composition or the sensory stimulation agent composition is compounded with the flavor or fragrance composition, the compounding amount thereof should be altered properly according to the scope, application method, kind and purpose of use of the flavor or fragrance composition, but the compounding amount is preferred in the range of normally 0.0001 to 90% by mass with respect to the total amount of the flavor or fragrance composition. In addition, the cooling sensation agent composition and the sensory stimulation agent composition of the present invention can be used in compounded flavor or fragrance composition, beverage or food products, perfume or cosmetic products, toiletry products, daily utensil products and groceries, medicines and others. If the cooling sensation agent composition or the sensory stimulation agent composition is compounded in such a product, the compounding amount thereof may vary according to the kind of the product to be compounded, but is preferably $1\times10^{-7}$ to 20% by mass, more preferably 0.0001 to 20% by mass, particularly preferably 0.001 to 5% by mass, with respect to the total amount of the product composition. The products can be applied directly on skin or scalp, administered into oral cavity, or applied onto fibers or clothes. Especially when the cooling sensation agent composition of the present invention is used, the cooling sensation agent composition, which has strong, long-lasting cooling action, provides the skin, scalp, or oral cavity with long-lasting cool feeling. Alternatively, the cooling sensation agent composition or the sensory stimulation agent composition can be used in processing of fibers, clothes, resins and the like. The compounding amount thereof should be altered properly according to the application scope, purpose of use, kind and application method of the product and others, but is normally in concentration of 0.0001 to 20% by mass, particularly preferably 0.001 to 5% by mass.

For example, the cooling sensation agent composition or the sensory stimulation agent composition of the present invention may be directly sprayed on, adsorbed in or permeated to the fibers or closing materials such as clothes, or may be used for modification or processing of the fiber surface or internal region of the fiber or the resin surface by using a suitable solvent, a dispersion medium, or microcapsules. The compounding amount thereof is preferably 0.0001 to 100% by mass, particularly preferably 0.001 to 100% by mass with respect to the total amount of the fragrance composition, the processing agent composition or the internal composition in the microcapsule.

The fiber material to be processed is not particularly limited, and examples thereof include natural fibers such as cellulose, cotton, hemp, silk and wool; regenerated fibers such as rayon, cupra, polynosic, Tencel (trade name), and Lyocell (trade name); semi-synthetic fibers such as acetates; chemical synthetic fibers such as nylon, polyester, and acrylic; and the like. These fibers may be used alone or, for example, as a mixture or combined weave fiber in combination of two or more. The forms of the fibers include yarn, woven and knitted fabrics, nonwoven fabric, paper and the like, but are not particularly limited thereto.

Wall materials of the microcapsule is preferably an organic material, and examples thereof include polystyrene, ethylcellulose, polyamide, polyacrylic acid, melamine, silicone resin and the like, but are not limited thereto.

The average particle diameter of the microcapsule is not particularly limited, but preferably 20 μm or less, more preferably 10 μm or less, still more preferably 5 μm or less, because of dispersibility when used as a processing solution, prevention of breakage of microcapsules under pressure during processing as they are adhered to fibers, and prevention of hardening in texture.

The method of producing the microcapsule is not particularly limited and includes known methods, for example those described in JP-A Nos. 62-1452, 62-45680, 62-149334, 62-225241, 63-115718, 63-217196, and 2-258052, JP No. 3059558 and others.

The adhesion methods of the microcapsule-dispersed processing solution to fibers or resins include, for example, a pad drying method, a spraying method, a printing method, a coating method and the like, but are not particularly limited thereto.

The cooling sensation agent composition and the sensory stimulation agent composition of the present invention may be compounded directly with various products such as flavor or fragrance compositions, beverage or food products, perfume or cosmetic products, toiletry products, daily utensil products and groceries, fibers, fiber products, clothes and medicines. In addition, the cooling sensation agent composition and the sensory stimulation agent composition may be first compounded with a flavor or fragrance composition, to give a flavor or fragrance composition containing the cooling sensation agent composition or the sensory stimulation agent composition, and then, the cooling sensation agent composition, the sensory stimulation agent composition, or the flavor or fragrance composition containing the cooling sensation agent composition or the sensory stimulation agent composition may be compounded with the product.

Examples of the flavor or fragrance components contained in combination with the cooling sensation agent composition and the sensory stimulation agent composition of the present invention include various synthesis aromachemicals, natural essential oils, synthetic essential oils, citrus oils, animal aromachemicals and the like, and there also may be used various kinds of flavor or fragrance components such as those described, for example, in "Collection of Well-known Prior Arts (Flavor or Fragrances) 1st Ed." (Jan. 29, 1999, Japanese Patent Office). Typical examples thereof include α-pinene, limonene, cis-3-hexenol, phenylethyl alcohol, styralyl acetate, eugenol, Oxyde de rose, linalool, benzaldehyde, muscone, Musk T (Takasago International Corp.), Thesaron (Takasago International Corp.) and the like.

The content of the cooling sensation agent composition or the sensory stimulation agent composition in the flavor or fragrance composition containing the cooling sensation agent composition or the sensory stimulation agent composition of the present invention is adjusted according to the kind and purpose of use of the flavor or fragrance and other components compounded in combination. For example, generally in the flavor or fragrance composition, the content of the cooling sensation agent composition is preferably 0.0001 to 50% by mass, more preferably 0.001 to 50% by mass, and particularly preferably 0.01 to 20% by mass, with respect to the total mass of the flavor and fragrance composition.

Alternatively, generally in the flavor composition for beverage, the content of the cooling sensation agent composition is preferably 0.0001 to 50% by mass, more preferably 0.001 to 30% by mass, with respect to the total mass of the flavor composition.

The cooling sensation agent composition and the sensory stimulation agent composition of the present invention may contain, as needed, one or more odorant-retaining agents commonly used in flavor or fragrance compositions. Example of the odorant-retaining agents used include ethylene glycol, propylene glycol, dipropylene glycol, glycerol, hexyl glycol, benzyl benzoate, triethyl citrate, diethyl phthalate, hercolin, medium-chain fatty acid triglycerides, medium-chain fatty acid diglycerides and the like. These compounds may be contained alone or in combination of two or more.

The cooling sensation agent composition and the sensory stimulation agent composition of the present invention can be used for providing cooling action to various products, as described above, by using the cooling sensation agent composition alone or as a flavor or fragrance containing the cooling sensation agent composition. The products provided with the cooling action by using the cooling sensation agent composition itself or the flavor or fragrance composition containing the cooling sensation agent composition of the present invention include beverage or food products, perfume or cosmetic products, daily utensil products and groceries, toiletry products, fibers, fiber products, clothes, medicines and the like, as described above.

Examples of the beverage or food products of the invention capable of being endowed with the cooling sensation or the like by the cooling sensation agent composition, the sensory stimulant composition or the flavor composition containing these composition include beverages such as fruit beverages, fruit spirits, milk-based drinks, carbonated drinks, soft drinks and health and nutrient drinks; frozen deserts such as ice creams, sherbets and popsicles; deserts such as jelly and puddings; confectionary such as cakes, cookies, chocolates and chewing gums; Japanese sweets such as bean-jam buns, thick jellied sweet made of azuki bean paste and thick jellied sweet made of powdered rice paste; jams; candies; breads; tea drinks and other favorite drinks such as green tea, oolong tea, black tea, persimmon leaf tea, chamomile tea, sasa veitchii tea, mulberry leaf tea, Houttuynia cordata tea, puaar tea, mate tea, rooibos tea, gymnema tea, guava tea, coffee and cocoa; soups such as Japanese style soups, Western style soups and Chinese style soups; flavored seasonings; various instant drinks and foods; various snacks; and oral products such as toothpaste, tooth powder, oral wash, mouth wash, throat lozenge, and chewing gums.

Examples of the perfume or cosmetic products, toiletry products or daily utensil products and groceries of the invention capable of being endowed with the cooling sensation or the like by the cooling sensation agent composition, the sensory stimulant composition or the fragrance composition containing these composition include perfume or cosmetic products, skin-care cosmetics, make-up cosmetics, hair cosmetics, anti-sunburn cosmetics, medicinal cosmetics, hair-care products, soaps, body lotions, bath utensils, detergents, soft finishing agents, cleaning agents, kitchen detergents, breaching agents, aerosol agents, deodorant-aromatics, repellents, and other groceries.

More specifically, the examples include:

perfume, Eau de Parfum, Eau de Toilette, and Eau de Cologne as the perfume or cosmetic products;

face washing cream, vanishing cream, cleansing cream, cold cream, massage cream, milky lotion, skin lotion, beauty wash, beauty pack, and make-up remover as skin-care cosmetics;

foundation, face powder, pressed powder, talcum powder, rouge, lip stick, lip cream, cheek rouge, eye liner, mascara, eye shadow, eyebrow-color, eye pack, nail enamel, and enamel remover as make-up cosmetics; and pomade, brilliantine, set lotion, hair stick, hair solid, hair oil, hair treatment, hair cream, hair tonic, hair liquid, hair spray, bandlin, hair-growing agent, and hair dye as hair cosmetics.

Examples of the anti-sunburn cosmetics include suntan products and sunscreen products;

examples of the medicinal cosmetics include antiperspirant, after-shaving lotion and gel, permanent wave agent, medicinal soap, medicinal shampoo, and medicinal skin-care cosmetics.

Examples of the hair-care products include shampoo, rinse, rinse-in-shampoo, hair conditioner, hair treatment, and hair pack;

examples of the soaps include toilet soap, bath soap, perfume soap, clear soap, and synthetic soap;

examples of the body cleaners include body soap, body shampoo, and hand soap; examples of the bath utensils include bath agent such as bath salt, bath tablet and bath liquid, foam bath such as bubble bath, bath oil such as bath perfume and bath capsule, milk bath, bath jelly, and bath cube; and examples of the detergents include heavy detergent for clothes, light detergent for clothes, liquid laundry detergent, laundry soap, compact detergent, and powder detergent.

Examples the soft finishing agents include softener and furniture care;

examples of the cleaning agents include cleanser, house wash, toilet cleaner, bath cleaner, glass cleaner, fungicide, and cleaner for drain pipe;

examples of the kitchen detergents include kitchen soap, kitchen synthetic soap, and dish wash;

examples of the bleaching agents include oxidant bleach such as chlorine bleach and oxygen bleach, reductive bleach such as sulfur containing bleach, and optical bleach;

examples of the aerosol agents include spray type aerosol and powder spray;

examples of the deodorant-aromatics include solid, gel and liquid deodorizer and aromatics; and examples of the groceries include tissue paper and toilet paper.

Examples of the medicines of the invention capable of being endowed with the cooling sensation or the like by the cooling sensation agent composition, the sensory stimulant composition or the flavor or fragrance composition containing these composition include, but are not limited to, skin external preparations such as poultice and ointment, internal preparations and the like.

When the cooling sensation agent composition, the sensory stimulation agent composition or the flavor or fragrance composition containing these compositions according to the invention is used for providing the aforementioned various products with cooling sensation or the like, they may be added various forms or various methods according to the kind of the products and final product forms such as liquid, solid, powder, gel, mist, aerosol, or the like. For example, they may be added directly to the product; as liquid dissolved in a polyvalent alcohol such as alcohol, propylene glycol, or glycerol; as solution or dispersion dissolved or dispersed with a natural gum such as gum arabic or tragacanth gum or a surfactant (e.g., nonionic surfactant such as glycerol fatty acid ester or sucrose fatty acid ester, anionic surfactant, cationic surfactant and amphoteric surfactant); as powder formed with a natural gum such as gum arabic or a diluent such as gelatin or dextrin; or as microcapsules treated with an encapsulating agent.

Alternatively, the cooling sensation agent composition, the sensory stimulation agent composition or the flavor or fragrance composition containing these may be stabilized and provided with sustained-release property, by inclusion with an inclusion agent such as cyclodextrin.

EXAMPLES

Hereinafter, the present invention will be described specifically with reference to Examples, but it should be understood that the present invention is not restricted by these Examples, and various modifications are possible within the scope of the present invention.

The products obtained in the Preparative Examples and Examples described below were analyzed by using the following instruments and apparatuses:

Nuclear magnetic resonance spectrum: $^1$H NMR: AM-400 (400 MHz)
(manufactured by Bruker)
External standard substance: tetramethylsilane
Infrared absorption spectra (IR-KBr and IR-NaCl): Nicolet AVATAR 360FT-IR
Gas chromatograph (GC): HP6890 (manufactured by HEWLETT PACKARD)
Column: NEUTRABOND-1 (manufactured by GL Science Inc.)
(Internal diameter×length: 0.25 mm×30 m)
Mass spectrum (MS): M-80 Mass spectrometric analyzer (manufactured by Hitachi Ltd., ionization voltage: 20 eV)
Melting point analyzer: Yanagimoto Mfg., melting point analyzer
(open type)

Preparative Example 1

Preparation of di-1-menthyl carbonate

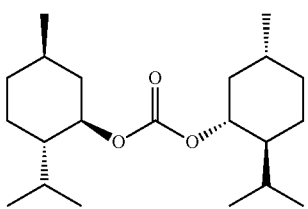 [SMILES: CC(C)[C@@H]1CC[C@@H](C)C[C@H]1OC(=O)O[C@@H]1C[C@H](C)CC[C@H]1C(C)C]

35.7 g of 1-menthol (molecular weight: 156.27, 228.6 mmol), 27.1 g of pyridine (molecular weight: 79.10, 342.9 mmol) and 50 ml of tetrahydrofuran were placed in a 300-ml reaction flask equipped with a thermometer; the mixture was kept at 20° C. or lower while cooled in a water bath; a solution of 50.0 g of chloromenthyl carbonate (molecular weight 218.73, 228.6 mmol) in tetrahydrofuran (50 ml) was added dropwise thereto under nitrogen stream over a 1 hour period. The mixture was stirred for 2 hours after dropwise addition, and then the reaction solution obtained was quenched in water and extracted with toluene. The toluene phase was washed thrice with dilute hydrochloric acid, and then, washed with aqueous sodium carbonate solution, aqueous ammonium chloride solution, and aqueous saturated sodium chloride solution sequentially, dried over anhydrous magnesium sulfate, filtered, and condensed in rotary evaporator for removal of the solvent to give yellow oil. It was then recrystallized from hexane to give desired di-1-menthyl carbonate as colorless powder. Yield 66.9 g, (molecular weight: 338.54, 197.5 mmol), purity: 100%, yield: 86.4%, melting point: 101 to 102° C.

$^1$H NMR (500 MHz, CDCl$_3$, δ) ppm: 0.80 (d, J=7.0 Hz, 3H), 0.80-1.00 (m, 2H), 0.90 (d, J=7.0 Hz, 3H), 0.92 (d, J=6.5 Hz, 3H), 1.00-1.13 (m, 4H), 1.38-1.45 (m, 2H), 1.44-1.59 (m, 2H), 1.64-1.73 (m, 4H), 1.90-2.01 (m, 2H), 2.01-2.10 (m, 2H), 4.48-4.68 (m, 2H).

IR (KBr) cm$^{-1}$: 2956, 2867, 1735, 1465, 1385, 1370, 1345, 1326, 1288, 1260, 1182, 1153, 1097, 1080, 1038, 1010, 980, 956, 914, 844, 790.

MS (m/z): 281, 233, 199, 185, 155, 138, 123, 109, 95, 83, 81, 64, 57, 55, 43, 41.

Preparative Example 2

Preparation of di-1-isopulegol carbonate

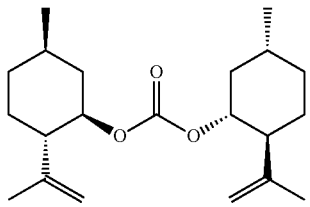 [SMILES: C=C(C)[C@@H]1CC[C@@H](C)C[C@H]1OC(=O)O[C@@H]1C[C@H](C)CC[C@H]1C(=C)C]

80.0 g of 1-isopulegol (molecular weight: 154.25, 518.6 mmol), 45.1 g of pyridine (molecular weight 79.10, 570.5 mmol) and 300 ml of toluene were placed in a 1-L reaction flask equipped with a thermometer; the mixture was kept at 20° C. or lower while cooled in a water bath; a solution of 25.7 g of triphosgene (molecular weight 296.75, 86.4 mmol) in toluene (200 ml) was added dropwise thereto under nitrogen stream over a 1 hour period. The mixture was stirred for 2 hours after dropwise addition and then the reaction solution obtained was quenched in water and extracted with toluene. The toluene phase was washed thrice with dilute hydrochloric acid, and then, washed with aqueous sodium carbonate solution, aqueous ammonium chloride solution, and aqueous saturated sodium chloride solution sequentially, dried over anhydrous sodium sulfate, filtered, and condensed in rotary evaporator for removal of the solvent to give a colorless solid. It was then recrystallized from hexane to give desired di-1-isopulegol carbonate as colorless powder. Yield 82.8 g, (molecular weight: 334.50, 247.4 mmol), purity: 100%, yield: 95.4%, melting point: 86 to 87° C.

$^1$H NMR (500 MHz, CDCl$_3$, δ) ppm: 0.87-0.99 (m, 2H), 0.92 (d, J=6.5 Hz, 3H), 1.02-1.13 (m, 2H), 1.30-1.42 (m, 2H), 1.47-1.59 (m, 3H), 1.62-1.77 (m, 3H), 1.69 (s, 6H), 1.95-2.04 (m, 2H), 2.08-2.17 (m, 2H), 4.57-4.65 (m, 2H), 4.72-4.78 (m, 4H).

IR (KBr) cm$^{-1}$: 2949, 2616, 2862, 1731, 1648, 1455, 1381, 1357, 1259, 1175, 1132, 1107, 1086, 1047, 1013, 972, 958, 921, 884, 844.

MS (m/z): 334, 272, 257, 239, 229, 215, 199, 189, 175, 161, 149, 136, 121, 107, 95, 93, 81, 69, 67, 55, 43, 41.

Preparative Example 3

Preparation of 1-menthyl-1-menthoxy ethyl carbonate

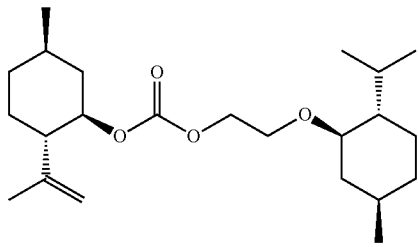 [SMILES: C=C(C)[C@@H]1CC[C@@H](C)C[C@H]1OC(=O)OCCO[C@@H]1C[C@H](C)CC[C@H]1C(C)C]

37.5 g of 1-menthoxy ethanol (molecular weight: 200.32, 187.2 mmol), 24.4 g of pyridine (molecular weight: 79.10, 308.6 mmol) and 50 ml of tetrahydrofuran were placed in a 300-ml reaction flask equipped with a thermometer; the mixture was kept at 20° C. or lower while cooled in a water bath; a solution of 45.0 g of chloromenthyl carbonate (molecular weight 218.73, 205.7 mmol) in tetrahydrofuran (50 ml) was added dropwise thereto under nitrogen stream over a 1 hour period. The mixture was stirred for 2 hours after dropwise addition. The reaction solution obtained was quenched in water and extracted with toluene. The toluene phase was washed thrice with dilute hydrochloric acid, and then, washed with aqueous sodium carbonate solution, aqueous ammonium chloride solution, and aqueous saturated sodium chloride solution sequentially, dried over anhydrous magnesium sulfate, filtered, and condensed in rotary evaporator for removal of the solvent to give pale yellow oil. Distillation thereof under reduced pressure gave a desired product, 1-menthyl-1-menthoxy ethyl carbonate as colorless oil. Yield: 62.7 g, (molecular weight: 382.59, 163.9 mmol), purity: 99.8%, yield: 87.5%, boiling point: 167° C. (10 Pa).

$^1$H NMR (500 MHz, CDCl$_3$, δ) ppm: 0.73-0.80 (m, 6H), 0.76-0.96 (m, 2H), 0.85-0.91 (m, 12H), 0.96-1.11 (m, 2H), 1.18-1.25 (m, 1H), 1.27-1.54 (m, 3H), 1.91-2.13 (m, 1H), 2.13-2.11 (m, 2H), 2.13-2.24 (m, 1H), 3.02-3.12 (m, 1H), 3.52-3.60 (m, 1H), 3.77-3.85 (m, 1H), 4.18-4.28 (m, 2H), 4.46-4.57 (m, 1H).

IR (NaCl) cm$^{-1}$: 2954, 2925, 2869, 1741, 1455, 1385, 1373, 1343, 1261, 1181, 1113, 1040, 1017, 996, 980, 960, 921, 888, 845, 790.

MS (m/z): 383, 312, 297, 281, 243, 227, 209, 201, 199, 184, 180, 155, 139, 123, 109, 107, 97, 95, 89, 83, 81, 71, 69, 57, 55, 43, 41.

Preparative Example 4

Preparation of di-1-menthoxy ethyl carbonate

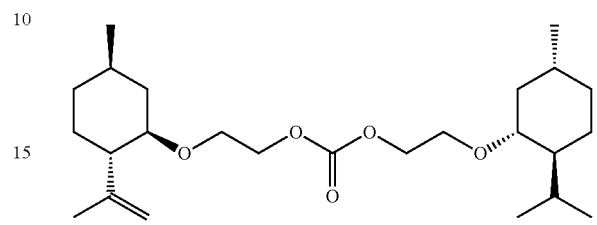

80.0 g of 1-menthoxy ethanol (molecular weight: 200.32, 399.4 mmol), 34.7 g of pyridine (molecular weight: 79.10, 439.3 mmol) and 300 ml of toluene were placed in a 1-L reaction flask equipped with a thermometer; the mixture was kept at 20° C. or lower while cooled in a water bath; a solution of 12.3 g of triphosgene (molecular weight: 296.75, 41.6 mmol) in toluene (200 ml) was added dropwise thereto under nitrogen stream over 1 hour period. The mixture was stirred for 2 hours after dropwise addition; the reaction solution obtained was quenched in water and extracted with toluene; the toluene phase was washed thrice with dilute hydrochloric acid, and then, washed with aqueous sodium carbonate solution, aqueous ammonium chloride solution, and aqueous saturated sodium chloride solution sequentially, dried over anhydrous sodium sulfate, filtered, and condensed in rotary evaporator for removal of the solvent, to give a pale yellow oil. Distillation thereof under reduced pressure gave a desired product, di-1-menthoxy ethyl carbonate as colorless oil. Yield: 75.1 g, (molecular weight: 426.64, 176.1 mmol), purity: 99.6%, yield: 88.2%, boiling point: 167 to 171° C. (10 Pa).

$^1$H NMR (500 MHz, CDCl$_3$, δ) ppm: 0.76 (d, J=6.9 Hz, 3H), 0.88 (d, J=7.0 Hz, 3H), 0.91 (d, J=6.5 Hz, 3H), 0.78-1.04 (m, 3H), 1.18-1.28 (m, 1H), 1.28-1.42 (m, 1H), 1.57-1.72 (m, 2H), 2.03-1.13 (m, 1H), 2.13-2.27 (m, 1H), 1.18-1.28 (m, 1H), 3.03-3.12 (m, 1H), 3.51-3.60 (m, 1H), 3.78-3.86 (m, 1H), 4.20-4.33 (m, 2H).

IR (NaCl) cm$^{-1}$: 2954, 2922, 2869, 1749, 1455, 1385, 1343, 1262, 1181, 1112, 1024, 998, 978, 924, 891, 861, 790.

MS (m/e): 341, 287, 272, 245, 243, 227, 215, 203, 183, 155, 151, 139, 134, 123, 107, 97, 95, 89, 83, 81, 69, 57, 55, 43, 41.

Preparative Example 5

Preparation of 1-menthyl-1-isopulegol carbonate

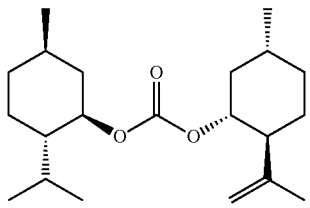 [SMILES: C=C(C)[C@@H]1CC[C@@H](C)C[C@H]1OC(=O)O[C@@H]1C[C@H](C)CC[C@H]1C(C)C]

28.9 g of 1-isopulegol (molecular weight: 154.25, 187.4 mmol), 24.4 g of pyridine (molecular weight: 79.10, 308.6 mmol) and 50 ml of tetrahydrofuran were placed in a 300-ml reaction flask equipped with a thermometer. The mixture was kept at 20° C. or lower while cooled in a water bath. A solution of 45.0 g chloromenthyl carbonate (molecular weight 218.73, 205.7 mmol) in tetrahydrofuran (50 ml) was added dropwise thereto under nitrogen stream over 1 hour period. The mixture was stirred for 2 hours after dropwise addition. The reaction solution obtained was quenched in water and extracted with toluene. The toluene phase was washed thrice with dilute hydrochloric acid, and then, washed with aqueous sodium carbonate solution, aqueous ammonium chloride solution, and aqueous saturated sodium chloride solution sequentially, dried over anhydrous magnesium sulfate, filtered, and condensed in rotary evaporator for removal of the solvent to give a yellow solid. It was then recrystallized from hexane to give a desired product, 1-menthyl-1-isopulegol carbonate as colorless powder. Yield: 54.0 g, (molecular weight: 336.52, 160.6 mmol), purity: 100%, yield: 85.7%, boiling point: 107 to 108° C.

$^1$H NMR (500 MHz, CDCl$_3$, δ) ppm: 0.77 (d, J=6.9 Hz, 3H), 0.70-1.00 (m, 2H), 0.88 (d, J=7.1 Hz, 3H), 0.91 (d, J=6.6 Hz, 3H), 0.95 (d, J=6.6 Hz, 3H), 1.00-1.08 (m, 2H), 1.08-1.19 (m, 1H), 1.30-1.63 (m, 4H), 1.63-1.78 (m, 4H), 1.69 (s, 3H), 1.86-2.02 (m, 2H), 2.02-2.10 (m, 1H), 2.10-2.20 (m, 1H), 4.42-4.53 (m, 1H), 4.61-4.70 (m, 1H), 4.75-4.83 (m, 2H).

IR (KBr) cm$^{-1}$: 2951, 2931, 2865, 1735, 1685, 1648, 1457, 1370, 1350, 1324, 1292, 1269, 1180, 1154, 1134, 1096, 1082, 1039, 1010, 972, 959, 931, 917, 890, 845, 790.

MS (m/e): 336, 293, 274, 259, 231, 217, 199, 177, 154, 136, 123, 121, 107, 95, 83, 81, 69, 67, 57, 55, 43, 41.

Preparative Example 6

Preparation of 1-menthoxypropanediol methylheptenone ketal

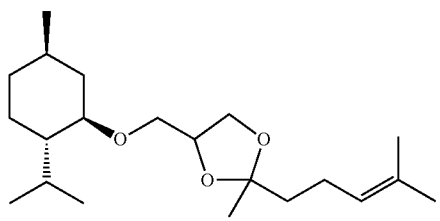 [SMILES: CC(C)=CCCC1(C)OCC(CO[C@@H]2C[C@H](C)CC[C@H]2C(C)C)O1]

100.0 g of 1-menthoxypropanediol (molecular weight: 230.35, 434.1 mmol), 54.8 g of methylheptenone (molecular weight: 126.20, 434.1 mmol), 1.0 g p-toluenesulfonic acid monohydrate (molecular weight: 190.22, 5.2 mmol), and 300 ml of toluene were placed in a 1-L reaction flask equipped with a thermometer, a Dean-Stark trap, and a reflux condenser. The mixture was heated at an oil bath temperature of 140° C. and additionally under reflux for two hours while water generated during reflux was removed. The reaction solution obtained after cooling was quenched in aqueous sodium carbonate solution and extracted with toluene. The toluene phase was washed with aqueous saturated sodium chloride solution, dried over anhydrous sodium sulfate, filtered, and condensed in rotary evaporator for removal of the solvent to give pale yellow oil. Distillation thereof under reduced pressure gave a desired product, 1-menthoxypropanediol methylheptenone ketal as colorless oil. Yield: 136.1 g, (molecular weight: 338.54, 402.0 mmol), purity: 100%, yield: 92.6%, boiling point: 110 to 111° C. (10 Pa).

$^1$H NMR (500 MHz, CDCl$_3$, δ) ppm: 0.73-0.80 (m, 3H), 0.74-1.06 (m, 3.5H), 0.84-0.94 (m, 6H), 1.16-1.28 (m, 1H), 1.26-1.42 (m, 1H), 1.31 (s, 1.5H), 1.31 (s, 1.5H), 1.36 (s, 1.5H), 1.52-1.75 (m, 3.5H), 1.61 (s, 3H), 1.68 (s, 3H), 1.97-2.12 (m, 3H), 2.12-2.24 (m, 1H), 3.00-3.12 (m, 1H), 3.20-3.27 (m, 0.5H), 3.41-3.48 (m, 0.5H), 3.51-3.57 (m, 0.5H), 3.63-3.72 (m, 0.5H), 3.71-3.78 (m, 1H), 4.03-4.11 (m, 1H), 4.15-4.22 (m, 0.5H), 4.22-4.29 (m, 0.5H), 5.07-5.16 (m, 1H).

IR (NaCl) cm$^{-1}$: 2954, 2923, 2869, 1453, 1375, 1342, 1239, 1201, 1182, 1109, 1074, 1054, 919, 876, 844.

MS (m/z): 338, 323, 281, 267, 255, 231, 213, 199, 185, 169, 155, 139, 108, 97, 83, 69, 57, 55, 43, 41.

Preparative Example 8

Preparation of 1-menthoxypropanediol benzaldehyde acetal

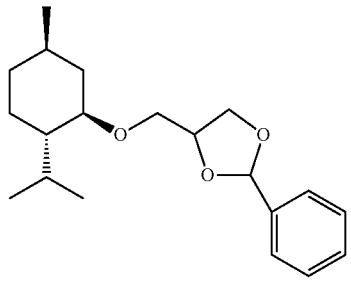 [SMILES: CC(C)[C@@H]1CC[C@@H](C)C[C@H]1OCC1COC(c2ccccc2)O1]

100.0 g of 1-menthoxypropanediol (molecular weight: 230.35, 434.1 mmol), 46.1 g of benzaldehyde (molecular weight: 106.13, 434.1 mmol), 1.0 g p-toluenesulfonic acid monohydrate (molecular weight: 190.22, 5.2 mmol), and 300 ml of toluene were placed in a 1-L reaction flask equipped with a thermometer, a Dean-Stark trap, and a reflux condenser. The mixture was heated at an oil bath temperature of 140° C. and additionally under reflux for two hours while water generated during reflux was removed. The reaction solution obtained after cooling was quenched in aqueous sodium carbonate solution and extracted with toluene. The toluene phase was washed with aqueous saturated sodium chloride solution, dried over anhydrous sodium sulfate, filtered, and condensed in rotary evaporator for removal of the solvent to give pale yellow oil. Distillation thereof under reduced pressure gave a desired product, 1-menthoxypropanediol benzaldehyde acetal as colorless oil. Yield: 130.1 g, (molecular weight: 318.46, 408.5 mmol), purity: 100%, yield: 94.1%, boiling point: 155 to 158° C. (60 Pa).

$^1$H NMR (500 MHz, CDCl$_3$, δ) ppm: 0.73-0.81 (m, 3H), 0.78-1.10 (m, 3H), 0.85-0.94 (m, 6H), 1.18-1.29 (m, 1H), 1.27-1.41 (m, 1H), 1.57-1.70 (m, 2H), 2.04-2.16 (m, 1H), 2.13-2.28 (m, 1H), 0.73-0.81 (m, 3H), 3.03-3.14 (m, 1H), 3.30-3.44 (m, 0.5H), 3.52-3.56 (m, 0.5H), 3.62-3.77 (m, 0.5H), 3.81-3.89 (m, 1H), 0.73-0.81 (m, 3H), 3.95-4.00 (m, 0.5H), 4.06-4.13 (m, 0.5H), 4.21-4.27 (m, 0.5H), 4.32-4.42 (m, 1H), 5.80 (d, J=2.0 Hz, 0.5H), 5.93 (d, J=5.2 Hz, 0.5H), 7.31-7.42 (m, 3H), 7.42-7.53 (m, 2H).

IR (NaCl) cm$^{-1}$: 2953, 2922, 2869, 1456, 1387, 1370, 1341, 1312, 1219, 1179, 1095, 1067, 1028, 974, 916, 846, 758, 698.

MS (m/z): 318, 303, 275, 261, 245, 233, 197, 179, 164, 149, 139, 123, 107, 105, 91, 83, 69, 57, 55, 43, 41.

Preparative Example 8

Preparation of 1-menthoxypropanediol-1-citronellal acetal

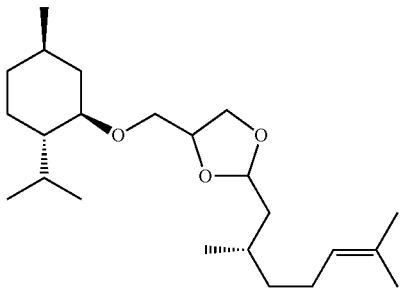 [SMILES: CC(C)=CCC[C@H](C)CC1OCC(CO[C@@H]2C[C@H](C)CC[C@H]2C(C)C)O1]

100.0 g of 1-menthoxypropanediol (molecular weight: 230.35, 434.1 mmol), 67.0 g of 1-citronellal (molecular weight: 154.25, 434.1 mmol), 1.0 g of p-toluenesulfonic acid monohydrate (molecular weight: 190.22, 5.2 mmol), and 300 ml of toluene were placed in a 1-L reaction flask equipped with a thermometer, a Dean-Stark trap, and a reflux condenser. The mixture was heated at an oil bath temperature of 140° C. and additionally under reflux for two hours while water generated during reflux was removed. The reaction solution obtained after cooling was quenched in aqueous sodium carbonate solution and extracted with toluene. The toluene phase was washed with aqueous saturated sodium chloride solution, dried over anhydrous sodium sulfate, filtered, and condensed in rotary evaporator for removal of the solvent to give pale yellow oil. Distillation thereof under reduced pressure gave a desired product, 1-menthoxypropanediol-1-citronellal acetal as colorless oil. Yield: 147.7 g, (molecular weight: 366.59, 402.9 mmol), purity: 99.8%, yield: 92.8%, boiling point: 167 to 168° C. (60 Pa).

$^1$H NMR (500 MHz, CDCl$_3$, δ) ppm: 0.73-0.81 (m, 3H), 0.73-1.05 (m, 3H), 0.85-0.96 (m, 9H), 1.13-1.28 (m, 2H), 1.28-1.42 (m, 2H), 1.43-1.57 (m, 1H), 1.57-1.74 (m, 4H), 1.60 (s, 3H), 1.67 (s, 3H), 1.90-2.06 (m, 2H), 2.03-2.12 (m, 1H), 2.11-2.24 (m, 1H), 3.02-3.12 (m, 1H), 3.18-3.32 (m, 0.5H), 3.40-3.47 (m, 0.5H), 3.48-3.61 (m, 0.5H), 3.60-3.67 (m, 0.5H), 3.68-3.82 (m, 1H), 3.84-3.92 (m, 0.5H), 4.08-4.18 (m, 1H), 4.15-4.26 (m, 0.5H), 4.90-4.95 (m, 0.5H), 5.00-5.05 (m, 0.5H), 5.06-5.14 (m, 1H).

IR (NaCl) cm$^{-1}$: 2955, 2921, 2869, 1454, 1412, 1378, 1343, 1238, 1134, 1109, 1043, 975, 920, 838.

MS (m/z): 366, 351, 323, 309, 295, 281, 267, 241, 227, 213, 197, 185, 167, 143, 139, 136, 121, 109, 97, 95, 83, 81, 69, 57, 55, 43, 41.

Preparative Example 9

Preparation of 1-menthyl isostearate 284.5 g of isostearic acid (molecular weight: 284.49, 1.00 mol) and thionyl chloride (molecular weight: 118.97, 1.05 mol) were placed in a 1-L reaction flask equipped with a thermometer. The mixture was stirred at room temperature for 20 minutes and then, heated at an oil bath temperature of 40° C. and stirred for 1 hour. The reaction solution obtained was left under reduced pressure for removal of the dissolved gas and excess thionyl chloride. 300 ml of toluene and 156.3 g of 1-menthol (molecular weight: 156.27, 1.00 mol) were added thereto; and 121.4 g of triethylamine (molecular weight: 101.19, 1.20 mol) was added dropwise over 20 minutes. After dropwise addition, the mixture was stirred at an oil bath temperature of 60° C. for 3 hours. The reaction solution obtained was quenched in water and extracted with toluene. The toluene phase was washed with aqueous saturated sodium chloride solution, dried over anhydrous sodium sulfate, filtered, and condensed in rotary evaporator for removal of the solvent to give yellow oil. Distillation thereof under reduced pressure gave a desired product, isostearic acid-1-menthyl as colorless oil. Yield: 351.4 g, (molecular weight: 422.7, 831.4 mmol), purity: 99.8%, yield: 83.1%.

Example 1

Cooling Treated Towel (Direct Spraying)

1% ethanol solution of each of di-1-menthyl carbonate, di-1-isopulegol carbonate, 1-menthyl-1-menthoxy ethyl carbonate, 1-menthyl-1-isopulegol carbonate, 1-menthoxypropanediol methylheptenone ketal, 1-menthoxypropanediol benzaldehyde acetal, 1-menthoxypropanediol-1-citronellal acetal, menthyl palmitate, menthyl stearate, menthyl isostearate, 1-menthol, and an equivalent-weight mixture of 1-menthyl-menthoxy ethyl carbonate, menthoxypropanediol citronellal acetal and menthyl isostearate was prepared. The solution was sprayed on a pure cotton hand towel (white plain towel made in Japan, 20 cm×20 cm, degrease-finished) in an amount of 1 g. After the towel was air-dried for 10 minutes, 3 hours, or 24 hours, the cooling action of each towel was determined organoleptically. Results are shown in Table 1. Fifteen professional examiners with 5 years or more of experience are divided into three groups; different 5 kinds of samples were ranked from the strongest to weakest in action respectively by the examiners in three groups; and the result was shown by the sum of the ranking numbers.

TABLE 1

Results of comparison concern with lasting properties of cooling effect on treated hand towel at direct spraying

| Materials | Group A | | | Group B | | | Group C | | |
|---|---|---|---|---|---|---|---|---|---|
| | 10 min | 3 hr | 24 hr | 10 min | 3 hr | 24 hr | 10 min | 3 hr | 24 hr |
| Di-l-menthyl carbonate | 24 | 21 | 20 | 24 | 19 | 19 | 17 | 21 | 21 |
| Di-l-isopulegol carbonate | 17 | 12 | 11 | | | | | | |
| l-Menthyl-l-menthoxy ethyl carbonate | 10 | 5 | 5 | | | | | | |
| l-Menthyl-l-isopulegol carbonate | 19 | 1 | 14 | | | | | | |
| l-Menthoxypropanediol methylheptenone ketal | | | | 13 | 6 | 6 | | | |

TABLE 1-continued

Results of comparison concern with lasting properties of
cooling effect on treated hand towel at direct spraying

| Materials | Group A | | | Group B | | | Group C | | |
|---|---|---|---|---|---|---|---|---|---|
| | 10 min | 3 hr | 24 hr | 10 min | 3 hr | 24 hr | 10 min | 3 hr | 24 hr |
| l-Menthoxypropanediol benzaldehyde acetal | | | | 15 | 9 | 9 | | | |
| l-Menthoxypropanediol-1-citronellal acetal | | | | 18 | 16 | 16 | | | |
| Menthyl palmitate | | | | | | | 15 | 17 | 17 |
| Menthyl stearate | | | | | | | 21 | 15 | 17 |
| Menthyl isostearate | | | | | | | 17 | 17 | 15 |
| l-Menthol | 5 | 24 | 25 | 5 | 25 | 25 | | | |
| Mixture | | | | | | | 5 | 5 | 5 |

Numbers in Table are the sum of the ranking numbers

As obvious from the results in Table 1, menthol showed the strongest cooling action after air drying for 10 minutes, but the action was found to be less consistent. On the other hand, the carbonic ester derivatives of the present invention showed long-lasting cooling action, and in particular, 1-menthyl-menthoxy ethyl carbonate showed an action superior both in initial strength and consistency. Among the acetal and ketal derivatives, menthoxypropanediol methylheptenone ketal was strongest in action. Among the fatty acid ester derivatives, the isostearic ester showed the strongest action, which was similarly, slightly stronger than dimenthyl carbonate. The equivalent-weight mixture of 1-menthyl-menthoxy ethyl carbonate, menthoxypropanediol citronellal acetal and menthyl isostearate showed the most favorable cooling action both in initial strength and durability among the compounds above.

Example 2

Cooling Towel (Washing Processed)

Each of di-1-menthyl carbonate, di-1-isopulegol carbonate, 1-menthyl-1-menthoxy ethyl carbonate, 1-menthyl-1-isopulegol carbonate, 1-menthoxypropanediol benzaldehyde acetal, 1-menthoxypropanediol methylheptenone ketal, 1-menthoxypropanediol-1-citronellal acetal, menthyl palmitate, menthyl stearate, menthyl isostearate, 1-menthoxypropanediol, and an equivalent-weight mixture of 1-menthyl-menthoxy ethyl carbonate, menthoxypropanediol citronellal acetal and menthyl isostearate was compounded with a base washing detergent solution at a concentration of 1%.

A pure cotton hand towel (white plain towel made in Japan, 20 cm×20 cm, degrease-finished) was hand-washed for 3 minutes at a particular concentration (water: 10 L, detergent: 3 g, water temperature: 17° C.), then washed with the same amount of water for 2 minutes, squeezed lightly, and air-dried indoor for 6 hours. The hand towels prepared, the hand towels after 24 hours and the hand towels after 48 hours were brought into contact with the internal bronchia and the cooling action thereof was determined organoleptically. Results are shown in Table 2. The determination was conducted as same as Example 1, that is, five professional examiners are divided into three groups; different 5 kinds of samples were ranked from the strongest to weakest in action respectively by the examiners in three groups; and the result was shown by the sum of the ranking numbers.

TABLE 2

Results of comparison concern with lasting properties
of cooling effect on treated hand towel after washing

| Materials | Group A | | | Group B | | | Group C | | |
|---|---|---|---|---|---|---|---|---|---|
| | 6 hr | 24 hr | 48 hr | 6 hr | 24 hr | 24 hr | 6 hr | 24 hr | 48 hr |
| Di-l-menthyl carbonate | 16 | 18 | 18 | 16 | 15 | 16 | 16 | 21 | 21 |
| Di-l-isopulegol carbonate | 14 | 13 | 14 | | | | | | |
| l-Menthyl-l-menthoxy ethyl carbonate | 8 | 7 | 7 | | | | | | |
| l-Menthyl-l-isopulegol carbonate | 12 | 12 | 11 | | | | | | |
| l-Menthoxypropanediol methylheptenone ketal | | | | 10 | 11 | 10 | | | |
| l-Menthoxypropanediol benzaldehyde acetal | | | | 11 | 11 | 11 | | | |
| l-Menthoxypropanediol-1-citronellal acetal | | | | 13 | 13 | 13 | | | |
| Menthyl palmitate | | | | | | | 18 | 16 | 17 |
| Menthyl stearate | | | | | | | 21 | 18 | 17 |
| Menthyl isostearate | | | | | | | 15 | 15 | 15 |
| l-Menthol | 25 | 25 | 25 | 25 | 25 | 25 | | | |
| Mixture | | | | | | | 5 | 5 | 5 |

Numbers in Table are the sum of the ranking numbers

As obvious from the results in Table 2, 1-menthoxypropanediol did not have cooling action after washing treatment and air drying for 6 hours. Among the carbonic ester derivatives of the present invention, 1-menthyl-1-menthoxy ethyl carbonate was strongest and di-1-menthyl carbonate was weakest in action. The acetal and ketal derivatives showed a cooling action mostly at the same strength. The fatty acid ester derivatives also showed the cooling action at the same strength, but the equivalent-weight mixture of 1-menthyl-menthoxy ethyl carbonate, menthoxypropanediol citronellal acetal and menthyl isostearate showed a cooling action more favorable both in initial strength and durability among them.

Example 3

Body Shampoo 35 parts by mass of the total amount of the product obtained in the Preparative Examples, di-1-menthyl carbonate, di-1-isopulegol carbonate, 1-menthyl-1-menthoxy ethyl carbonate, di-1-menthoxy ethyl carbonate, 1-menthyl-1-isopulegol carbonate, 1-menthoxypropanediol methylheptenone ketal, 1-menthoxypropanediol benzaldehyde acetal or 1-menthoxypropanediol-1-citronellal acetal and menthyl palmitate, menthyl stearate or menthyl isostearate, and 65 parts by mass of a citrus-herbal mixed fragrance (manufactured by Takasago International Corp.) were mixed to give a sensory stimulation agent-containing fragrance composition; and body shampoos in the following compositions (compounding amount: parts by mass) were prepared by using the same. These body shampoos showed a cool and long-lasting cooling action.

Prescription of Body Shampoo

TABLE 3

Prescripiton of Body shampoo

| Ingredients | Compounding amount | | | | | | | |
|---|---|---|---|---|---|---|---|---|
| Triethanolamine | 9.00 | 9.00 | 9.00 | 9.00 | 9.00 | 9.00 | 9.00 | 9.00 |
| Lauric acid | 6.00 | 6.00 | 6.00 | 6.00 | 6.00 | 6.00 | 6.00 | 6.00 |
| Myristic acid | 9.00 | 9.00 | 9.00 | 9.00 | 9.00 | 9.00 | 9.00 | 9.00 |
| Lauryl polyoxyethylenesulfosuccinate disodium salt (1E.O.) (42%) | 10.00 | 10.00 | 10.00 | 10.00 | 10.00 | 10.00 | 10.00 | 10.00 |
| Alkyl (C8-16) glucoxide | 8.00 | 8.00 | 8.00 | 8.00 | 8.00 | 8.00 | 8.00 | 8.00 |
| Glyceryl laurate | 1.00 | 1.00 | 1.00 | 1.00 | 1.00 | 1.00 | 1.00 | 1.00 |
| 2-Hydroxyethyl distearate | 2.50 | 2.50 | 2.50 | 2.50 | 2.50 | 2.50 | 2.50 | 2.50 |
| Coconut oil fatty acid diethanol amide | 3.00 | 3.00 | 3.00 | 3.00 | 3.00 | 3.00 | 3.00 | 3.00 |
| Propylene glycol | 5.00 | 5.00 | 5.00 | 5.00 | 5.00 | 5.00 | 5.00 | 5.00 |
| Dibutylhydroxytoluene | 0.05 | 0.05 | 0.05 | 0.05 | 0.05 | 0.05 | 0.05 | 0.05 |
| Edetic acid disodium salt | 0.10 | 0.10 | 0.10 | 0.10 | 0.10 | 0.10 | 0.10 | 0.10 |
| Ethyl p-oxybenzoate | 0.20 | 0.20 | 0.20 | 0.20 | 0.20 | 0.20 | 0.20 | 0.20 |
| Methyl p-oxybenzoate | 0.10 | 0.10 | 0.10 | 0.10 | 0.10 | 0.10 | 0.10 | 0.10 |
| Fragrance composition containing sensory stimulation agent (Breakdown below) | 1.00 | 1.00 | 1.00 | 1.00 | 1.00 | 1.00 | 1.00 | 1.00 |
| Citrus herbal mixed fragrance | 0.65 | 0.65 | 0.65 | 0.65 | 0.65 | 0.65 | 0.65 | 0.65 |
| Di-l-menthyl carbonate | 0.25 | 0.00 | 0.00 | 0.00 | 0.00 | 0.00 | 0.00 | 0.00 |
| Di-l-isopulegol carbonate | 0.00 | 0.25 | 0.00 | 0.00 | 0.00 | 0.00 | 0.00 | 0.00 |
| l-Menthyl-l-menthoxy ethyl carbonate | 0.00 | 0.00 | 0.25 | 0.00 | 0.00 | 0.00 | 0.00 | 0.00 |
| Di-l-menthoxy ethyl carbonate | 0.00 | 0.00 | 0.00 | 0.25 | 0.00 | 0.00 | 0.00 | 0.00 |
| l-Menthyl-l-isopulegol carbonate | 0.00 | 0.00 | 0.00 | 0.00 | 0.25 | 0.00 | 0.00 | 0.00 |
| l-Menthoxypropanediol methylheptenone ketal | 0.00 | 0.00 | 0.00 | 0.00 | 0.00 | 0.25 | 0.00 | 0.00 |
| l-Menthoxypropanediol benzaldehyde acetal | 0.00 | 0.00 | 0.00 | 0.00 | 0.00 | 0.00 | 0.25 | 0.00 |
| l-Menthoxypropanediol-l-citronellal acetal | 0.00 | 0.00 | 0.00 | 0.00 | 0.00 | 0.00 | 0.00 | 0.25 |
| Menthyl palmitate | 0.10 | 0.10 | 0.00 | 0.00 | 0.00 | 0.00 | 0.00 | 0.10 |
| Menthyl stearate | 0.00 | 0.00 | 0.10 | 0.10 | 0.00 | 0.00 | 0.00 | 0.00 |
| Menthyl isostearate | 0.00 | 0.00 | 0.00 | 0.00 | 0.10 | 0.10 | 0.10 | 0.00 |
| Purified water (balance) | | | | | | | | |
| Total | 100.00 | 100.00 | 100.00 | 100.00 | 100.00 | 100.00 | 100.00 | 100.00 |

Example 4

Fragrance Compositions 8 kinds of fragrance compositions in Table 4 (compounding amount: parts by mass) were prepared by a common method.

<Prescription of Fragrance Composition>

TABLE 4

Prescription of Fragrance composition

| Ingredients | Compounding amount | | | | | | | |
|---|---|---|---|---|---|---|---|---|
| Apple base (manufactured by Takasago International Corp.) | 8.00 | 8.00 | 8.00 | 8.00 | 8.00 | 8.00 | 8.00 | 8.00 |
| Bergamot oil | 14.00 | 14.00 | 14.00 | 14.00 | 14.00 | 14.00 | 14.00 | 14.00 |
| Ethyl acetoacetate | 5.00 | 5.00 | 5.00 | 5.00 | 5.00 | 5.00 | 5.00 | 5.00 |
| Methyl dihydrojasmonate | 23.00 | 23.00 | 23.00 | 23.00 | 23.00 | 23.00 | 23.00 | 23.00 |
| Laurinal | 3.00 | 3.00 | 3.00 | 3.00 | 3.00 | 3.00 | 3.00 | 3.00 |
| Levosandol (manufactured by Takasago International Corp.) | 4.00 | 4.00 | 4.00 | 4.00 | 4.00 | 4.00 | 4.00 | 4.00 |
| Orange oil | 8.00 | 8.00 | 8.00 | 8.00 | 8.00 | 8.00 | 8.00 | 8.00 |

TABLE 4-continued

Prescription of Fragrance composition

| Ingredients | Compounding amount | | | | | | | |
|---|---|---|---|---|---|---|---|---|
| 10-oxa-16-hexadecanolide | 8.00 | 8.00 | 8.00 | 8.00 | 8.00 | 8.00 | 8.00 | 8.00 |
| Phenoxanol (manufactured by IFF Inc.) | 6.00 | 6.00 | 6.00 | 6.00 | 6.00 | 6.00 | 6.00 | 6.00 |
| Styrallyl acetate | 3.00 | 3.00 | 3.00 | 3.00 | 3.00 | 3.00 | 3.00 | 3.00 |
| Thesaron (manufactured by Takasago International Corp.) | 8.00 | 8.00 | 8.00 | 8.00 | 8.00 | 8.00 | 8.00 | 8.00 |
| Di-l-menthyl carbonate | 25.00 | 0.00 | 0.00 | 0.00 | 0.00 | 0.00 | 0.00 | 0.00 |
| Di-l-isopulegol carbonate | 0.00 | 25.00 | 0.00 | 0.00 | 0.00 | 0.00 | 0.00 | 0.00 |
| l-Menthyl-l-menthoxy ethyl carbonate | 0.00 | 0.00 | 25.00 | 0.00 | 0.00 | 0.00 | 0.00 | 0.00 |
| Di-l-menthoxy ethyl carbonate | 0.00 | 0.00 | 0.00 | 25.00 | 0.00 | 0.00 | 0.00 | 0.00 |
| l-Menthyl-l-isopulegol carbonate | 0.00 | 0.00 | 0.00 | 0.00 | 25.00 | 0.00 | 0.00 | 0.00 |
| l-Menthoxypropanediol methylheptenone ketal | 0.00 | 0.00 | 0.00 | 0.00 | 0.00 | 25.00 | 0.00 | 0.00 |
| l-Menthoxypropanediol benzaldehyde acetal | 0.00 | 0.00 | 0.00 | 0.00 | 0.00 | 0.00 | 25.00 | 0.00 |
| l-Menthoxypropanediol-l-citronellal acetal | 0.00 | 0.00 | 0.00 | 0.00 | 0.00 | 0.00 | 0.00 | 25.00 |
| Menthyl palmitate | 0.00 | 0.00 | 10.00 | 10.00 | 0.00 | 0.00 | 0.00 | 0.00 |
| Menthyl stearate | 10.00 | 10.00 | 0.00 | 0.00 | 0.00 | 0.00 | 0.00 | 0.00 |
| Menthyl isostearate | 0.00 | 0.00 | 0.00 | 0.00 | 10.00 | 10.00 | 10.00 | 10.00 |

Example 5

Shampoos

Shampoos in the following compositions (each 100 g) respectively containing the eight kinds of the fragrance compositions shown in Table 4 above in an amount of 1.0% were prepared. These shampoos showed cool and long-lasting cooling action.

<Prescription of Shampoo>

| Ingredients | Compounding amount (g) |
|---|---|
| Sodium polyoxyethylene lauryl ether sulfate | 14.00 |
| Lauric amide propylbetaine | 4.00 |
| Palm oil fatty acid diethanolamide | 3.00 |
| Cationized cellulose | 0.50 |
| Ethylene glycol distearate | 1.00 |
| Ethyl paraoxybenzoate | 0.25 |
| Citric acid | suitable amount |
| Fragrance composition | 1.00 |
| Purified water | balance |
| Total amount | 100.00 |

Example 6

Transparent shampoos in the following compositions (each 100 g) respectively containing the eight kinds of the fragrance compositions shown in Table 4 above in an amount of 1.0% were prepared. These shampoos showed cool and long-lasting cooling action.

<Prescription of Transparent Shampoo>

| Ingredients | Compounding amount (g) |
|---|---|
| Polyquaternium-10 | 10.0 |
| Sodium laureth sulfate Na (30% aqueous solution) | 300.0 |
| Lauroylsarcosine Na (30% aqueous solution) | 50.0 |
| Cocamide propene betaine | 100.0 |
| Palm fatty acid diethanolamide | 40.0 |
| 1,3-Butylene glycol | 20.0 |
| Citric acid | 3.0 |
| Methylparaben | 2.0 |
| Propylparaben | 0.5 |
| Disodium edetate | 1.0 |
| l-Menthol | 6.3 |
| Menthyl glyoxylate hydrate | 0.6 |
| Vanillyl butyl ether | 0.1 |
| Fragrance composition | 10.0 |
| Purified water | balance |
| Total amount | 1000.0 |

Example 7

Mist-Like Aromatic Deodorant

Mist-like aromatic deodorants in the following compositions (each 100 g) respectively containing the eight kinds of the fragrance compositions shown in Table 4 above in an amount of 0.5% were prepared. These deodorants showed cool and long-lasting cooling action.

<Prescription of Mist-Like Aromatic Deodorant Agent>

| Ingredients | Compounding amount (g) |
|---|---|
| Polyoxyethylene-hardened castor oil (EO40) | 1.0 |
| Polyoxyethylene-hardened castor oil (EO60) | 0.5 |
| 95% Ethyl alcohol | 2.5 |
| Methylparaben | 0.1 |
| l-Menthol | 0.25 |
| l-Menthoxy-1,2-propanediol | 0.25 |
| Vanillyl butyl ether | 0.05 |
| Fragrance composition | 0.5 |
| Purified water | balance |
| Total amount | 100.00 |

Example 8

Tooth Paste

Seven kinds of tooth pastes were prepared according to the prescription in Table 5. These tooth pastes showed cool and long-lasting cooling action.

TABLE 5

Prescription of Tooth paste

| Ingredients | Compounding amount | | | | | | |
|---|---|---|---|---|---|---|---|
| l-menthol | 0.25 | 0.25 | 0.25 | 0.25 | 0.25 | 0.25 | 0.25 |
| Calcium hydrogen phosphate (dihydrate) | 50.00 | 50.00 | 50.00 | 50.00 | 50.00 | 50.00 | 50.00 |
| Glycerin | 25.00 | 25.00 | 25.00 | 25.00 | 25.00 | 25.00 | 25.00 |
| Sodium lauryl sulfate | 1.40 | 1.40 | 1.40 | 1.40 | 1.40 | 1.40 | 1.40 |
| Carboxymethyl cellulose sodium salt | 1.50 | 1.50 | 1.50 | 1.50 | 1.50 | 1.50 | 1.50 |
| Saccharin sodium salt | 0.20 | 0.20 | 0.20 | 0.20 | 0.20 | 0.20 | 0.20 |
| Sodium benzoate | 0.10 | 0.10 | 0.10 | 0.10 | 0.10 | 0.10 | 0.10 |
| Strawberry type flavor (manufactured by Takasago International Corp.) | 0.70 | 0.70 | 0.70 | 0.70 | 0.70 | 0.70 | 0.70 |
| Di-l-menthyl carbonate | 0.20 | 0.00 | 0.00 | 0.00 | 0.00 | 0.00 | 0.00 |
| Di-l-isopulegol carbonate | 0.00 | 0.20 | 0.00 | 0.00 | 0.00 | 0.00 | 0.00 |
| l-Menthyl-l-menthoxy ethyl carbonate | 0.00 | 0.00 | 0.20 | 0.00 | 0.00 | 0.00 | 0.00 |
| Di-l-menthoxy ethyl carbonate | 0.00 | 0.00 | 0.00 | 0.20 | 0.00 | 0.00 | 0.00 |
| l-Menthyl-l-isopulegol carbonate | 0.00 | 0.00 | 0.00 | 0.00 | 0.20 | 0.00 | 0.00 |
| l-Menthoxypropanediol methylheptenone ketal | 0.00 | 0.00 | 0.00 | 0.00 | 0.00 | 0.20 | 0.00 |
| l-Menthoxypropanediol-l-citronellal acetal | 0.00 | 0.00 | 0.00 | 0.00 | 0.00 | 0.00 | 0.25 |
| Menthyl palmitate | 0.05 | 0.05 | 0.00 | 0.00 | 0.00 | 0.00 | 0.00 |
| Menthyl stearate | 0.00 | 0.00 | 0.05 | 0.05 | 0.00 | 0.00 | 0.00 |
| Menthyl isostearate | 0.00 | 0.00 | 0.00 | 0.00 | 0.05 | 0.05 | 0.00 |
| Purified water (balance) | | | | | | | |
| Total | 100.00 | 100.00 | 100.00 | 100.00 | 100.00 | 100.00 | 100.00 |

Example 9

Lemon-Flavored Chewing Gum

Seven kinds of lemon-flavored chewing gums were prepared according to the prescription in Table 6. These chewing gums showed cool and long-lasting cooling action.

TABLE 6

Prescription of Chewing gum with lemon flavor

| Ingredients | Compounding amount (g) | | | | | | |
|---|---|---|---|---|---|---|---|
| Gum base | 100.00 | 100.00 | 100.00 | 100.00 | 100.00 | 100.00 | 100.00 |
| Sugar | 250.00 | 250.00 | 250.00 | 250.00 | 250.00 | 250.00 | 250.00 |
| Glucose | 40.00 | 40.00 | 40.00 | 40.00 | 40.00 | 40.00 | 40.00 |
| Corn syrup | 60.00 | 60.00 | 60.00 | 60.00 | 60.00 | 60.00 | 60.00 |
| Glycerin | 3.00 | 3.00 | 3.00 | 3.00 | 3.00 | 3.00 | 3.00 |
| Lemon type fravor (manufactured by Takasago international Corp.) | 4.50 | 4.50 | 4.50 | 4.50 | 4.50 | 4.50 | 4.50 |
| l-Menthol | 1.00 | 1.00 | 1.00 | 1.00 | 1.00 | 1.00 | 1.00 |
| Di-l-menthyl carbonate | 0.80 | 0.00 | 0.00 | 0.00 | 0.00 | 0.00 | 0.00 |
| Di-l-isopulegol carbonate | 0.00 | 0.85 | 0.00 | 0.00 | 0.00 | 0.00 | 0.00 |
| l-Menthyl-l-menthoxy ethyl carbonate | 0.00 | 0.00 | 0.80 | 0.00 | 0.00 | 0.00 | 0.00 |
| Di-l-menthoxy ethyl carbonate | 0.00 | 0.00 | 0.00 | 0.80 | 0.00 | 0.00 | 0.00 |
| l-Menthyl-l-isopulegol carbonate | 0.00 | 0.00 | 0.00 | 0.00 | 0.80 | 0.00 | 0.00 |
| l-Menthoxypropanediol methylheptenone ketal | 0.00 | 0.00 | 0.00 | 0.00 | 0.00 | 0.85 | 0.00 |
| l-Menthoxypropanediol-l-citronellal acetal | 0.00 | 0.00 | 0.00 | 0.00 | 0.00 | 0.00 | 0.80 |
| Menthyl palmitate | 0.05 | 0.00 | 0.05 | 0.00 | 0.00 | 0.00 | 0.00 |
| Menthyl stearate | 0.00 | 0.00 | 0.00 | 0.05 | 0.05 | 0.00 | 0.00 |
| Menthyl isostearate | 0.00 | 0.00 | 0.00 | 0.00 | 0.00 | 0.00 | 0.05 |

The invention claimed is:

1. A cooling sensation agent composition, comprising at least one compound selected from acetals or ketals, single or mixed carbonic esters, and carboxylic esters consisting of the compounds represented by the following Formulae (1), (2), and (4):

acetals or ketals represented by Formula (1)

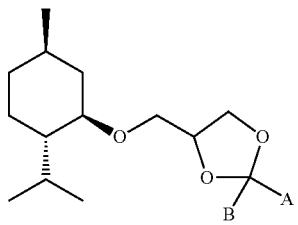

(1)

wherein, A is an alicyclic hydrocarbon group which may have one or more substituents, B is a hydrogen atom or a hydrocarbon group which may have one or more substituents, and the total number of carbon atoms in A and B is in the range of 6 to 18;

single or mixed carbonic esters of one or two kinds of alcohols represented by Formula (2):

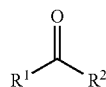

(2)

wherein, $R^1$ and $R^2$ each represent a residue of an alcohol selected from the group consisting of l-menthol, l-isopulegol, 3-(l-menthoxy)propan-1,2-diol, 2-(l-menthoxy)ethan-1-ol,3-(l-menthoxy)propan-1-ol, 2-methyl-3-(l-menthoxy)propan-1,2-diol, and para-menthan-3,8-diol, and $R^1$ and $R^2$ are not l-menthol or l-isopulegol residues at the same time;

and carboxylic esters represented by Formula (4):

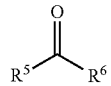

(4)

wherein, $R^5$ represents a residue of an alcohol selected from the group consisting of 3-(l-menthoxy)propan-1,2-diol, 2-(l-menthoxy)ethan-1-ol, 3-(l-menthoxy)propan-1-ol, 2-methyl-3-(l-menthoxy)propan-1,2-diol, and para-menthan-3,8-diol, and $R^6$ represents a hydrocarbon group having 11 to 19 carbon atoms that may be branched and contain one or more unsaturated bonds.

2. The cooling sensation agent composition according to claim 1, wherein the compounds represented by Formulae (1), (2), and (4) have a ClogP of 3.0 or more and a molecular weight of 250 or more and 600 or less and provide cooling action.

3. The cooling sensation agent composition according to claim 1, further comprising at least one kind of cooling sensation substance other than the compounds of Formulae (1), (2), and (4).

4. The cooling sensation agent composition according to claim 3, wherein the cooling sensation substance other than the compounds of Formulae (1), (2), and (4) is selected from the group consisting of menthol, menthone, camphor, pulegol, isopulegol, cineol, mint oil, peppermint oil, spearmint oil, eucalyptus oil, 3-(l-menthoxy)propan-1,2-diol, N-alkyl-p-menthane-3-carboxamide, 2-methyl-3-(l-menthoxy)propan-1,2-diol, p-menthan-3,8-diol, 2-(l-menthoxy)ethan-1-ol, 3-(l-menthoxy)propan-1-ol, 4-(l-menthoxy)butan-1-ol, menthyl 3-hydroxybutanoate, menthyl lactate, menthone glycerol ketal, N-methyl-2,2-isopropylmethyl-3-methylbutane amide, and menthyl glyoxylate.

5. A sensory stimulation agent composition, comprising the cooling sensation agent composition according to claim 1.

6. The sensory stimulation agent composition according to claim 5, further comprising at least one warming and pungent substance.

7. The sensory stimulation agent composition according to claim 6, wherein the warming and pungent substance is selected from the group consisting of vanillyl ethyl ether, vanillyl propyl ether, vanillin propylene glycol acetal, ethylvanillin propylene glycol acetal, capsaicin, gingerol, vanillyl butyl ether, 4-(l-menthoxymethyl)-2-(3'-methoxy-4'-hydroxyphenyl)-1,3-dioxolane, pepper oil, pepper oleoresin, ginger oleoresin, nonylic acid vanillyl amide, jamboo oleoresin, zanthoxylum piperitum peel extract, sanshool-I, sanshool-II, sanshoamide, black pepper extract, chavicine, piperine, and spilanthol.

8. A flavor or fragrance composition, a beverage or food product, a perfume or cosmetic product, a toiletry product, a daily utensil product or grocery, a fiber, a fiber product, a cloth or a medicine, comprising the cooling sensation agent composition according to claim 1 or the sensory stimulation agent composition according to claim 7.

9. A method of providing a cooling sensation effect, comprising applying one of the products according to claim 8 directly to the skin or scalp, into the oral cavity, or to a fiber, a fiber product, or a cloth which is applied to the skin, scalp or oral cavity.

10. A flavor or fragrance composition, comprising the cooling sensation agent composition according to claim 1 or the sensory stimulation agent composition according to claim 7 in an amount of 0.0001 to 90% by mass.

11. A beverage or food product, a perfume or cosmetic product, a toiletry product, a daily utensil product or grocery, a fiber, a fiber product, a cloth or a medicine, comprising the cooling sensation agent composition according to claim 1 or the sensory stimulation agent composition according to claim 7 in an amount of $1 \times 10^{-7}$ to 20% by mass.

12. A method of cool processing a fiber, fiber product, or a cloth, comprising compounding or processing the cooling sensation agent composition according to claim 1 or the sensory stimulation agent composition according to claim 7 with the fiber, the fiber product, or the cloth.

13. A method of producing a flavor or fragrance composition, a beverage or food product, a perfume or cosmetic product, a toiletry product, a daily utensil product or grocery, or a medicine, comprising compounding the cooling sensation agent composition according to claim 1 or the sensory stimulation agent composition according to claim 7 with the flavor or fragrance composition, the beverage or food product, the perfume or cosmetic product, the toiletry product, the daily utensil product or grocery, or the medicine.

14. An acetal or ketal represented by Formula (1')

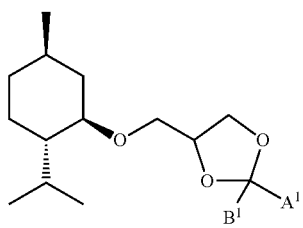

wherein, $A^1$ is an alicyclic hydrocarbon group which may have one or more substituents, $B^1$ is a hydrogen atom or a hydrocarbon group which may have one or more substituents, and the total number of carbon atoms in $A^1$ and $B^1$ is in the range of 6 to 18.

15. A single or mixed carbonic ester of one or two kinds of alcohols represented by Formula (2'):

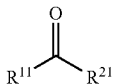

wherein, $R^{11}$ and $R^{21}$ each represent a residue of an alcohol selected from the group consisting of l-menthol, l-isopulegol, 3-(l-menthoxy)propan-1,2-diol, 2-(l-menthoxy)ethan-1-ol, 3-(l-menthoxy)propan-1-ol, 2-methyl-3-(l-menthoxy)propan-1,2-diol, and para-menthan-3,8-diol, and $R^1$ and $R^2$ are not l-menthol or l-isopulegol residues at the same time.

16. A carboxylic ester represented by Formula (4):

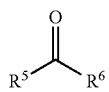

wherein, $R^5$ represents a residue of an alcohol selected from the group consisting of 3-(l-menthoxy)propan-1,2-diol, 2-(l-menthoxy)ethan-1-ol, 3-(l-menthoxy)propan-1-ol, 2-methyl-3-(l-menthoxy)propan-1,2-diol, and para-menthan-3,8-diol, and $R^6$ represents a hydrocarbon group having 11 to 19 carbon atoms that may be branched and contain one or more unsaturated bonds.

* * * * *